US009261781B2

(12) United States Patent
Bell et al.

(10) Patent No.: US 9,261,781 B2
(45) Date of Patent: *Feb. 16, 2016

(54) PREPARATION OF NORBORNANE-BASED PAC BALLASTS

(71) Applicants: Promerus, LLC, Brecksville, OH (US); Sumitomo Bakelite Co., Ltd., Tokyo (JP)

(72) Inventors: Andrew Bell, Lakewood, OH (US); Keitaro Seto, Brecksville, OH (US); Hiroaki Makabe, Tokyo (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/963,304

(22) Filed: Aug. 9, 2013

(65) Prior Publication Data

US 2013/0323640 A1 Dec. 5, 2013

Related U.S. Application Data

(63) Continuation of application No. 13/248,015, filed on Sep. 28, 2011, now Pat. No. 8,530,133.

(60) Provisional application No. 61/387,096, filed on Sep. 28, 2010.

(51) Int. Cl.
| | | |
|---|---|---|
| G03F 7/023 | (2006.01) |
| G03F 7/022 | (2006.01) |
| C07C 43/178 | (2006.01) |
| C07C 245/12 | (2006.01) |
| C07C 39/17 | (2006.01) |
| C07C 309/71 | (2006.01) |
| G03F 7/40 | (2006.01) |

(52) U.S. Cl.
CPC ............... *G03F 7/022* (2013.01); *C07C 39/17* (2013.01); *C07C 43/1782* (2013.01); *C07C 43/1783* (2013.01); *C07C 43/1788* (2013.01); *C07C 245/12* (2013.01); *C07C 309/71* (2013.01); *G03F 7/023* (2013.01); *G03F 7/0233* (2013.01); *C07C 2101/16* (2013.01); *C07C 2102/10* (2013.01); *C07C 2102/24* (2013.01); *C07C 2103/86* (2013.01); *G03F 7/40* (2013.01)

(58) Field of Classification Search
CPC ... G03F 7/0233; C07C 39/17; C07C 43/1782; C07C 43/1783; C07C 245/10; C07C 245/08; C07C 43/1788; C07C 245/12
USPC .......... 430/165, 191, 192, 193; 534/556, 557; 568/611, 660, 719, 734
See application file for complete search history.

(56) References Cited

U.S. PATENT DOCUMENTS

| | | | |
|---|---|---|---|
| 3,222,404 A | 12/1965 | van den Brink et al. | |
| 3,234,177 A | 2/1966 | van Schooten | |
| 3,251,803 A * | 5/1966 | Caldwell et al. | ............... 528/201 |
| 3,517,071 A | 6/1970 | Caldwell et al. | |
| 3,864,307 A | 2/1975 | Nast et al. | |
| 3,931,060 A | 1/1976 | Schubart et al. | |
| 4,061,777 A | 12/1977 | Mardiguian | |
| 4,157,400 A | 6/1979 | Mardiguian | |
| 5,283,374 A | 2/1994 | Jeffries, III | |
| 5,488,182 A | 1/1996 | Kobayashi et al. | |
| 5,571,656 A | 11/1996 | Kingsley et al. | |
| 5,602,260 A | 2/1997 | Blakeney et al. | |
| 6,153,721 A | 11/2000 | McCarthy et al. | |
| 6,232,417 B1 | 5/2001 | Rhodes et al. | |
| 6,455,650 B1 | 9/2002 | Lipian et al. | |
| 7,241,561 B1 | 7/2007 | Lynch et al. | |
| 7,781,131 B2 | 8/2010 | Makabe | |
| 8,530,133 B2 * | 9/2013 | Bell et al. | ....................... 430/192 |
| 8,753,790 B2 * | 6/2014 | Onishi et al. | ................... 430/192 |
| 2010/0152185 A1 | 6/2010 | Chu et al. | |
| 2011/0144284 A1 * | 6/2011 | Heuer et al. | ................... 525/394 |
| 2011/0230626 A1 * | 9/2011 | Heure et al. | ................... 525/462 |
| 2012/0135352 A1 * | 5/2012 | Bell et al. | ................... 430/286.1 |

FOREIGN PATENT DOCUMENTS

| | | |
|---|---|---|
| DE | 2231069 A1 | 1/1974 |
| EP | 0126193 A1 | 11/1984 |
| EP | 1 923 742 A1 | 5/2008 |
| FR | 2469405 A1 | 5/1981 |
| GB | 936760 A | 9/1963 |
| GB | 1 009 019 A | 11/1965 |
| GB | 1548875 A | 7/1979 |
| JP | S63-77933 A | 4/1988 |
| JP | 11 044948 A | 2/1999 |
| JP | 2010-209016 A | 9/2010 |
| WO | WO 2006/017035 A1 | 2/2006 |
| WO | WO 2006/102007 A2 | 9/2006 |

OTHER PUBLICATIONS

Kheifits, "Condensation of Norbornene with o-Cresol and Conversions of the Condensation Product", Journal of General Chemistry USSR Consultants Bureau, New York, NY, US, vol. 33 (7), Jan. 1, 1963, pp. 2352-2356.
STN on the web (CAPlus), AN: 1964:411067 (RN: 98723-01-4, 98723-02-5).
STN on the web (CAPlus), 1964, AN: 1964:432636 (RN: 106410-45-1).
STN on the web (Registry), 1984, RN: 29468-55-1.
Pliev, T. N., Izvestiya Vysshikh Uchebnykh Zavedenij. Khimiya i Khimicheskaya Tekhnologiya, 1993, vol. 36, No. 3, pp. 42-45.

(Continued)

Primary Examiner — John S Chu
(74) Attorney, Agent, or Firm — Balaram Gupta

(57) ABSTRACT

Embodiments in accordance with the present invention provide for norbornane-type ballast materials, norbornane-type photoactive compounds derived from such ballast materials and alkali-soluble positive-tone polymer compositions that encompass such norbornane-type photoactive compounds and one of a PBO or PNB resin.

19 Claims, No Drawings

(56) References Cited

OTHER PUBLICATIONS

STN on the web (CAPlus), 1996, AN: 1964:451249 (RN: 98723-01-4, 98723-02-5).

Salvador-Recatala, V., et al., Journal of Pharmacology and Experimental Therapeutics, 2006, vol. 319, No. 2, pp. 758-764.

MacDonald, D., et al., Bioorganic & Medicinal Chemistry Letters, 2008, vol. 18, pp. 2023-2027.

\* cited by examiner

PREPARATION OF NORBORNANE-BASED PAC BALLASTS

CROSS REFERENCE TO RELATED APPLICATIONS

This application is a continuation of U.S. application Ser. No. 13/248,015 filed Sep. 28, 2011, now allowed, which claims the benefit of U.S. Provisional Application No. 61/387,096, filed Sep. 28, 2010, both of which are incorporated herein by reference in their entirety.

TECHNICAL FIELD

The present invention relates generally to positive-tone photosensitive resin compositions that encompass a photoactive compound (PAC) and the structures formed therefrom or thereusing and more specifically to such resin compositions encompassing PACs made from norbornane-based ballast (NBane-type ballast) materials, methods of making such ballast materials and the PAC materials and the structures formed therefrom or thereusing.

DETAILED DESCRIPTION

Polyimide (PI), polybenzoxazole (PBO) and polynorbornene (PNB) resins generally are known materials that are used for forming a surface protecting layer or an interlayer dielectric in the manufacture of semiconductor devices. To effectively integrate such resins into normal semiconductor processing, it has been found advantageous to provide such resins in the form of a positive-tone, aqueous base developable, photosensitive resin composition. In this manner, a separate pattern and etch process utilizing a photoresist material is avoided to form a patterned layer of such resins.

While various types of such PI, PBO and PNB photosensitive resin compositions are known, the miniaturization and high integration of semiconductor devices has, in recent years, placed a demand on resin composition suppliers for materials with both a lower resin cure temperature and enhanced imageability.

It has been shown that photosensitive resin compositions of the above resins can be made by incorporating therein, a photo-active compound (PAC). For example, in U.S. Pat. No. 7,781,131 to Hiroaki Makabe, entitled "Positive photosensitive resin composition, cured layer, protecting layer, insulating layer and semiconductor device and display therewith" (the '131 patent), the use of a diazoquinone-based PAC provides for a positive-type photosensitive PBO resin composition which can be developed using an alkaline aqueous solution. The aforementioned diazoquinone compound based PACs of the '131 patent are derived from ballast materials that encompass one or more phenolic moieties where such moieties are reacted with 1,2-naphthoquinone-2-diazido-5-sulfonic acid, 1,2-naphthoquinone-2-diazido-4-sulfonic acid or the like. When such PACs are mixed with, for example a polybenzoxazole resin precursor, an appropriate casting solvent and a cyclic compound having an alcoholic hydroxyl group, a photosensitive resin composition capable of being cast onto a substrate to form a film is provided. Once such a film is formed, an image can be developed by an image-wise exposure of the cast resin film with an appropriate wavelength of actinic radiation and the subsequent removal of regions of the film made soluble by such exposure. This image forming process is well known and discussed in the '131 patent.

Once such an image is formed, the '131 patent describes how the PBO resin precursor is dehydrated by ring-closing during a curing process using an elevated temperature appropriate to cause such ring-closure thus forming a polybenzoxazole resin having high heat resistance. However, remarkable miniaturization and high integration of semiconductor chips in recent years has reduced heat resistance, particularly of storage chips, and increased the need for PACs that provide increased image resolution and contrast. With regard to heat resistance, the '131 patent provides for embodiments comprising a PBO resin precursor capable of being cured at appropriately low temperatures and after such curing providing excellent thermal stability. The current application provides embodiments of norbornane-based ballasts that are capable of being formed into PACs that provide the desired increased image resolution and contrast in PBO resin compositions as well as in appropriate PNB resin compositions.

More specifically, embodiments in accordance with the present invention use hydroarylation chemistry to generate norbornane-arylol linkages and to join norbornane or similar units to one another. The phenol norbornane/polycyclic structures that such embodiments provide are then readily converted to useful PACs by reaction with one of the following sulfonic acids or their respective acid chlorides: 1,2-naphthoquinone-2-diazido-5-sulfonic acid, 1,2-naphthoquinone-2-diazido-4-sulfonic acid or 2-diazo-4-hydrosulfonylcyclohex-3-enone, the structures of which are shown, respectively below, to form the esters thereof:

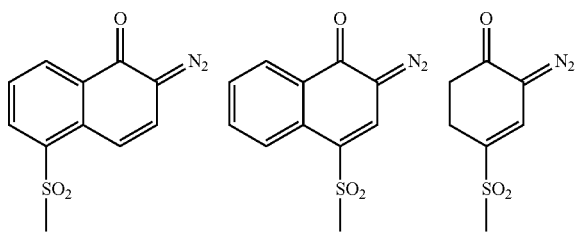

Some exemplary phenolic structures encompassing norbornane-type moieties (also referred to as NBane-type polyols, NBane-type arylols, or NBane-type ballast moieties) that are in accordance with the NBane-type ballast and NBane-type PAC embodiments of the present invention are provided. In addition, several exemplary methods for making such structures and exemplary methods for reacting such NBane-type polyol structures to form the aforementioned NBane-type PACs are also provided. Such NBane-type ballast moieties include, but are not limited to the follow exemplary structures:

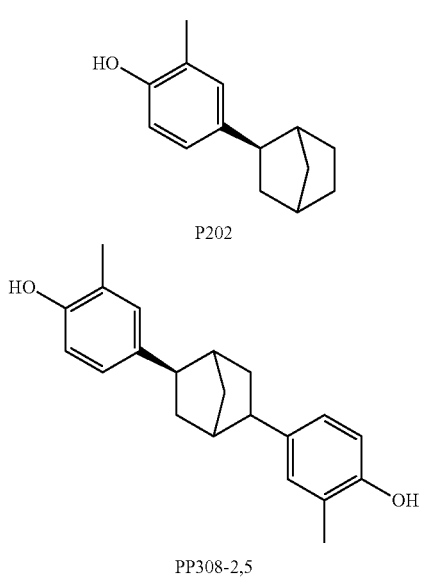

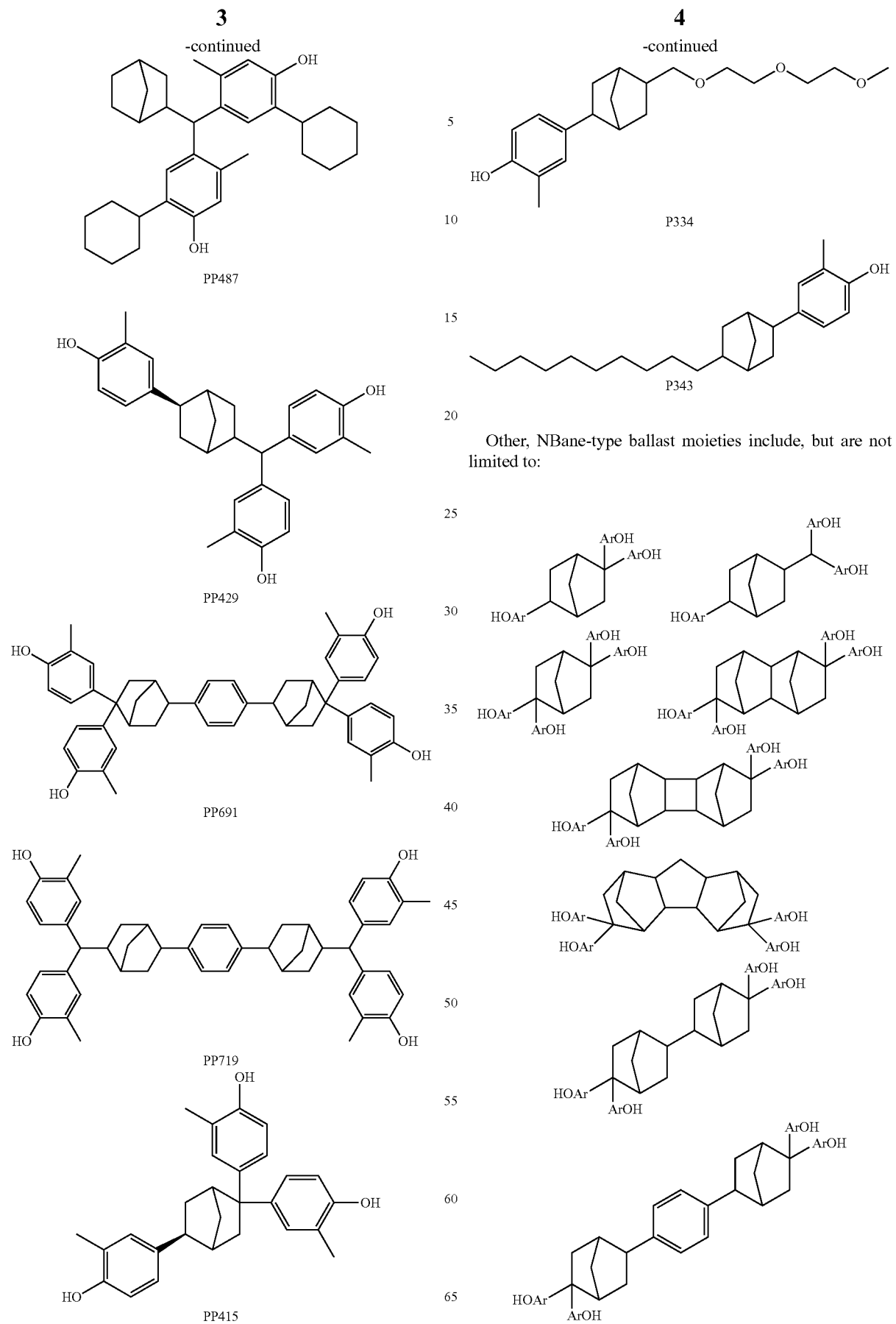
Other, NBane-type ballast moieties include, but are not limited to:

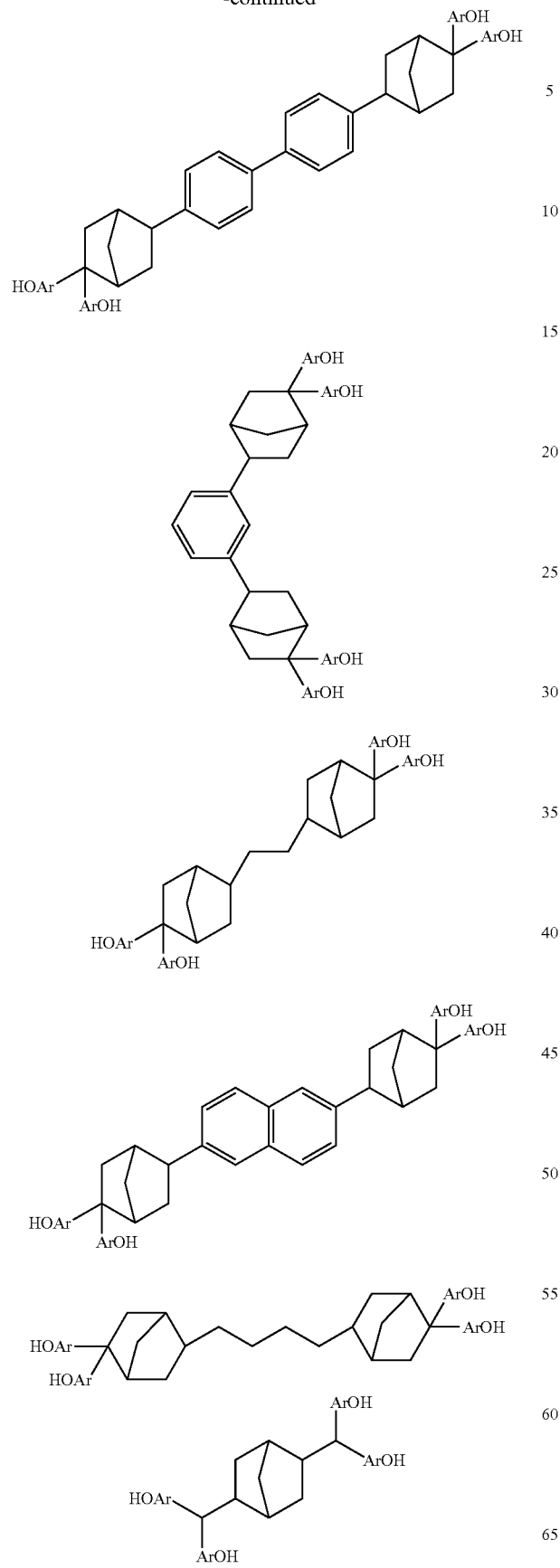
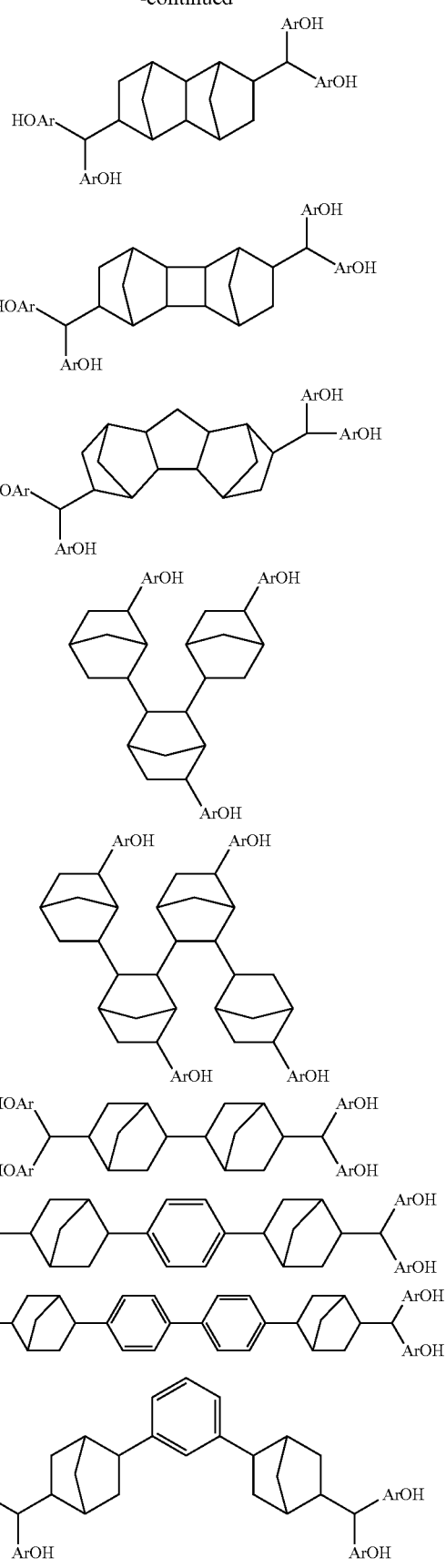

-continued where ArOH is understood to represent a substituted or unsubstituted aryl hydroxide moiety (also referred to as an arylol), and for each structure having in excess of one ArOH, it will be understood that such excess ArOHs are optional.

While specific examples for the preparation of several of the above NBane-type arylols is provided below, in general most synthetic routes begin by forming both an arylol and one of a norbornenone, a norbornene carboxaldehyde, a phenylene(norbornanone), a norbornene-alkylene-norbornene (where alkylene represents an alkyl chain of 2 or more carbons), a norbornene-aryl(cycloalkyl)-norbornene (where aryl(cycloalkyl) represents either an aryl group or a cyclic alkyl group) or a norbornene dimer. Where such NBane-type beginning material is an aldehyde or ketone, addition across the carbonyl bond by an arylol can be accomplished to provide a di-arylol result at each carbonyl, thus forming an NBane-type arylol. Where such norbornene-type starting material is absent a carbonyl group, one or more such carbonyl groups can be added and an NBane-type arylol is formed as described above. Alternately, an arylol can be added across any C=C bonds that are present, for example via a hydroarylation reaction. In this manner, NBane-type arylols can be advantageously formed with essentially any number of arylol substituents and is thus distinct from the teachings of U.S. Pat. No. 3,517,071 (the '071 patent) which only teaches the formation of diphenol moieties where a single carbon atom is covalently bonded to two phenol moieties. Such single carbon atom being one of a carbon within the polycyclic structure or a methylene group, not within the polycyclic structure, that is covalently bonded to a polycyclic ring carbon. The '071 patent being directed to the preparing geminal diphenol moieties that are useful for preparing polymers having improved temperature properties and solubility in volatile solvents.

Further to distinguishing embodiments in accordance with the present invention from the disclosures of the '071 patent, NBane-type polyols such as PP429 and PP691, the structures of which are provided above, can be seen to provide both a single arylol substitution and a diphenol substituted methylene in the former and in the latter two norbornane structures, each having a geminal diphenol substitution, linked to one another by an aromatic linking group. With regard to PP429, the '071 patent does not teach or even suggest a method for providing any arylol substitution other than a geminal diarylol substitution, thus PP429 distinguished from the teachings and disclosure of such patent. Turning to PP691, while such structure only encompasses geminal diarylol substitution of norbornane, as mentioned above, such structure also encompasses an aromatic linking group to a second diphenol substituted norbornane and hence is also distinguished from the teachings and disclosure of the '071 patent.

It will be understood that as used herein, above and below, reference to norbornene-type moieties, starting materials or structures refers to a polycyclic structure in accordance with Structure 1 shown below, where m is an integer from 0 to 3, at least one of $R^a$, $R^b$, $R^c$ or $R^d$ is not hydrogen and $R^e$ is W or W* as defined below. It will further be understood that as used herein, above and below, reference to norbornane polyols, ballast or PACs refers to such a materials encompassing at least one polycyclic structure in accordance with Structure 2 shown below, where m is as defined for Structure 1 and at least one of $R^a$, $R^b$, $R^c$ or $R^d$ is a substituted or unsubstituted arylol and is W or W* as defined below.

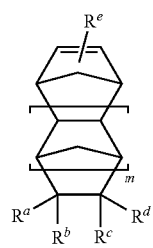

1

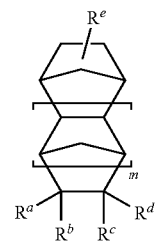

2

Further, while specific examples of forming a PAC from NBane-type arylols are provided, in general, the reaction is carried out by first forming a solution of a specific NBane-type arylols with an appropriate amount of one of the aforementioned sulfonic acids or their analogous acid chlorides and then adding an excess of an organic amine such as triethyl amine, and then adding to such solution. It will be understood that the appropriate amount of sulfonic acid or acid chloride is a function of a desired amount of ester formation. Generally such reactions are carried out at or near room temperature and yield a mixture of products characterized by the number of phenols that are converted to sulfonic acid esters.

The substitution of the norbornyl unit by arylols can be such that the molecules generated are either symmetric or asymmetric based on reaction sites or through stereo isomers. It is believed that it is advantageous for such NBane-type polyols to encompass a number of isomers as the PACs formed will likely impart improved solubility in the various resin compositions. Likewise, the endo/exo-substitution of norbornene fragments can lead to mixtures of diastereomers, which also is believed to be likely to impart improved solubility of the resulting PACs in the photosensitive resin composition embodiments that are in accordance with the present invention.

NBane-type ballast embodiments in accordance with the present invention therefore encompass a NBane-type moiety having either one norbornane-type structure or more than one norbornane-type structure. Where there are more than one norbornane-type structure, such structures are joined by one or more covalent bonds or by one or more linking groups as defined below. Further, where there are more than one norbornane-type structure, at least one of such structures encompasses one or more arylol substituents.

In some such embodiments, each arylol substituent can also include one or more other substituents selected from a halogen, a $C_1$ to $C_6$ alkyl, a $C_3$ to $C_{12}$ cycloalkyl and a substituted or unsubstituted phenyl group.

Still further, some of the norbornane-type ballast embodiments of the present invention can be represented by one of the following norbornane-type structures:

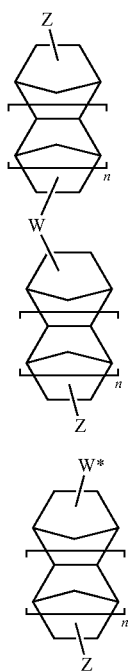

AA

BB

Where for each formulae, each n is an independently selected integer from 0 to 3; Z represents one to four substituted or unsubstituted ArOH substituents (arylols); W in formula AA is either a covalent bond or a divalent linking group selected from a $C_1$ to $C_{12}$ alkyl, ether or polyether, a $C_3$ to $C_{12}$ cycloalkyl, aryl or alkaryl group, or one or more norbornane-type moieties, W* in formula BB is optional and, if present, is monovalent and can be described generally as a $C_1$ to $C_{12}$ alkyl, ether or polyether, a $C_3$ to $C_{12}$ cycloalkyl, aryl or alkaryl group, or one or more norbornane-type moieties; and more specifically W* can be $-(CH2)_n*CH_3$, $-(CH_2)_nPh$, $-(CH_2)_sO(CH_2CH_2O)_tH$, $-(CH_2)_sO(CH_2CH_2O)_tC(O)CH_3$, $-(CH_2)_s(O)CH_3$, $-(CH_2)_sO(CH_2CH_2O)_t*CH_3$, $-(CH_2)_sOCH_2CH_2OCH_2C(CF_3)_2OH$, $-(CH_2)_sC(CF_3)_2OH$, $-(CH_2)_sOCH_2C(CF_3)_2OH$, $-(CH_2)_sCO_2Et$, $-(CH_2)_sCO_2H$, $-(CH_2)_sC_6H_4OH$, $-(CH_2)_sC(O)C_6H_4OH$, $-(CH_2)_sC(O)NHC_6H_4OH$, and $-(CH_2)_sN(H)S(O)_2CF_3$; where n and n* are integers from 0 to 6 or 0 to 11, respectively; s is an integer from 1 to 6; and t is 0 or 3 and t* is 2 or 3. That is to say that any of the aforementioned groups as W* is not present it is hydrogen. However, with the proviso that when n=0 in formula BB and Z is a group of formula:

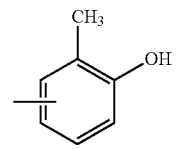

then W* is not hydrogen.

Exemplary NBane-type ballasts encompassed by the ballast embodiments in accordance with the present invention include, but are not limited to: 4-(5-hexylbicyclo[2.2.1]heptan-2-yl)-2-methylphenol, 4-(5-hexylbicyclo[2.2.1]heptan-2-yl)-2-isopropylphenol, 2-cyclohexyl-4-(5-hexylbicyclo[2.2.1]heptan-2-yl)-5-methylphenol, 4-(5-decylbicyclo[2.2.1]heptan-2-yl)-2-methylphenol, 4-(5-decylbicyclo[2.2.1]heptan-2-yl)-2-isopropylphenol, 2-cyclohexyl-4-(5-decylbicyclo[2.2.1]heptan-2-yl)-5-methylphenol, 4-(5-2,5,8,11-tetraoxadodecylbicyclo[2.2.1]heptan-2-yl)-2-methylphenol, 4-(5-2,5,8,11-tetraoxadodecylbicyclo[2.2.1]heptan-2-yl)-2-isopropylphenol, 4-(5-2,5,8,11-tetraoxadodecylbicyclo[2.2.1]heptan-2-yl)-2-cyclohexyl-5-methylphenol, 2-methyl-4-(5-phenylbicyclo[2.2.1]heptan-2-yl)phenol, 2-isopropyl-4-(5-phenylbicyclo[2.2.1]heptan-2-yl)phenol, 2-cyclohexyl-4-(5-phenylbicyclo[2.2.1]heptan-2-yl)phenol, ethyl 3-(5-(4-hydroxy-3-methylphenyl)bicyclo[2.2.1]heptan-2-yl)propanoate, ethyl 3-(5-(4-hydroxy-3-isopropylphenyl)bicyclo[2.2.1]heptan-2-yl)propanoate, ethyl 3-(5-(3-cyclohexyl-4-hydroxyphenyl)bicyclo[2.2.1]heptan-2-yl)propanoate, 4-(bicyclo[2.2.1]heptan-2-yl)-2-methylphenol, 4-(bicyclo[2.2.1]heptan-2-yl)-2-isopropylphenol 4-(5-((2-methoxyethoxy)methyl)bicyclo[2.2.1]heptan-2-yl)-2-methylphenol, 2-isopropyl-4-(5-((2-methoxyethoxy)methyl)bicyclo[2.2.1]heptan-2-yl)phenol, 2-cyclohexyl-4-(5-((2-methoxyethoxy)methyl)bicyclo[2.2.1]heptan-2-yl)-5-methylphenol, 4-(5-((2-(2-methoxyethoxy)ethoxy)methyl)bicyclo[2.2.1]heptan-2-yl)-2-methylphenol, 2-isopropyl-4-(5-((2-(2-methoxyethoxy)ethoxy)methyl)bicyclo[2.2.1]heptan-2-yl)phenol, 2-cyclohexyl-4-(5-((2-(2-methoxyethoxy)ethoxy)methyl)bicyclo[2.2.1]heptan-2-yl)-5-methylphenol, 2-methyl-4-(5-(3,3,3-trifluoro-2-hydroxy-2-(trifluoromethyl)propyl)bicyclo[2.2.1]heptan-2-yl)phenol, 2-isopropyl-4-(5-(3,3,3-trifluoro-2-hydroxy-2-(trifluoromethyl)propyl)bicyclo[2.2.1]heptan-2-yl)phenol, 2-cyclohexyl-4-(5-(3,3,3-trifluoro-2-hydroxy-2-(trifluoromethyl)propyl)bicyclo[2.2.1]heptan-2-yl)phenol, 4-(5-benzylbicyclo[2.2.1]heptan-2-yl)-2-methylphenol, 4-(5-benzylbicyclo[2.2.1]heptan-2-yl)-2-isopropylphenol, 4-(5-(2-methyl bicyclo[2.2.1]heptane)bicyclo[2.2.1]heptan-2-yl)-2-cyclohexylphenol, 4-(bicyclo[2.2.1]heptan-2-yl)-2-cyclohexylphenol, 4-(5-benzylbicyclo[2.2.1]heptan-2-yl)-2-methylphenol, 4-(5-(2-methyl bicyclo[2.2.1]heptan-2-yl)bicyclo[2.2.1]heptan-2-yl)-2-isopropylphenol, 4-(5-(2-methyl bicyclo[2.2.1]heptane)bicyclo[2.2.1]heptan-2-yl)-2-cyclohexylphenol, 4-(decahydro-1,4:5,8-dimethanonaphthalen-2-yl)-2-methylphenol, 4-(decahydro-1,4:5,8-dimethanonaphthalen-2-yl)-2-isopropylphenol, 4-(decahydro-1,4:5,8-dimethanonaphthalen-2-yl))-2-cyclohexylphenol, 4-(5-(4-hydroxybenzyl)bicyclo[2.2.1]heptan-2-yl)-2-methylphenol, 4-(5-(4-hydroxybenzyl)bicyclo[2.2.1]heptan-2-yl)-2,5-dimethylphenol, 2-cyclohexyl-4-(5-(methoxymethyl)bicyclo[2.2.1]heptan-2-yl)-5-methylphenol, 4-(5-(methoxymethyl)bicyclo[2.2.1]heptan-2-yl)-2-methylphenol, 2-methyl-4-(5-((oxiran-2-ylmethoxy)methyl)bicyclo[2.2.1]heptan-2-yl)phenol, 2-cyclohexyl-5-methyl-4-(5-((oxiran-2-ylmethoxy)methyl)bicyclo[2.2.1]heptan-2-yl)phenol, 2-methyl-4-(5-(6-(oxiran-2-yl)hexyl)bicyclo[2.2.1]heptan-2-yl)phenol, 2-cyclohexyl-5-methyl-4-(5-(6-(oxiran-2-yl)hexyl)bicyclo[2.2.1]heptan-2-yl)phenol, 2-cyclohexyl-4-(5-(methoxymethyl)bicyclo[2.2.1]heptan-2-yl)-5-methylphenol, 4-(5-(hydroxymethyl)bicyclo[2.2.1]heptan-2-yl)-2-methylphenol, 5-(5-cyclohexyl-4-hydroxy-2-methylphenyl)bicyclo[2.2.1]heptan-2-yl)methyl acetate, and (5-(4-hydroxy-3-methylphenyl)bicyclo[2.2.1]heptan-2-yl)methyl acetate.

Also, 4,4'-(bicyclo[2.2.1]heptan-2-ylmethylene)bis(2-methylphenol), 4,4'-(bicyclo[2.2.1]heptane-2,2-diyl)bis(2-methylphenol), 4,4'-((5S)-5-phenylbicyclo[2.2.1]heptan-2-yl(methylene)bis(2-methylphenol), 4,4'-((5S)-5-phenylbicyclo[2.2.1]heptane-2,2-diyl)bis(2-methylphenol), 4,4'-((5-phenylbicyclo[2.2.1]heptan-2-yl)methylene)bis(2-isopropyl-5-methylphenol), 4-(2-(4-hydroxy-3-isopropyl-5-methylphenyl)-5-phenylbicyclo[2.2.1]heptan-2-yl)-2-isopropyl-5-methylphenol, 4,4'-((5-phenylbicyclo[2.2.1]heptan-2-yl)methylene)bis(2-cyclohexyl-5-methylphenol), 2-cyclohexyl-4-(2-(3-cyclohexyl-4-hydroxy-5-methylphenyl)-5-phenylbicyclo[2.2.1]heptan-2-yl)-5-methylphenol, 4,4'-(bicyclo[2.2.1]heptane-2,5-diyl)bis(2-methylphenol), 4,4-(bicyclo[2.2.1]heptane-2,5-diyl)bis(2-isopropylphenol), 4,4'-(tetracyclo[6.2.1.13,6.0.2,7]dodecan-2,7-diyl)bis(2-methylphenol), 4,4'-(tetracyclo[6.2.1.13,6.0.2,7]dodecan-2,7-diyl)bis(2-isopropylphenol), 4,4'-(bicyclo[2.2.1]heptane-2,5-diyl)bis(2-cyclohexyl-5-methylphenol), 4,4-(tetracyclo[6.2.1.13,6.0.2,7]dodecan-2,7-diyl)bis(2-cyclohexyl-5-methylphenol), 4,4'-(5,5'-(2,2'-oxybis(ethane-2,1-diyl))bis(bicyclo[2.2.1]heptane-5,2-diyl))bis(2-cyclohexylphenol), 4,4'-(5,5'-(2,2'-oxybis(ethane-2,1-diyl))bis(bicyclo[2.2.1]heptane-5,2-diyl))bis(2-isopropylphenol), 4,4'-(5,5'-(2,2'-oxybis(ethane-2,1-diyl))bis(bicyclo[2.2.1]heptane-5,2-diyl))bis(2-methylphenol), 4,4'-(5,5'-(butane-1,4-diyl)bis(bicyclo[2.2.1]heptane-5,2-diyl))bis(2-methylphenol), 4,4'-(5,5'-(butane-1,4-diyl)bis(bicyclo[2.2.1]heptane-5,2-diyl))bis(2-isopropylphenol), 2-cyclohexyl-4-(5-(4-(5-(3-cyclohexyl-4-methylphenyl)bicyclo[2.2.1]heptan-2-yl)butyl)bicyclo[2.2.1]heptan-2-yl)phenol, 4,4'-(tetracyclo[6.2.1.13,6.0.2,7]dodecan-2-ylmethylene)bis(2-methylphenol), 4,4'-(tetracyclo[6.2.1.13,6.0.2,7]dodecan-2-ylmethylene)bis(2-isopropylphenol), 4,4'-(tetracyclo[6.2.1.13,6.0.2,7]dodecan-2-ylmethylene)bis(2-cyclohexyl-5-methylphenol), 4,4'-(5,5'-(1,4-phenylene)bis(bicyclo[2.2.1]heptane-5,2-diyl))bis(2-methylphenol), 4,4'-(5,5'-(1,4-phenylene)bis(bicyclo[2.2.1]heptane-5,2-diyl))bis(2-isopropylphenol), 4,4'-(5,5'-(1,4-phenylene)bis(bicyclo[2.2.1]heptane-5,2-diyl))bis(2-cyclohexylphenol), 4,4'-(5,5'-(biphenyl-4,4'-diyl)bis(bicyclo[2.2.1]heptane-5,2-diyl))bis(2-methylphenol), 4,4'-(5,5'-(biphenyl-4,4'-diyl)bis(bicyclo[2.2.1]heptane-5,2-diyl))bis(2-isopropylphenol), 4,4'-(5,5'-(biphenyl-4,4'-diyl)bis(bicyclo[2.2.1]heptane-5,2-diyl))bis(2-cyclohexylphenol), 4,4'-(Pentacyclo[8.2.1.14,7.02,9.08,3]tetradecan-2,8-yl)bis(2-methylphenol), 4,4'-(Pentacyclo[8.2.1.14,7.02,9.08,3]tetradecan-2,8-yl)bis(2-isopropylphenol), 4,4'-(Pentacyclo[8.2.1.14,7.02,9.08,3]tetradecan-2,8-yl)bis(2-cyclohexyl-5-methylphenol), 4,4'-(dodecahydro-1,4:5,8-dimethanobiphenylene-2,6-diyl)bis(2-methylphenol), 4,4'-(dodecahydro-1,4:5,8-dimethanobiphenylene-2,6-diyl)bis(2-isopropylphenol), and 4,4'-(dodecahydro-1,4:5,8-dimethanobiphenylene-2,6-diyl)bis(2-cyclohexyl-5-methylphenol).

Further, 4,4'-((5-(4-hydroxy-3-methylphenyl)bicyclo[2.2.1]heptan-2-yl)methylene)bis(2-methylphenol), 4,4'-((5-(4-hydroxy-3-isopropylphenyl)bicyclo[2.2.1]heptan-2-yl)methylene)bis(2-isopropylphenol), 4,4'-((5-(3-cyclohexyl-4-hydroxyphenyl)bicyclo[2.2.1]heptan-2-yl)methylene)bis(2-methylphenol), 4,4'-((5-(4-hydroxyphenyl)bicyclo[2.2.1]heptan-2-yl)methylene)bis(2-methylphenol), 4,4',4''-(bicyclo[2.2.1]heptane-2,2,5-triyl)tris(2-methylphenol), 4,4',4''-(bicyclo[2.2.1]heptane-2,2,5-triyl)tris(2-isopropylphenol), 4,4'-(5-(3-cyclohexyl-4-hydroxyphenyl)bicyclo[2.2.1]heptane-2,2-diyl)bis(2-methylphenol), 4,4'-(5-(4-hydroxyphenyl)bicyclo[2.2.1]heptane-2,2-diyl)bis(2-methylphenol), 5'-(5-(4-hydroxybenzyl)bicyclo[2.2.1]heptan-2-yl)-3,3''-dimethyl-[1,1':3',1''-terphenyl]-4,4''-diol, and 5'-(5-(4-hydroxyphenyl)bicyclo[2.2.1]heptan-2-yl)-3,3''-dimethyl-[1,1':3',1''-terphenyl]-4,4''-diol.

And still further, 4,4',4'',4'''-(5,5'-(1,4-phenylene)bis(bicyclo[2.2.1]heptane-5,2-diyl))bis(methanetriyl)tetrakis(2-methylphenol), 4,4',4'',4'''-(5,5'-(1,4-phenylene)bis(bicyclo[2.2.1]heptane-5,2-diyl))bis(methanetriyl)tetrakis(2-cyclohexyl-5-methylphenol), 4,4',4'',4'''-(5,5'-(1,4-phenylene)bis(bicyclo[2.2.1]heptane-5,2-diyl))bis(methanetriyl)tetrakis(2-isopropylphenol), 4,4',4'',4'''-(5,5'-(1,4-phenylene)bis(bicyclo[2.2.1]heptane-5,2-diyl)bis(methanetriyl)tetrakis(2,5-dimethylphenol), 4,4',4'',4'''-(5,5'-(1,4-phenylene)bis(bicyclo[2.2.1]heptane-5,2,2-triyl))tetrakis(2-methylphenol), 4,4'-(5-(4-(5-(5-cyclohexyl-4-hydroxy-2-methylphenyl)-5-(3-cyclohexyl-4-hydroxyphenyl)bicyclo[2.2.1]heptan-2-yl)phenyl)bicyclo[2.2.1]heptane-2,2-diyl)bis(2-cyclohexyl-5-methylphenol), 4,4',4'',4'''-(5,5'-(1,4-phenylene)bis(bicyclo[2.2.1]heptane-5,2,2-triyl))tetrakis(2,5-dimethylphenol), and 5'-(5-(bis(4-hydroxy-2,5-dimethylphenyl)methyl)bicyclo[2.2.1]heptan-2-yl)-3,3''-dimethyl-[1,1':3',1''-terphenyl]-4,4''-diol.

In some NBane-type ballast embodiments of the present invention the norbornane-type compound encompasses one of norbornane-type structures CC, shown below:

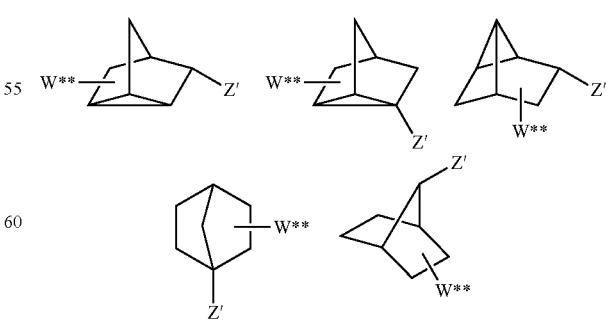

CC where Z' represents an arylol or other aromatic substituent covalently bonded as shown, and where W** is inclusive of the definition of W* and can further be one or more additional aromatic substituents which, if present, are covalently bonded to another norbornane ring carbon or to an alkyl substituent covalently bonded to another norbornane ring carbon.

In some norbornane-type arylol embodiments of the present invention each norbornane-type moiety is represented by the structure below:

where X is one of CH$_2$—CH$_2$ or O.

In some norbornane-type compound embodiments in accordance with the present invention where the norbornane compound is represented by one of structures AA, BB or any of structures CC, the groups represented by Z and Z' are independently, covalently bonded, as represented by one or more of structures A, B, C, D or E, below, where C*** represents a carbon atom of a norbornane ring and Q represents from one to five substituents independently selected from —OH, a halogen, a C$_1$ to C$_6$ alkyl group, a C$_3$ to C$_{12}$ cycloalkyl group, an aryl and an alkaryl group, n is from 0 to 4, and with the provisos that at least one of such substituents is —OH, and that the total number of such arylol substituents is an odd number:

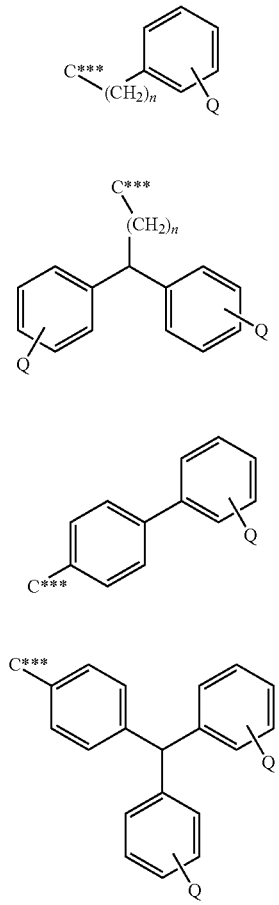

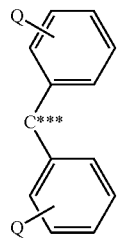

In some norbornane-type compound embodiments in accordance with the present invention where the norbornane compound is represented by structure AA, W, if not a covalent bond, is selected from one of the following structures:

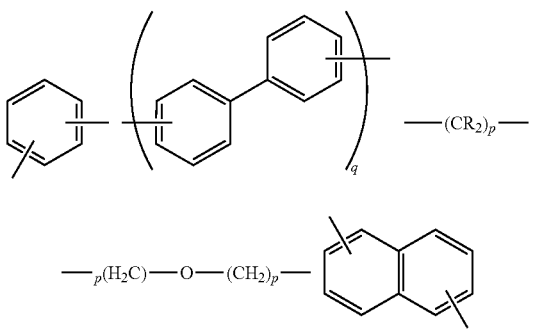

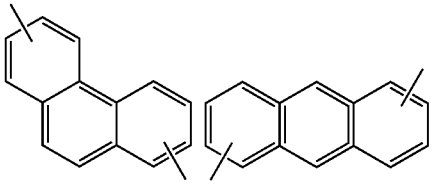

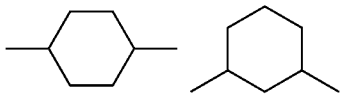

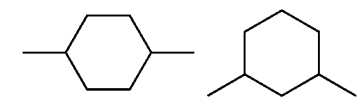

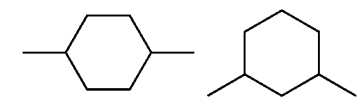

where p is an integer from 1 to 10, q is an integer from 1 to 3, y is 1 or 2, R is hydrogen or a C$_1$ to C$_4$ alkyl and A is selected from O, C(O), CH$_2$, C(CH$_3$)$_2$, C(CF$_3$)$_2$ or SO$_2$.

In some norbornane-type compound embodiments in accordance with the present invention the norbornane-type compound is selected from the following moieties:

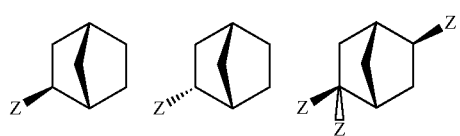
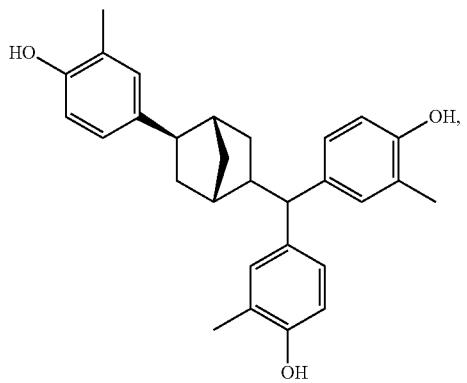
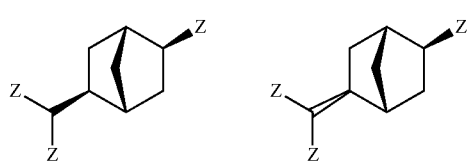
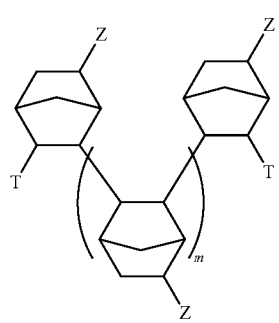
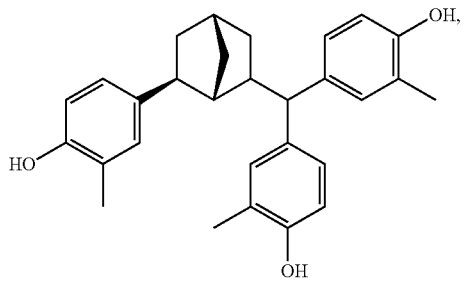
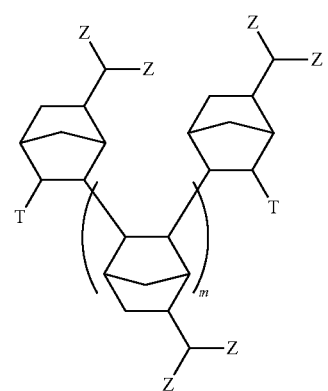
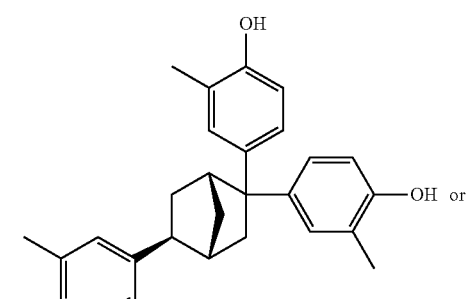
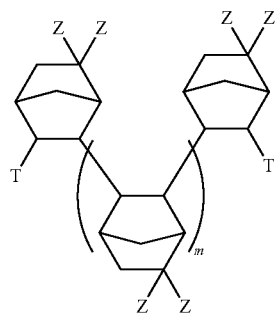
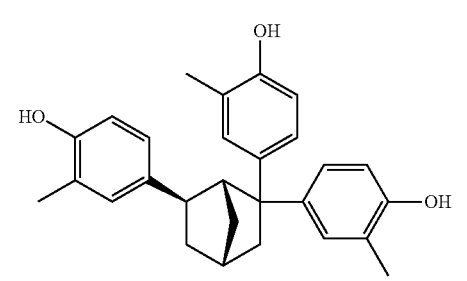
where Z is as defined above and represents either one or three substituted or unsubstituted arylol substituents, m is from 1 to 30 and T is either hydrogen or a residual from a chain transfer agent.
In still other NBane-type ballast embodiments of the present invention, such norbornane-type compound is selected from one of the following:
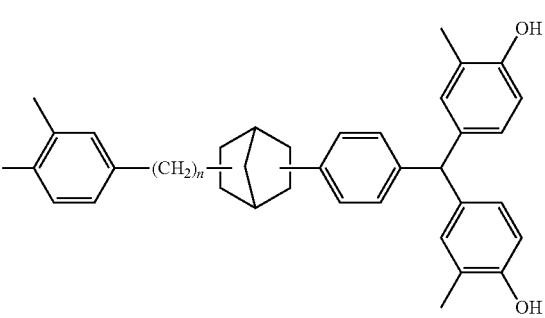

-continued

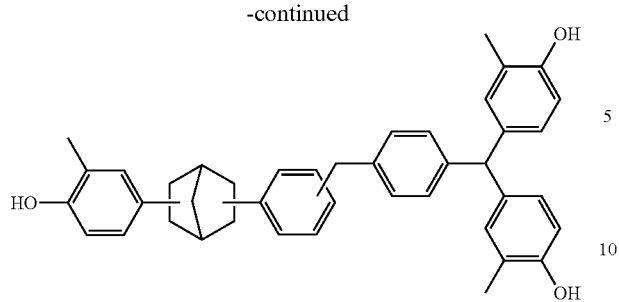

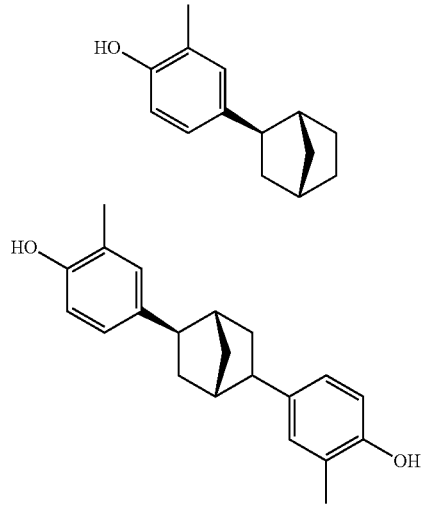

It should be realized that the NBane-type moieties in accordance with the NBane-type ballast embodiments of the present invention are, as previous described above, converted to PACs in accordance with the teachings of the aforementioned '131 patent, and that such PACs are used to form photosensitive resin composition embodiments in accordance with the present invention, where the resin component of such compositions one of a polybenzoxazole resin or a polynorbornene-type resin as are described hereinafter. Further still, it will be understood that embodiments in accordance with the present invention encompass the films and structures formed by such photosensitive resin composition embodiments where such compositions incorporate a PAC formed from a NBane-type arylol (or NBane-type ballast) as are described herein.

Exemplary PAC embodiments in accordance with the present invention will be described more fully below, but such embodiments include, but are not limited to, the following structures, where OD is either a hydroxyl group or a sulfonic acid ester:

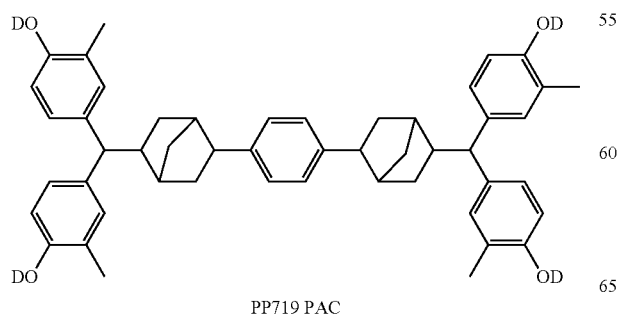

PP719 PAC

-continued

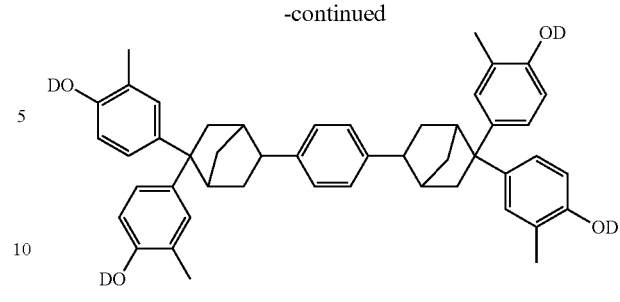

PP691 PAC

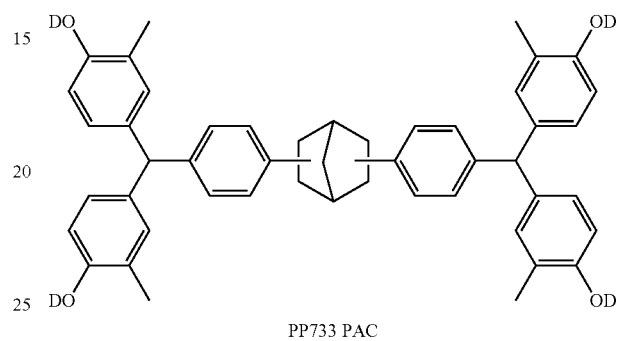

PP733 PAC

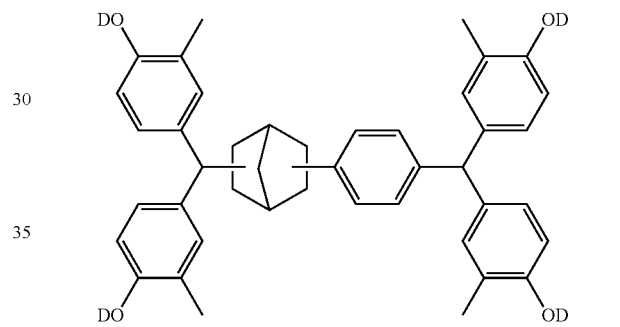

PP657 PAC

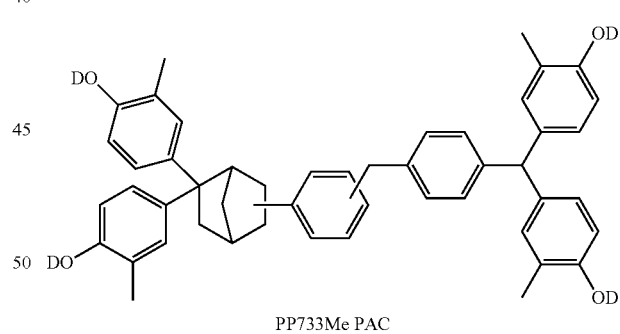

PP733Me PAC

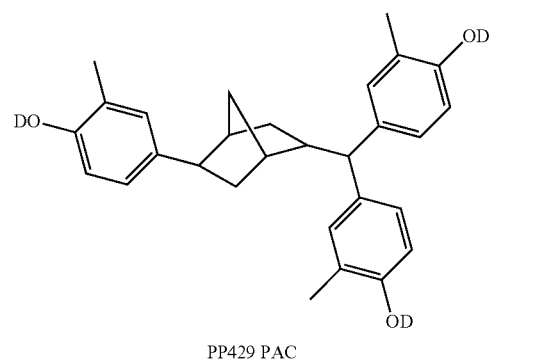

PP429 PAC

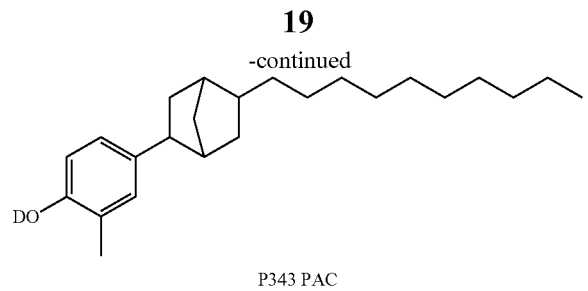

P343 PAC

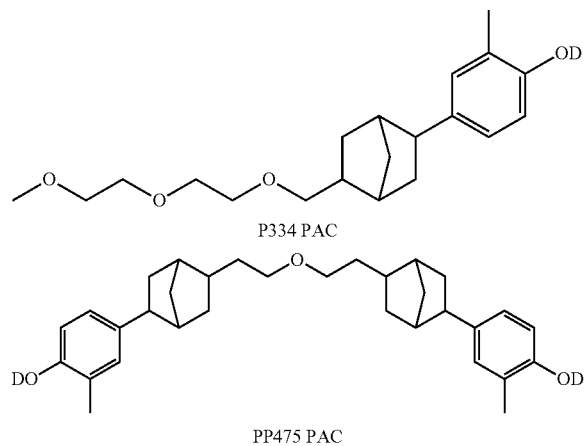

P334 PAC

PP475 PAC

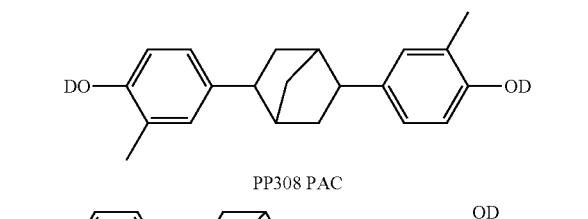

PP308 PAC

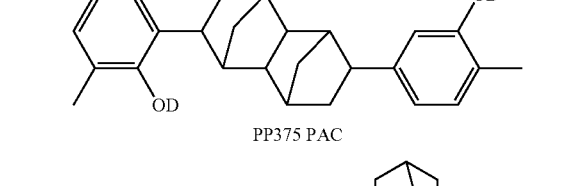

PP375 PAC

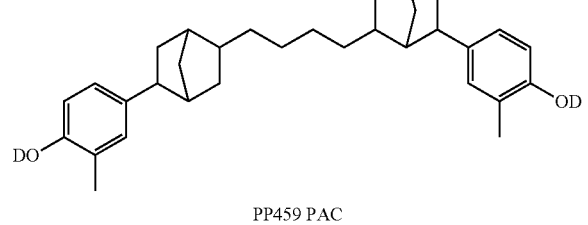

PP459 PAC

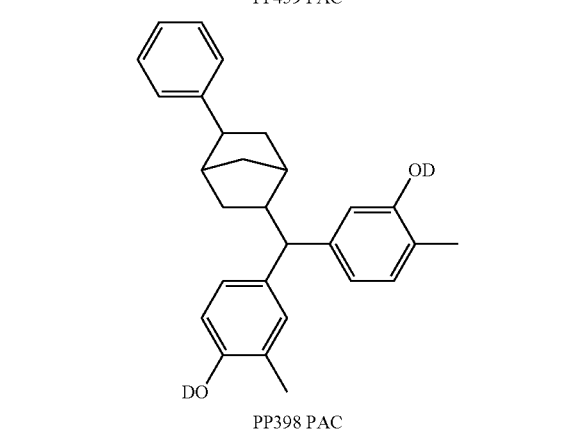

PP398 PAC

PP351 PAC

NBane-Type Ballast Precursors

Examples A and B are provided to illustrate methods useful for the preparation of NBane-type ballast Precursor moieties. Such examples are non-limiting, serving only to assist in understanding some of the embodiments in accordance with the present invention.

Example A 5,5'-(1,4-phenylene)bis(bicyclo[2.2.1]heptan-2-one)

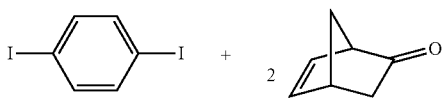

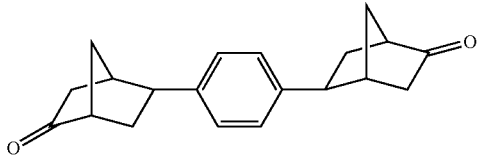

1,4-Diiodobenzene (60.0 g, 0.182 mol)), (tris-o-tolylphosphine)$_2$PdCl$_2$ (1.44 g; 1.83 mmol), and bicyclo[2.2.1]hepta-2-ene-5-one (59.3 g, 0.55 mol) were charged to an appropriately sized and equipped reaction vessel under nitrogen. DMF (600 mL) was added to this mixture. Triethylamine (152 mL, 1.09 mol) (the temperature dropped to 16° C.) and formic acid (98%) (34 mL, 0.90 mol) (the temperature rose to 34° C.) were added to this reaction mixture successively. The reaction mixture was heated slowly to 70° C. in an oil bath. The reaction initiated and the temperature of the mixture rose to 102° C. Almost immediately, the mixture turned from yellow to orange and gas evolution was observed. The reaction mixture was stirred overnight at 70° C. temperature. At the end of this reaction time, the reaction mixture was yellow and the presence of palladium metal was observed. The hot reaction mixture was filtered through a silica gel plug and a white solid formed as the filtrate cooled. This solid was collected by filtration (10.6 g). Next, about 15% of solvent was evaporated from this filtrate which caused an additional amount of product to precipitate from solution at room temperature (4.5 g). Both of the samples were 99% pure by GC (15.1 g 28% yield).

Example B

6-Phenylnorbornane-2-carboxaldehyde and 5-phenylnorbornane-2-carboxaldehyde

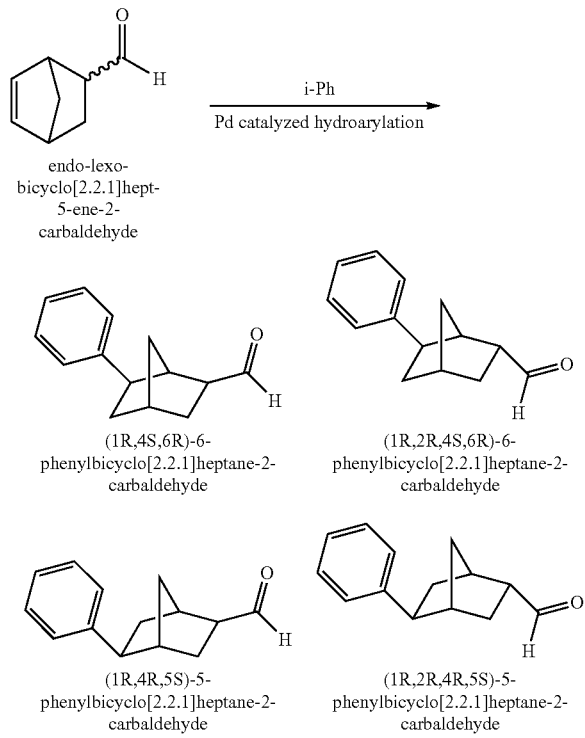

Bis(tri-o-tolylphosphine)palladium dichloride (3.9 g, 5.0 mmol)) was charged to an appropriately sized and equipped reaction vessel under nitrogen. Iodobenzene (117.5 g, 0.576 mol), endo-, exo-norbornene-2-carboxaldehyde (56.3 g, 0.46 mol), 530 ml dimethylformamide (DMF), and triethylamine (139.1 g, 1.38 mol) were added. The mixture was stirred as formic acid (53.0 g, 1.15 mol) was added dropwise within 11 minutes. The reaction temperature rose from 18° C. to 42° C. Heating was commenced. At 51° C., an exothermic reaction began. The temperature quickly climbed to 104° C. within 14 minutes while the reaction went to reflux. The reaction mixture color changed from bright yellow to orange to black. GC analysis after 20 minutes reaction time showed all norbornenecarboxaldehyde had been consumed. The reaction mixture was poured into 2500 ml distilled water. The aqueous mixture was extracted with 3×500 ml MTBE. The extracts were filtered through a Celite pad to remove palladium particles. The MTBE extracts were washed with 8×500 ml 5% aqueous LiCl to remove DMF. The MTBE solution was dried over sodium sulfate, filtered, and rotary evaporated to give 923 g brown liquid, 88.2% purity by GC analysis. NMR analysis showed four CHO signals.

The oil was dissolved in dichloromethane and adsorbed onto 120 g silica by rotary evaporation of the mixture to dryness. This was dry loaded onto on 1280 g silica and eluted with 2-2.5 L portions of solvent with a gradient starting at 100% heptane and going to 1% EtOAc/heptane. Fractions 17-25 (with 1% EtOAc/heptane) yielded 66 g oil with 96.5% (GC) purity. NMR analysis showed only three CHO signals. The oil was vacuum distilled through 10-inch glass helix-packed column. A forerun of 8.27 g with 98.6% purity was collected at 117.0-123.8° C. (1.20-130 Torr). Three fractions, totaling 50.91 g (55% yield) were collected at 112.3-118.7° C. (1.05-1.30 Torr). Purity was 99.4-99.7% by GC.

It should be understood, in view of the above experimental details and result, that the palladium catalyzed hydroarylation of singly substituted 2-norbornenes, such as the endo-/exo- 2-NBCHO above, by a haloaryl (e.g., iodobenzene) or a haloarylol (e.g., BrPhOH) leads to the four regioisomers depicted in the above reaction scheme. The addition of the phenyl group exemplified herein occurs either syn- to the exo or endo functional group or anti- to the exo- or endo-functional group, but always on the exo-face of the double bond to yield the particular regioisomers shown. Thus, hydroarylation is a useful method for generating mixtures of regioisomers having exo-aryl (or arylol) functionality in order to control the physical properties (i.e., melting point or solubility in processing solvents and formulations) of a norbornane derived phenol, polyphenol, or PAC in accordance with embodiments in accordance with the present invention.

Norbornane Ballast Synthesis

In each of Examples 1-14, provided below, a synthetic route to the named NBane-type ballast moiety is provided. It will be understood such examples are non-limiting and are provided both as illustrations of the several synthetic routes available for the preparation of NBane-type ballast moieties and to assist in the understanding of some of the embodiments in accordance with the present invention.

Example 1

4,4'-(5-(4-(5,5-bis(4-hydroxy-3-methylphenyl)bicyclo[2.2.1]heptan-2-yl)phenyl)bicyclo[2.2.1]heptane-2,2-diyl)bis(2-methylphenol) (PP691)

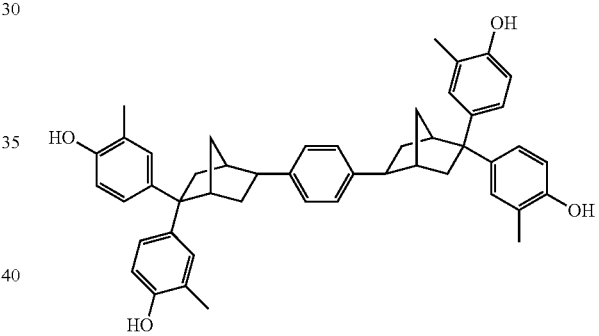

o-Cresol (200 m/e, 1.93 mol), 5,5'-(1,4-phenylene)bis(bicyclo[22.1]heptan-2-one) (15.1 g; 51.2 mmol) and dodecane-1-thiol (catalyst) (0.365 g; 1.80 mmol) were charged to an appropriately sized and equipped reaction vessel. The mixture was heated to 40° C. in an oil bath and hydrogen chloride (HCl) gas was bubbled through the reaction mixture. The reaction was continued at 40° C. for overnight (16 hours) in the presence of the HCl gas. After this time, a pink colored precipitation had formed in the vessel and the reaction was ended by stopping the flow of HCl gas. About one liter of hexanes was added to the reaction mixture and the reaction mixture filtered to yield a pink powder (~110 grams). The pink powder was extracted with toluene (500 mL) to remove o-cresol and the pink powder was then dissolved in diethyl ether and the solution was passed through a plug of silica gel. After evaporation of the diethyl ether, a red viscous oil was obtained. This material was triturated with hexanes to generate a pink precipitate which was then dissolved in methanol and extracted three times with a mixture of hexanes and heptanes. Evaporation of the methanol yielded 37 g of a solid product (light pink) that was triturated with 100 mL toluene, collected by filtration, and then dried under vacuum. The identity of the product as PP691 was confirmed by ESI-MS and proton NMR. Yield of PP691 product was 36.7 g at 95% purity.

Example 2

4,4'-((5-(4-(5-(bis(4-hydroxy-3-methylphenyl)methyl)bicyclo[2.2.1]heptan-2-yl)phenyl)bicyclo[2.2.1]heptan-2-yl)methylene)bis(2-methylphenol) (PP719)

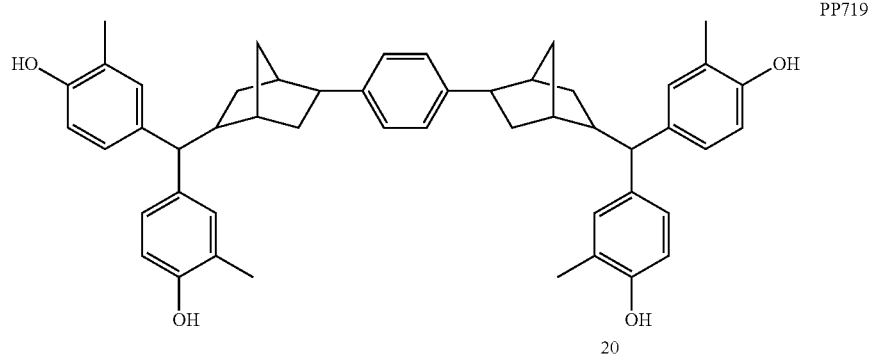

1,4-Diiodobenzene (7.51 g, 22.8 mmol), (tris-o-tolylphosphine)₂PdCl₂ (0.713 g, 0.907 mmol), 4,4'(bicyclo[2.2.1]hept-5-en-2-ylmethylene)bis(2-methylphenol) (21.8 g; 68.0 mmol) and DMF (100 mL) were weighed and charged to an appropriately sized reaction vessel equipped with stirring and a reflux condenser and placed under a nitrogen atmosphere. Triethylamine (19.0 mL, 136 mmol) and formic acid (4.40 mL, 117 mmol) were then added with stirring to this mixture. The mixture was heated to 75° C. using an oil bath. During the course of heating the mixture changed from yellow to orange and became clear. The temperature of the reaction mixture rose to 119° C. due to the exotherm of the reaction and the solution became darker, with gas evolution. The reaction mixture was allowed to stir overnight (16 hours) at 75° C. in the oil bath. The reaction mixture obtained was a clear yellow solution with black palladium particles present. The reaction mixture was diluted with ethyl acetate (100 ml) and filtered through a silica gel plug. The filtrate was washed with water and the organic layer obtained was dried over anhydrous MgSO₄. The crude mixture was purified with medium pressure column chromatography and the eluting solution was gradually changed from 100% hexanes to 100% ethyl acetate. This separation resulted in the isolation of 9.5 g of the PP719 (60% yield; 95% purity). The identity of the product was confirmed by as PP71.9 by LC-MS (ESI) and proton NMR.

Example 3

4,4'-((5-(4-hydroxy-3-methylphenyl)bicyclo[2.2.1]heptan-2-yl)methylene)bis(2-methylphenol) (PP429)

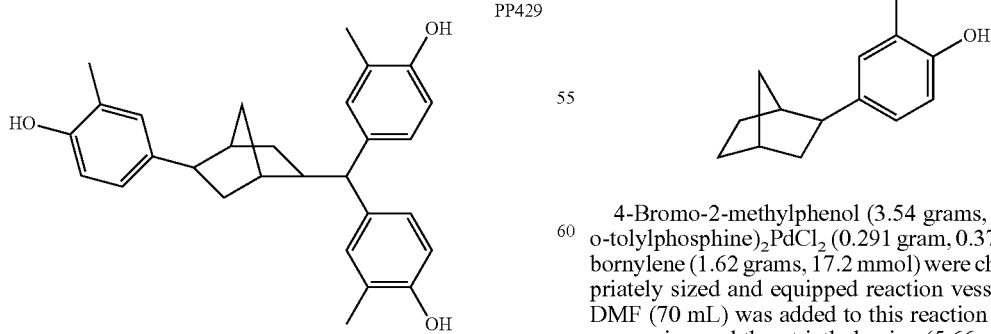

Under a nitrogen atmosphere, 4-Bromo-2-methylphenol (4.69 g, 25.1 mmol), (tris-o-tolylphosphine)₂PdCl₂ (0.377 g; 0.480 mmol), and 4,4'-(bicyclo[2.2.1]hept-5-en-2-ylmethylene)bis(2-methylphenol) (5.14 g; 16.0 mmol) were charged to an appropriately sized and equipped reaction vessel. DMF (80 mL) was added to this reactant mixture to give a suspension. Triethylamine (11.0 mL, 78.9 mmol) and formic acid (2.30 mL, 60.9 mmol) were added to this suspension and then heated to 75° C. in an oil bath. The reaction mixture turned from its original orange suspension to pale yellow and became clear. During, the course of the reaction, the temperature of the reaction mixture rose to 82° C. and turned darker, and a gas evolved very slowly. Alter the initial exothermic reaction ceased, the reaction mixture was stirred overnight at 75° C. After this time, the reaction mixture was a clear, pale yellow solution with black particles. The cooled reaction mixture was diluted with ethyl acetate (80 mL) and washed with water (160 mL) to remove DMF. The organic layer was dried over anhydrous MgSO₄. The crude mixture was purified by preparative TLC using a hexanes/ethyl acetate mixture (50:50) as developer to afford 3.7 g of 4,4'-((5-(4-hydroxy-3-methylphenyl)bicyclo[2.2.1]heptan-2-yl)methylene)-bis(2-methylphenol) (54% yield). The identity of the product as PP429 was confirmed by LC-MS (ESI) and proton NMR.

Example 4

Synthesis of 4-(bicyclo[2.2.1]heptan-2-yl)-2-methylphenol (PP202)

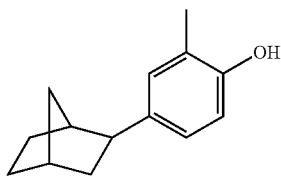

4-Bromo-2-methylphenol (3.54 grams, 19.0 mmol), (tris-o-tolylphosphine)₂PdCl₂ (0.291 gram, 0.370 mmol), and norbornylene (1.62 grams, 17.2 mmol) were charged to an appropriately sized and equipped reaction vessel under nitrogen. DMF (70 mL) was added to this reaction mixture to form a suspension and then triethylamine (5.66 grams, 56.0 mmol) and formic acid (2.20 grams, 47.7 mmol) were added. After the addition of the formic acid, the temperature of the what was observed to be a yellow suspension reaction mixture rose up to about 32° C. As the mixture was heated to 75° C. in an oil bath, the suspension turned dark at about 72° C. The reaction mixture was then allowed to stir overnight with the reaction vessel immersed in the 75° C. oil bath. After cooling the reaction mixture was a yellowish clear solution with black particles. The mixture was diluted with ethyl acetate, filtered through a silica gel plug and washed with water. The organic layer was separated and dried over anhydrous MgSO$_4$. The product solution was stripped down by rotary evaporation to afford an oil. PP202, (4-(bicyclo[2.2.1]heptan-2-yl)-2-methylphenol) was confirmed by GC-MS analysis of the crude product. (46% yield).

Example 5

4,4'-(bicyclo[2.2.1]heptane-2,5-diyl)bis(2-methylphenol) (PP308)

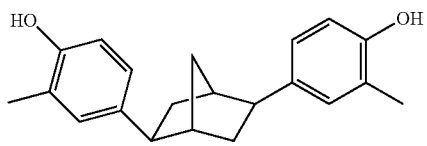

PP308-2,5

4-Bromo-2-methylphenol (2.03 grams, 10.8 mmol), (tris-o-tolylphosphine)$_2$PdCl$_2$ (0.0422 gram, 0.0537 mmol), and norbornadiene (0.257 gram, 2.79 mmol) were charged to an appropriately sized and equipped reaction vessel under nitrogen. DMF (36 mL), triethylamine and formic acid were added to what was observed to be a yellow suspension. The mixture was then heated to 75° C. in an oil bath. Upon such heating, the reaction mixture became a yellow solution, black particles appeared and a very slow evolution of gas was observed. The reaction mixture was stirred overnight at this temperature. After cooling, the reaction mixture was diluted with ethyl acetate and washed with water. The organic layer was separated and dried over anhydrous MgSO$_4$. PP308-2,5, (4,4'-(Bicyclo[2.2.1]heptane-2,5-diyl)bis(2-methylphenol)) was confirmed by GC-MS of the crude product (43% yield).

Example 6

4-((3-hydroxy-4-methylphenyl)(5-penylbicyclo[2.2.1]heptan-2-yl)methyl)-2-methylphenol (PP398)

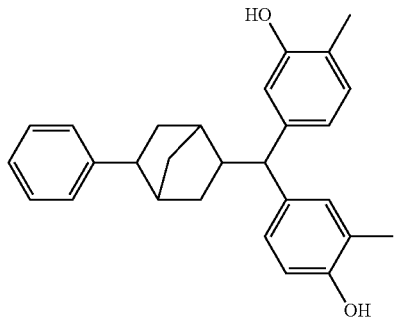

PP398

A mixture of endo-, exo-6-Phenylnorbornane-2-carboxaldehyde and endo-, exo-5-phenylnorbornane-2-carboxaldehyde 39.87 g, 0.20 mol) were charged to an appropriately sized and equipped reaction vessel. o-Cresol (275 g, 2.54 mol) was added and the vessel heated in a 75° C. oil bath. When the reaction mixture reached 25° C., 1-dodecanethiol (4.8 ml) was syringed into the reaction mixture and when the temperature of the mixture reached 50° C., HCl gas slowly bubbled into the reaction mixture. The mixture immediately became pink-colored and then warmed to about 75° C. within 10 minutes, at which time an aliquot was removed and analyzed by HPLC. The analysis indicated that all of the aldehydes had been consumed. The HCl addition and heating were stopped. A total of 1.8 g HCl had been added.

The reaction mixture was then poured into 1000 ml of distilled water and the resulting phases separated. The aqueous phase was extracted with 500 ml dichloromethane and the organic portions were combined and washed with 500 ml portions of brine to pH 7. After drying over sodium sulfate, the organic solution was filtered and the solvents removed by rotary evaporation to obtain 307.2 g of an oil. HPLC analysis showed 82.4% o-cresol and 15.1% PP398. The oil was rotary evaporated at 0.87-1.05 Torr and 65-75° C. to remove 197 g o-cresol and leave 100.3 g of a light violet syrup. HPLC analysis found 32.2% o-cresol, 64.1% PP398 isomers, and 3.3% higher retention time byproducts. Further rotary evaporation under high vacuum removed about 3 g of residual o-cresol.

The syrup was dissolved in dichloromethane to which 253 g silica was added. The resulting slurry was then rotary evaporated to dryness. The dried silica was then dry loaded onto 1240 g of silica and eluted with a solvent gradient commencing with 100% heptane and going to 100% dichloromethane. With 50:50 dichloromethane/heptane, o-cresol was removed. At 100% dichloromethane, the following combined fractions were obtained:

| 1 | 18.44 g | white crystals | 95.6% | 3 isomers | |
|---|---|---|---|---|---|
| 2 | 57.70 g | white crystals | 99.3% | 3 isomers | 73% yield |
| 3 | 0.65 g | white powder | 97.2% | 3 isomers | |

Fraction 2 was taken as pure product. Fractions 1 and 3 were combined with 18 g of 95.9-97.5% purity material from an earlier run and eluted with a heptane/dichloromethane gradient through 800 g silica. This yielded an additional 5.74 g of 99.1% PP398 isomers.

Example 7

4,4'-(bicyclo[2.2.1]heptane-2,2-diyl)bis(2-methylphenol

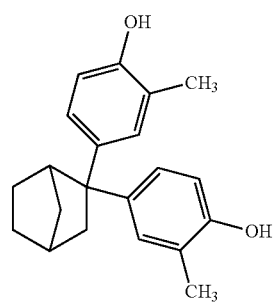

PP308-2,2

An appropriately sized and equipped reaction vessel was charged with o-cresol (44 g, 0.406 mol) in 10 mL MeOH and 1-dodecanethiol (1.09 mL, 0.0045 mol). The mixture was heated to 40° C. and the addition funnel was charged with 2-norbornanone (5 g, 0.045 mol) in 5 mL MeOH and o-cresol (5 g, 0.046 mol) in 5 mL MeOH. The o-cresol solution was added dropwise at 40° C. over 45 min, while introducing HCl gas under stirring. After addition, the HCl gas was bubbled for another 45 min and white precipitate was observed and color turns to light pink from dark orange. The reaction mixture was stirred for another 17 h at 40° C., GC analysis showed no starting material 2-norborbornanone. The mixture was cooled to room temperature and removed MeOH using rotary evaporator and diluted with 50 mL $CH_2Cl_2$. Filter the white precipitate and washed with (3×50 mL) $CH_2Cl_2$ and dried under vacuum for 6 h gave 10.5 g (75% yield) of product as white solid with >99.9% purity by HPLC. $^1$H-NMR, $^{13}$CNMR and MS were consistent with the structure.

Example 8

2-methyl-4-{6-{[2-(2 methoxyethoxy)-ethoxy]methyl}bicyclo[2.2.1]heptan-2-yl}phenol

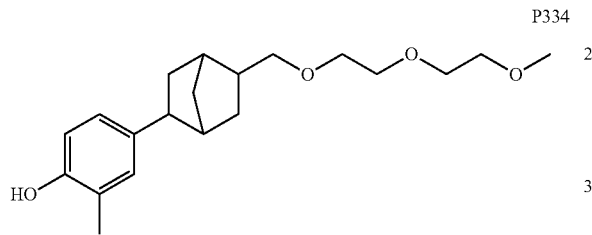

P334

An appropriately sized and equipped reaction vessel was charged with 9.13 g 4-iodo-2-methylphenol (IMePhOH, 0.039 mol), 8.83 g 5-[2-(2-methoxyethoxy)ethoxy]methyl}bicyclo[2.2.1]hept-2-ene (TONNB) (0.039 mol), 0.27 g Pd(Ph$_3$P)$_2$Cl$_2$ (3.9 mmol, 1 mol %), 11.82 g triethylamine (0.117 mol), and 60 ml dimethylformamide (DMF). The mixture was magnetically stirred to give an orange-brown slurry. Formic acid (4.49 g, 0.0975 mol) was added quickly by pipette. The temperature rose from 19° C. to 34° C. and the reaction mixture became a light orange solution. External heating was started. After 15 minutes and at 70° C., GC analysis showed 35.1% IMePhOH, 63.1% TONNB, and 1.5% total of 4 isomers of P334 (TONNB-cresol). At 70° C., an exotherm caused the reaction temperature to rise to 82° C. with evolution of $CO_2$ and the solution became bright yellow. After approximately two hours, the reaction mixture had become olive and black Pd particles had precipitated. GC analysis showed no IMePhOH, 1.5% TONNB, and 94.2% P334 (4 isomers). The reaction mixture was then cooled to 34° C., but then reheated up to 82° C. for 24 min to ensure that all IMePhOH had been consumed. The reaction was cooled to 70° C., filtered through Celite® filtering aid to remove the Pd particles, and rinsed with ~50 ml MTBE. The filtrate was treated with 100 ml distilled water and then acidified with 10 ml 3.5N HCl to bring the pH to 5. The phases were separated and the aqueous phase extracted with 3×50 ml MTBE. The MTBE washings and organic portions were combined and washed with 3×40 ml 5% aqueous LiBr. The LiBr washes gave pH from 3 to 2. The organic phase was washed with 50 ml brine until a pH of 3 was obtained and then dried over sodium sulfate, filtered, and solvent removed by rotary evaporation to yield 12.4 g of a light brown oil. GC analysis found 1.2% TONNB and 96.1% P334 having an isomer ratio of 34:12:44:10.

The P334 was dissolved in heptane and dichloromethane, mixed with 38 g silica, and solvents removed rotary evaporation until a dry powder was obtained. The powder was loaded onto 320 g silica and elution was started using 100% heptane. TONNB and other significant impurities were eluted with the solvent gradient between 100% heptane to 20% EtOAc/heptane. TONNB-cresol eluted with 30% EtOAc/heptane to give 10.2 g (78% yield) colorless oil. GC analysis gave 100% purity. Isomer ratio was 35:12:43:10. Data: GC analysis done on a DB5 column: 30 m, 0.32 mm ID, 0.25 µm film. Gradient: 75° C. to 200° C. @ 15° C./min., then heat @ 40° C./min to 300° C. Injector: 250° C. Detector: 350° C. (FID), Retention time: 8.244 min (IMePhOH), 9.199 min (TONNB), 14.036 min, 14.209 min, 14.555 min, 14.465 min. (TONNB-cresol isomers). TLC analysis on silica gel with 50% EtOAc/heptane.

Example 9

2-methyl-4-{6-nonylbicyclo[2.2.1]heptan-2-yl}phenol (P343)

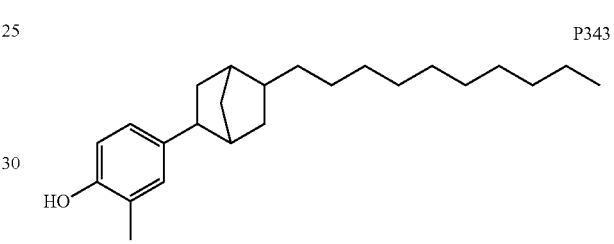

P343

An appropriately sized and equipped reaction vessel was charged with 11.70 g 4-iodo-2-methylphenol (IMePhOH, 0.05 mol), 11.70 g 2-decylnorbornene (DecNB, 0.05 mol), 0.35 g Pd(Ph$_3$P)$_2$Cl$_2$ (5 mmol, 1 mol %), 15.15 g triethylamine (0.15 mol), and 58 ml dimethylformamide. The mixture was magnetically stirred to give a tan slurry and formic acid (5.75 g, 0.125 mol) was added quickly by pipette. The temperature rose from 21° C. to 37° C. and the reaction mixture became an orange solution. External heating was applied. At 56° C., an exotherm commenced, causing the temperature to rise to 67° C. with evolution of $CO_2$ and the solution became yellow. After approximately 7 hours at 70° C., a sample quench (about 0.5 ml of reaction mixture into 1 ml water) was analyzed to show ~0% IMePhOH, 3.9% DecNB, and 92.5% P343 (4 isomers). The reaction mixture was cooled to 47° C., filtered through Celite® filtering aid to remove the Pd particles, and rinsed with ~50 ml MTBE. The filtrate was treated with 100 ml distilled water and then acidified with 10 ml 3.5N HCl to pH 4. The phases were separated and the aqueous phase extracted with 4×30 ml MTBE. The MTBE and organic portions were combined and washed with 3×40 ml 5% aqueous LiBr. The LiBr washes gave pH=10. The organic phase was then dried over sodium sulfate overnight, filtered, and the solvent removed by rotary evaporation to yield 16.32 g oil. GC analysis found 4.2% DecNB and 89.2% P343 with an isomer ratio of 28:12:48:12.

The P343 was then dissolved in heptane, mixed with 35 g silica, and the slurry rotary evaporated to a dry powder. The powder was loaded onto 381 g silica and the P343 eluted with first 100% heptane and then mixtures of EtOAc/heptane. The several fractions where combined in pentane and then the solvent removed by rotary evaporation to give 9.83 g (57%) of 99.7% P343 with an isomer ratio of 33:13:44:10.

Example 10

4,4'-((oxybis(ethane-2,1-diyl))bis(bicyclo[2.2.1]heptane-5,2-diyl))bis(2-methylphenol) (PP 475)

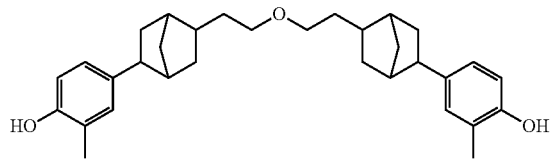

PP475

An appropriately sized and equipped reaction vessel was charged with 4-iodo-2-methylphenol (75.7 g, 323 mmol) in 380 mL DMF. To that was added Pd(PPh$_3$)$_4$ (3.56 g, 3.08 mmol) at room temperature giving a light yellow solution. Then, 5,5'-(oxybis(ethane-2,1-diyl))bis(bicyclo[2.2.1]hept-2-ene) (39.8 g, 154 mmol), 100 ml dimethylformamide (DMF), and triethylamine (65 mL, 462 mmol) were added and the mixture stirred as formic acid (17.7 g, 14.5 mL 385 mmol) was added drop wise within 5 minutes. The reaction temperature rose from 20° C. to 25° C. after which external heating was applied. At 70° C., an exothermic reaction began and the temperature quickly climbed to 82° C. within 10 minutes accompanied by color changes from light yellow to orange to black. The reaction was monitored by GC and after stirring at 75° C. for 96 h an aliquot GC indicated the reaction was complete. The reaction mixture was allowed to cool to room temperature and was poured into 2000 mL distilled water. The aqueous mixture was extracted with (3×1500 mL) MTBE, the extracts were filtered through a Celite® filtering aid pad to remove palladium particles and then washed with (2×1 L) water, (2×1 L) brine and (2×1 L) 5% aqueous LiCl to remove residual DMF. The resulting MTBE solution was dried over sodium sulfate, filtered, and the solvent rotary evaporated to give 94 g of a brown liquid. The 94 g of crude PP475 was adsorbed onto 120 g silica and chromatographed over an additional 1 kg of silica eluting with heptane-EtOAc mixtures. The concentrated purified fractions yielded 43 g (59% yield) of PP475 as a clear viscous oil with >98.0% purity by NMR. NMR and MS were consistent with the desired structure.

Example 11

4-((3-hydroxy-4 methylphenyl)(5-phenylbicyclo[2.2.1]heptan-2-yl)methyl)-2-methylphenol (PP400)

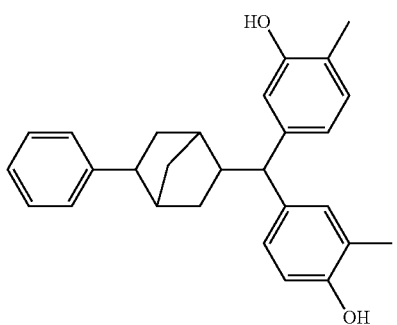

PP400

PhNBaneCHO

Bis(tri-o-tolylphosphine)palladium chloride (3.9 g, 5.0 mmol)) was charged to an appropriately sized and equipped reaction vessel. Iodobenzene (117.5 g, 0.576 mol), endo-/exo-norbornene-2-carboxaldehyde (56.3 g, 0.46 mol), 530 ml dimethylformamide (DMF), and triethylamine (139.1 g, 1.38 mol) were added and the mixture stirred as formic acid (53.0 g, 1.15 mol) was added drop wise over 11 minutes. The reaction temperature rose from 18° C. to 42° C. after which external heating was applied. At 51° C., an exothermic reaction began and the temperature rose to 104° C. within 14 minutes while the reaction went to reflux. The reaction mixture color changed from bright yellow to orange to black during reflux and a GC analysis of an aliquot taken after 20 minutes reaction time showed all norbornenecarboxaldehyde had been consumed. The reaction mixture was poured into 2500 ml distilled water and the aqueous mixture was extracted with (3×500 ml) methyl-tert-butyl ether (MTBE). The extracts were filtered through a Celite® filtering aid pad to remove palladium particles and the extracts washed with (8×500 ml) 5% aqueous LiCl to remove residual DMF. The MTBE phase was separated and then dried over sodium sulfate, filtered, and rotary evaporated to give 92.3 g of a brown liquid, 88.2% purity by GC analysis. NMR analysis showed four CHO signals.

The oil was dissolved in dichloromethane and adsorbed onto 120 g silica by rotary evaporation of the mixture to dryness. This was dry loaded onto 1280 g silica and eluted with 2-2.5 L portions of solvent with a gradient starting at 100% heptane and going to 1% EtOAc/heptane. Fractions 17-25 (with 1% EtOAc/heptane) yielded 66 g oil with 96.5% (GC) purity. NMR analysis showed only three CHO signals. The oil was vacuum distilled through 10-inch glass helix-packed column. A forerun of 8.27 g with 98.6% purity was collected at 117-124° C. (1.20-1.30 Torr). Three fractions, totaling 50.91 g (55% yield) were collected at 1129-119° C. (1.05-1.30 Torr). Purity was 99.4-99.7% by GC. Data: GC analysis done on a EC5 column: 30 m, 0.32 mm ID, 0.25 µm film. Gradient: 75° C. to 200° C. @ 15° C./min., then heat @ 40° C./min to 300° C. Injector: 250° C. Detector: 350° C. (FID), Retention time: 10.450 and 10.646 minutes.

PhNBaneCH(CH$_2$-2,5-Me$_2$-OH)$_2$

An appropriately sized and equipped reaction vessel was charged with 2,5-dimethylphenol (22.6 g, 185 mmol) in 45 mL MeOH and 1-dodecanethiol (1.3 mL, 5.5 mmol). A slight endotherm was observed (18° C. to 5° C.). An addition funnel was charged with Ph-NBaneCHO (11 g, 54.9 mmol) in 10 mL MeOH-1 and 2,5-dimethylphenol (11 g, 90 mmol) in 10 mL MeOH and then the solution was added drop wise over a 30 minute period, while introducing HCl gas under stirring. During the addition, the reaction temperature rose to 50° C. After addition, the HCl gas was bubbled for another 1 h and the reaction mixture turned from clear to light blue. The reaction mixture was stirred for another 3 h at 50° C., GC analysis showed no starting material Ph-NBaneCHO. The mixture was cooled to room temperature and MeOH was removed under rotavap to give a blue oil. The crude blue oil was dissolved in 200 mL EtOAc and washed with water and brine. The organic phase was dried over sodium sulfate, filtered and concentrated to give 48 g crude product as a blue oil. The 48 g crude product was further purified via Kugelrohr distillation (100-120° C. oven temperature, 0.1-0.4 Torr high vacuum) to give 31.3 g product as a light blue solid. The 31.3 g material was triturated with 100 mL DCM and filtered to give 7.5 g (32% yield) product with 99.7% purity by HPLC. The filtrates were concentrated and gave an additional 26.1 g of crude product which was also subjected to Kugelrohr distillation (110-150° C. Oven temperature, 0.6-0.8 Torr high vacuum) to give 19.3 g product as an off-white solid. The 19.3 g of crude product was adsorbed onto 20 g of silica and chromatographed over and additional 120 g of silica eluting with heptane/EtOAc mixtures. The concentrated purified fractions yielded 12.2 g (52% yield) of product as an off-white powder with >99.9% purity by HPLC. The combined yield for this reaction was 84%. NMR and MS were consistent with the structure.

Example 12

3-(bicyclo[2.2.1]heptan-2-yl(4-hydroxy-2,5-dimethylphenyl)methyl)-2,5-dimethylphenol (PP350)

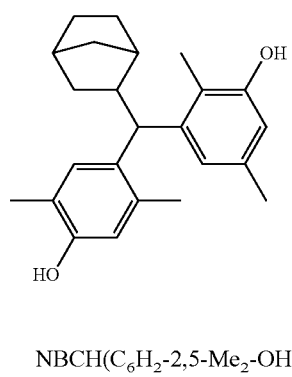

PP350

NBCH($C_6H_2$-2,5-$Me_2$-OH)$_2$

An appropriately sized and equipped reaction vessel was charged with KOH (4.6 g, 81.8 mmol) in 50 mL MeOH. The mixture was heated to 65-66° C. and 2,5-dimethylphenol (20 g, 163.7 mmol) dissolved in 20 mL MeOH was added at 66° C. An addition funnel was then charged with exo-/endo-NBCHO (10 g, 81.8 mmol) in 10 mL MeOH. After slow addition of the NBCHO solution the reaction mixture was refluxed and monitored by TLC and 1-HPLC. No significant exotherm was observed during addition of aldehyde solution and the color of the reaction mixture change from light yellow to dark brown. The reaction was monitored periodically by taking an aliquot and quenching with 1N HCl solution and extracting with EtOAc and checking TLC/HPLC. After 7 days reflux all aldehyde was consumed, but, unreacted phenol was observed by TLC/HPLC and crude LCMS indicated >89% product with ~10% unreacted phenol. The reaction mixture was allowed to cool to room temperature and acidified with 4N HCl and diluted with 200 mL $CH_2Cl_2$. A KCL precipitate was filtered and the filtrate concentrated to give 33.5 g crude product as a brown paste. The 33.5 g crude product was dissolved in 500 mL EtOAc and washed with water, brine, dried over $Na_2SO_4$, filtered and concentrated to give 32.7 g crude product.

The 32.7 g of crude product was adsorbed onto 33 g silica and chromatographed over an additional 330 g of silica eluting with heptane (1 L), 5% EtOAc in heptane (8 L), 7% EtOAc in heptane (10 L), 10% EtOAc in heptane (6 L), 12% EtOAc in heptane (4 L), 15% EtOAc in heptane (2 L) and 20% EtOAc in heptane (2 L). The concentrated purified fractions yielded 13.2 g of product as a light yellow solid, which was further purified by recrystallization from hot toluene to give 10.7 g (37.5% yield) product with 98.7% purity by HPLC. NMR and MS were consistent with the desired structure.

NBaneCH($C_6H_2$-2,5-$Me_2$-OH)$_2$

A 250 mL glass Parr pressure bottle was charged with 10.7 g (30.7 mmol) of NBCH($C_6H_2$-2,5-$Me_2$-OH)$_2$ in 60 mL EtOAc. Then 654 mg (0.307 mmol) 10% Pd/C (50% wet) was added under $N_2$ blanket. The reaction mixture was flushed with $N_2$ two times and charged with $H_2$ at 35 psi and agitated on the Parr shaker for 3 h at room temperature. The reaction mixture was flushed with $N_2$ and filtered through a pad of Celite and $MgSO_4$. The filtrate was concentrated and dried under high vacuum to give 10.65 g (98.9% yield) product as a white powder with 99.4% purity by HPLC. MS and NMR were consistent with the desired structure. The melting point of the product was 192-194° C.

Example 13

4-(5-(4-(6-(4-hydroxy-3-methylphenyl)bicyclo[2.2.1]heptan-2-yl)butyl)bicyclo[2.2.1]heptan-2-yl)-2-methylphenol)

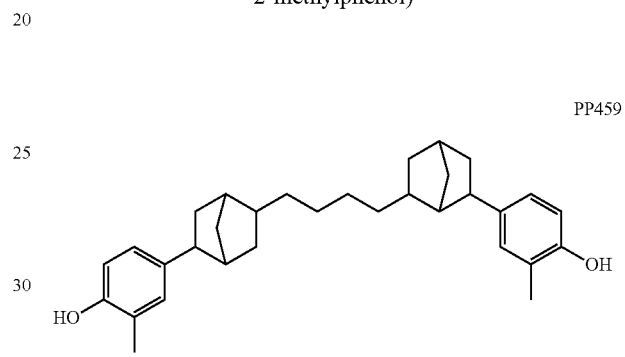

PP459

An appropriately sized and equipped reaction vessel was charged with 4-iodo-2-methylphenol (10.14 g, 43.3 mmol) in 40 mL DMF under nitrogen and then Pd(PPh$_3$)$_4$ (477 mg, 0.412 mmol) was added at room temperature giving a light yellow solution. Then, NB(CH$_2$)$_4$NB (5 g, 20.6 mmol), 25 ml dimethylformamide (DMF), and triethylamine (10 mL, 72.2 mmol) were added. The mixture was stirred as formic acid (2.37 g, 1.94 mL 51.6 mmol) was added dropwise over 5 minutes. The reaction temperature rose from 20° C. to 25° C. after which external heating was applied. At 70° C., an exothermic reaction began and the temperature climbed to 85° C. within 10 minutes. The reaction mixture changed color from light yellow to orange to black. The reaction was monitored by GC and after stirring at 75° C. for 72 h an aliquot analyzed by GC indicated the reaction was complete.

The reaction mixture was allowed to cool to room temperature and was poured into 100 mL, distilled water. The aqueous mixture was extracted with (3×300 mL) MTBE and the combined extracts were filtered through a Celite pad to remove palladium particles. The extracts were then washed with water, brine and 5% aqueous LiCl to remove residual DMF. The MTBE solution was then dried over sodium sulfate, filtered, and rotary evaporated to give 13.1 g of a brown liquid. The 13.1 g of crude product was adsorbed onto 13 g of silica and chromatographed over an additional 130 g of silica eluting with heptane/EtOAc mixtures. The concentrated purified fractions yielded 4.6 g (49% yield) of product as a clear viscous oil with >98.0% purity by NMR. NMR and MS were consistent with the desired structure.

Example 14

5-(6-(2-hydroxy-3-methylphenyl)decahydro-1,4:5,8-dimethanonaphthalen-2-yl)-2-methylphenol

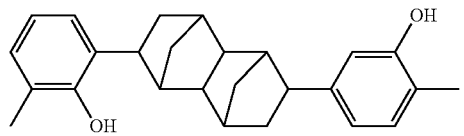

PP375

An appropriately sized and equipped reaction vessel was charged with 4-bromo-2-methylphenol (2.5 g, 13.2 mmol) in 13 mL DMF and then Pd(P(o-tolyl)$_3$)$_2$)Cl$_2$ (110.3 mg, 0.12 mmol) was added at room temperature giving a light yellow solution. Then, TDD (1 g, 6.3 mmol), 6 ml dimethylformamide (DMF), and triethylamine (2.65 mL, 18.95 mmol) were added. The mixture was stirred as formic acid (727 mg, 0.6 mL 15.8 mmol) was added dropwise over 5 minutes. The reaction temperature rose from 20° C. to 25° C. after which external heating was applied. At 70° C., an exothermic reaction began. The temperature rose to 80° C. within 10 minutes and the reaction mixture changed color from light yellow to orange to brown. The reaction was monitored by GC and after stirring at 75° C. for 96 h an aliquot analyzed by GC indicated the reaction was complete.

The reaction mixture was allowed to cool to room temperature and was poured into 50 mL distilled water. The aqueous mixture was extracted with MTBE and the combined extracts filtered through a Celite pad to remove palladium particles. The MTBE extracts were then washed with water, brine and 5% aqueous LiCl to remove residual DMF. The MTBE solution was then dried over sodium sulfate, filtered, and rotary evaporated to give 2 g of a brown liquid. The 2 g of crude product was adsorbed onto 2 g of silica and chromatographed over an additional 20 g of silica eluting with pentane/EtOAc mixtures. The concentrated purified fractions yielded 600 mg (25% yield) of product as a clear viscous oil with >98% purity by NMR. NMR and MS were consistent with the desired structure.

PAC Synthesis

As previously mentioned, the NBane-type PAC material embodiments in accordance with the present invention are prepared by converting an analogous NBane-type arylol moiety to the PAC form by reaction the arylol with one of the following sulfonic acids or their respective acid chlorides: 1,2-naphthoquinone-2-diazido-5-sulfonic acid, 1,2-naphthoquinone-2-diazido-4-sulfonic acid or 2-diazo-4-hydrosulfonylcyclohex-3-enone, the structures of which are shown, respectively below, to form the esters thereof:

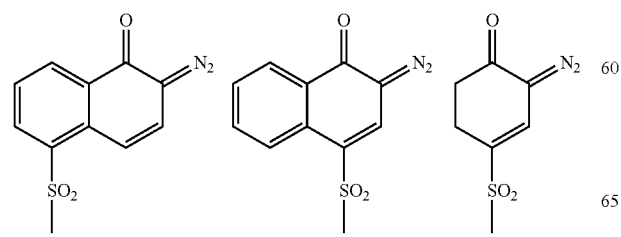

While generally a particular level of DNQ substitution is targeted for such conversions, the selection of reagents and reaction conditions, as illustrated in PAC formation examples below.

Example PAC-1 (Q-1)

PP691 PAC 88% Targeted Substitution

An appropriately sized and equipped reaction vessel was charged with 4.75 g (0.0069 mol) of PP691 and 6.50 g (0.024 mol) of 1,2-naphoquinone-diazide-4-sulfonylchloride and 63.75 g of acetone. The mixture was stirred to produce a uniform solution and cooled to room temperature with continued stirring. Next, a mixture of triethylamine/acetone (2.69 g, 0.027 mol of triethylamine) was added slowly to the solution while maintaining the temperature at less than 35° C. The reaction mixture was stirred for an additional 3 h after the addition of the triethylamine after which 0.36 g (0.006 mol) of acetic acid was added to quench the reaction. After stirring the mixture for an additional 30 min., the mixture was filtered and the filtrate added to a mixture of acetone/water (4 g/358 g) and this mixture allowed to stir for an additional 1 h. The resulting precipitate was collected by filtration, washed with water and then dried under vacuum. 8.11 g of PAC shown by the following formula, an 81.3% yield, was obtained (PAC-1). It was found that the PAC was 13% diester, 30% trimester and 42% tetraester by HPLC analysis. It was found that the resulted photosensitizer comprised of 15% of monoester, 43% of diester and 36% of triester by high performance liquid chromatography analysis. Analysis by $^1$H-NMR indicated the expected structure.

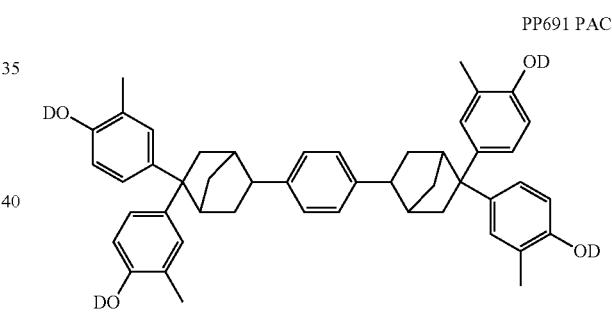

PP691 PAC wherein D represents a hydrogen atom or a group shown by the following formula of which the percentage by the weight of D is 72%, with the balance being a hydrogen atom.

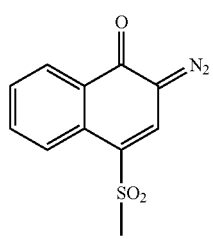

Example PAC-2 (Q-2)

PP429 PAC 88% Targeted Substitution

An appropriately sized and equipped reaction vessel was charged with 2.82 g (0.0066 mol) of PP429, 4.68 g (0.0174 mol) 1,2-naphthoquinone-diazide-4-sulfonylchloride and 42.50 g of acetone. After stirring the mixture to a uniform solution, the reaction solution was cooled by the water bath at room temperature. Then, a mixture of triethylamine/acetone (1.94 g (0.0191 mol)/1.37 g) was slowly added dropwise while maintaining the temperature at less than 35° C. After stirring for three hours at room temperature, 0.26 g (0.0044 mol) of acetic acid was added to the reaction mixture to neutralize. After stirring for 30 minutes further, the reaction mixture was filtered and poured into a mixture of pure water/acetic acid (241 g/2 g). After stirring for 1 hour, the resulting precipitate was collected, sufficiently washed with pure water and dried under vacuum. 5.61 g of a photosensitizer (PAC), shown by the following formula, was obtained (yield: 85.1%, PAC-2). It was found that the resulted photosensitizer comprised of 47% of diester and 31% of triester by HPLC analysis. Analysis by 1H-NMR indicated the expected structure.

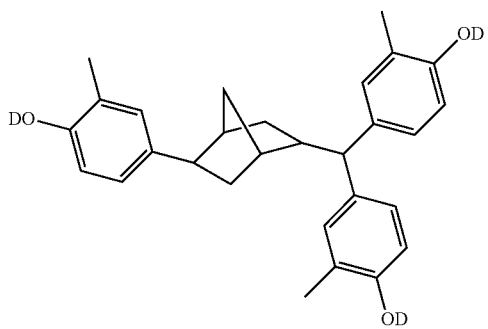

PP429 PAC wherein D represents a hydrogen atom or the group shown in Example PAC1 of which the percentage by the weight of D is 68%, with the balance being a hydrogen atom.

Example PAC-3 (Q-3)

PP398 88% Substitution Target

An appropriately sized and equipped reaction vessel was charged with 4.50 g (0.0113 mol) of PP398, 5.35 g (0.0199 mol) 1,2-naphthoquinone-diazide-4-sulfonylchloride and 55.79 g of acetone. After stirring the mixture to a uniform solution, the reaction solution was cooled by the water bath at room temperature. Then, a mixture of triethylamine/acetone (2.22 g (0.0219 mol)/2.17 g) was slowly added dropwise while maintaining the temperature at less than 35° C. After stirring for three hours at room temperature, 0.30 g (0.0050 mol) of acetic acid was added to the reaction mixture to neutralize. After stirring for 30 minutes further, the reaction mixture was filtered and poured into a mixture of pure water/acetic acid (313 g/3 g). After stirring for 1 hour, the resulting precipitate was collected, sufficiently washed with pure water and dried under vacuum. 5.24 g of a photosensitizer (PAC), shown by the following formula, was obtained (yield: 64.7%, PAC-3). It was found that the resulted photosensitizer comprised of 22% of diester and 75% of triester by HPLC analysis. Analysis by $^1$H-NMR indicated the expected structure.

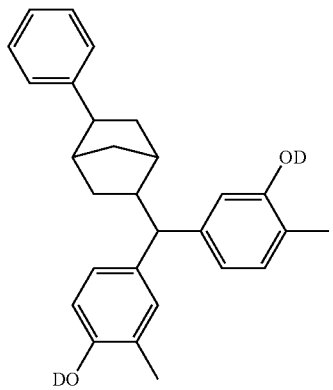

PP398 PAC wherein D represents a hydrogen atom or the group shown in Example PAC1 of which the percentage by the weight of D is 86%, with the balance being a hydrogen atom.

Example PAC4

TrisP-PA 88% Substitution Target

An appropriately sized and equipped reaction vessel was charged with 4.19 g (0.010 mol) of TrisP-PA (Honshu Chemical Industry co.), 7.01 g (0.026 mol) 1,2-naphthoquinone-diazide-4-sulfonylchloride and 63.46 g of acetone. After stirring the mixture to a uniform solution, the reaction solution was cooled by the water bath at room temperature. Then, a mixture of triethylamine/acetone (2.90 g (0.029 mol)/2.04 g) was slowly added dropwise while maintaining the temperature at less than 35 degree C. After stirring for three hours at room temperature, 0.39 g (0.007 mol) of acetic acid was added to the reaction mixture to neutralize. After stirring for 30 minutes further, the reaction mixture was filtered and poured into a mixture of pure water/acetic acid (360 g/4 g). After stirring for 1 hour, the resulting precipitate was collected, sufficiently washed with pure water and dried under vacuum. 8.95 g of a diazoquinone compound shown by the following formula (PAC-4) was obtained (yield: 91.0%). It was found that the resulted photosensitizer comprised of 15% of monoester, 43% of diester and 36% of triester by high performance liquid chromatography analysis. Analysis by $^1$H-NMR indicated the expected structure.

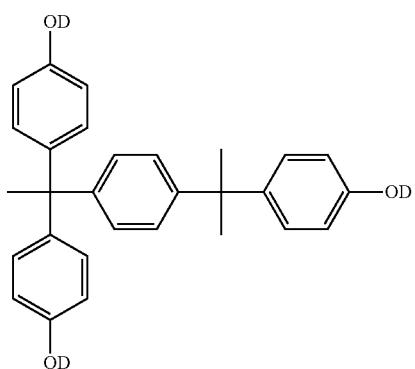

Tris-P wherein D represents a hydrogen atom or the group shown in Example PAC1 of which the percentage by the weight of D is 69%, with the balance being a hydrogen atom.

Example PAC5

PP415 PAC 88% Targeted Substitution

An appropriately sized and equipped reaction vessel was charged with 4.06 g (0.0098 mol) of PP415, 6.94 g (0.0258 mol), 1,2-naphthoquinone-diazide-4-sulfonylchloride and 172.33 g of acetone. After stirring the mixture to a uniform solution, the reaction solution was cooled by the water bath at room temperature. Then, a mixture of triethylamine/acetone (2.88 g (0.0284 mol)/13.40 g) was slowly added dropwise while maintaining the temperature at less than 35° C. After stirring for three hours at room temperature, 0.39 g (0.0065 mol) of acetic acid was added to the reaction mixture to neutralize. After stirring for 30 minutes further, the reaction mixture was filtered and poured into a mixture of pure water/acetic acid (891 g/9 g). After stirring for 1 hour, the resulting precipitate was collected, sufficiently washed with pure water and dried under vacuum. 5.16 g of a photosensitizer PAC-4 was obtained (yield: 65.4%). It was found that the resulted photosensitizer comprised of 40% of diester and 35% of triester by HPLC analysis.

Example PAC6

PP415 PAC 67% Targeted Substitution

An appropriately sized and equipped reaction vessel was charged with PP415 (17.0 g; 41 mmol) and acetone (860 mL). The resulting slurry was placed under a nitrogen blanket and stirred until the solid had dissolved. 6-diazo-5,6-dihydro-5-oxo-1-naphthalene sulfonyl chloride (22.03 g; 82 mmol) was added to the reaction vessel and the solution was stirred until the solution was homogeneous. Triethyl amine (TEA, 9.11 g, 90 mmol) was charged into the dropping funnel and added to the reaction vessel in a dropwise manner over a 12 minute period. The temperature of the reaction vessel was not controlled during the addition of the TEA.

After 3 hours reaction mixture was filtered on a Buchner funnel to remove the precipitated salts and the collected solids were washed with acetone (100 mL). The acetone was added to the filtrate. The combined organic phases were stirred with a magnetic stirrer and deionized water was added (8.5 mL). After 1 hour, glacial acetic acid (5 ml) was added. After an additional 35 minutes of stirring, the solution was added to a vigorously stirring mixture of water (2550 g) and methanol (850 g) over a 1 hour period. The aqueous solution was stirred for a further 10 minutes and the solid product recovered by filtered under vacuum and washed with deionized water (2 L). The product was dried in an oven at 40° C. under vacuum for 24 hours. 34 g (94% yield) of yellow powder was obtained. It was found that the resulting photoactive compound contained 10.88% monoester, 40.74% diester and 47.98% trimester.

Example PAC7

PP719 PAC 88% Targeted Substitution

An appropriately sized and equipped reaction vessel was charged with 3.24 g (0.0045 mol) of PP719 and 4.26 g (0.016 mol) of 1,2-naphoquinone-diazide-4-sulfonyl chloride and 43.5 g of acetone. The mixture was stirred to effect a uniform solution and cooled to room temperature with continued stirring. Next, a mixture of triethylamine/acetone (1.77 g, 0.017 mol of triethylamine) was added slowly to the solution while maintaining the temperature at less than 35° C. The reaction mixture was stirred for an additional 3 h after the addition of the triethylamine after which 0.24 g (0.004 mol) of acetic acid was added to quench the reaction. After stirring the mixture for an additional 30 min., the mixture was filtered and the filtrate added to a mixture of acetone/water (2 g/239 g) and this mixture allowed to stir of an additional 1 h. The resulting precipitate was collected by filtration, washed with water and then dried under vacuum. 5.60 g of PAC, an 84% yield, was obtained.

It was found that the PAC was 15% diester, 36% trimester and 42% tetraester by high performance liquid chromatography analysis (HPLC) analysis. Analysis by $^1$H-NMR indicated the expected structure.

Example PAC8

PP691 PAC 88% Targeted Substitution

An appropriately sized and equipped reaction vessel was charged with 4.75 g (0.0069 mol) of PP 691 and 6.50 g (0.024 mol) of 1,2-naphoquinone-diazide-4-sulfonylchloride and 63.75 g of acetone. The mixture was stirred to produce a uniform solution and cooled to room temperature with continued stirring. Next, a mixture of triethylamine/acetone (2.69 g, 0.027 mol of triethylamine) was added slowly to the solution while maintaining the temperature at less than 35° C. The reaction mixture was stirred for an additional 3 h after the addition of the triethylamine after which 0.36 g (0.006 mol) of acetic acid was added to quench the reaction. After stirring the mixture for an additional 30 min., the mixture was filtered and the filtrate added to a mixture of acetone/water (4 g/358 g) and this mixture allowed to stir of an additional 1 h. The resulting precipitate was collected by filtration, washed with water and then dried under vacuum. 8.11 g of PAC, an 81.3% yield, was obtained. It was found that the PAC was 13% diester, 30% trimester and 42% tetraester by HPLC analysis. Analysis by $^1$H-NMR indicated the expected structure.

Example PAC9

P334 PAC 100% Targeted Substitution

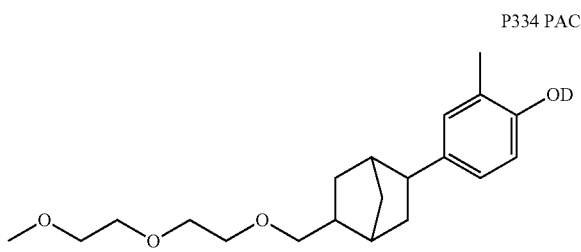

P334 PAC 2-diazo-1-naphthol-5-sulfonyl chloride (8.11 g, 0.035 mol) was charged to an appropriately sized and equipped reaction vessel. 60 ml acetone was added and the mixture magnetically stirred. P334 (NBTON-cresol) (10.10 g, 0.03 mol) was dissolved in 50 ml acetone and added to the reaction mixture. All remaining solids dissolved to give a red solution at 20° C. The mixture was cooled with an dry ice bath to about −5° C., causing precipitation. Triethylamine (3.33 g, 0.033 mol) was added drop wise. After two minutes, all triethylamine had been added and the reaction temperature rose to −0.9° C. The dry ice bath was removed and the mixture was allowed to warm to ambient temperature. The mixture was allowed to stir for an additional 2.75 hr during the warming and then filtered to remove any solids. The acetone filtrate was rotary evaporated to 17.93 g oil.

The oil was dissolved in 100 ml MTBE and treated with 130 ml 10% $NH_4OH$ for 45 min., separated, and the MTBE phases were washed with brine and water to pH 8. The combined organic phases was dried over sodium sulfate, filtered, and rotary evaporated to 9.45 g brown-yellow oil. The oil product was loaded onto 200 g silica and flushed with 100% MTBE and TONNB-cresol eluted with a small amount of product in the first two 500 ml fractions. PAC 567 was collected in the subsequent 12×500 ml fractions to give 14.49 g red oil after rotary evaporation. HPLC analysis showed two signals that totaled to 96.6% purity. The material was then redissolved in 150 ml EtOAc and flushed with EtOAc through 200 g silica. All material was collected in the first 3×500 ml fractions, which were rotary evaporated to 17.4 g oil treated with $CH_2Cl_2$ and rotary evaporated down to 0.56 Torr to give 14.44 g red-orange oil (85% yield). NMR analysis showed 0.9 wt % EtOAc and 0.6 wt % $CH_2Cl_2$ remaining. HPLC analysis showed two regioisomers components at 53.7% and 45.9% to total 99.6% P334 PAC.

Example PAC10

P343 PAC 100% Targeted Substitution

2-Diazo-1-naphthol-5-sulfonyl chloride (NAC-5) (8.48 g, 0.0315 mol) was placed in 4-neck 250-ml flask fitted with nitrogen inlet, addition funnel, and thermowell. 50 ml acetone was added and the mixture magnetically stirred. DecNB-cresol (9.83 g, 0.0287 mol) was dissolved in 60 ml acetone and added to the NAC-5/acetone mixture. All remaining NAC-5 solids dissolved to give a red solution at 21° C. The mixture was cooled to 0° C. Triethylamine (3.50 g, 0.0347 mol) was added drop wise causing immediate precipitation. After three minutes, all triethylamine had been added and the reaction temperature had risen to 3° C. The ice bath was removed and the mixture was allowed to warm to ambient temperature. After 15 minutes and at 18.8° C., TLC analysis (50% EtOAc/heptane on silica) showed both starting material and product. After 1.3 hrs at 28° C., the reaction mixture was filtered to remove 3.03 g of precipitated triethylammonium chloride ([Et$_3$NH]Cl). The salts and reaction flask were rinsed with acetone to bring the final solution volume to 200 ml. The filtrate was stirred as 100 ml distilled water was added, causing the product to oil out. 2.1 ml acetic acid was added and then two additional 100 ml portions of water were added, but the oil still remained. pH of the aqueous phase was 3. The aqueous phase was decanted from the oil and extracted with 50 ml and then with 4×25 ml dichloromethane. The dichloromethane extracts were added to the oil and the resulting solution then washed with 2×100 ml brine to pH 3. The extracts were dried over sodium sulfate, filtered, and rotary evaporated to 16.77 g oil. The oil was rotary evaporated further at 0.51-0.9 Torr for 2.5 hrs to give 16.19 g (98% yield) oil. HPLC analysis showed 92.6% DecNBArOQ and 5.7% NAC-5.

The oil was dissolved in 150 ml dichloromethane and washed with 100 ml 10% $NH_4OH$ to remove NAC-5. After numerous brine and water washes to achieve pH 8, the dichloromethane solution was dried over sodium sulfate, filtered, and rotary evaporated to 16.80 g oil. NMR analysis showed the material contained 6.8 wt. % $CH_2Cl_2$ and a small amount of NAC-5.

The 16.8 g of oil were dissolved in 150 ml dichloromethane with a small amount of heptane the solution was stirred with 150 ml 10% $NH_4OH$ for ~1 hr. After work up with water and brine washes, the organic portion was dried over sodium sulfate, filtered, and rotary evaporated to 15.24 g oil. NMR analysis found no NAC-5 and 5-6 wt. % $CH_2Cl_2$. The oil was sonicated with heptane to produce a yellow suspension which was filtered to give 11.06 g of yellow solids. The solids were suspended in pentane, sonicated, and again filtered to give 11.0 g (67% yield) fine yellow solid, mp 87-88° C. (oils, no bubbling observed). HPLC analysis gave 99.4% purity. Data: HPLC analysis done on a Restek Pinnacle C18, 150×4.6 mm; Mobile Phase: Methanol in $H_2O$+0.1% $HCO_2H$ Gradient: 25% to 100% over 20 minutes with a 10 minutes hold at 100%; Flow: 1.5 mL/min, Detected 254 nm (VWD). Retention time: 24.113 minutes.

Example PAC11

P475 PAC 100% Targeted Substitution

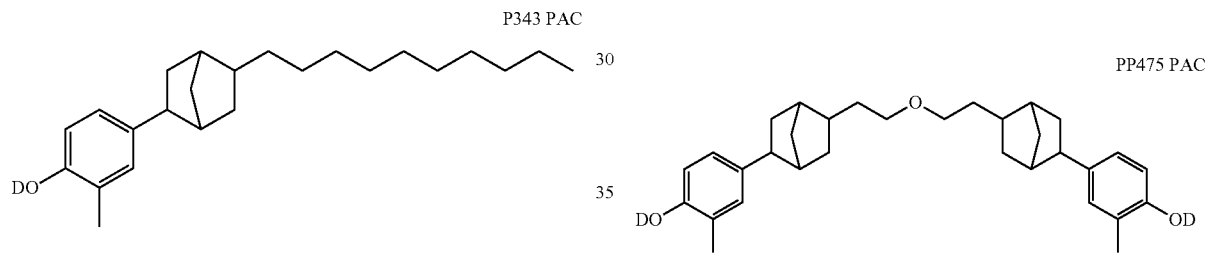

An appropriately sized and equipped reaction vessel was charged with 2-diazo-1-naphthol-5-sulfonyl chloride (6.5 g, 24.1 mmol) dissolved in 24 mL acetone and P343 ($C_6H_3$-2-Me-OH) (5.7 g, 12.1 mmol) dissolved in 24 mL acetone. After 15 minutes stirring a dark orange solution was observed. The mixture was cooled to 8° C. and the addition funnel was charged with triethylamine (3.5 mL, 25.3 mmol). The triethyl amine was added drop wise and the reaction mixture was allowed to warm up to room temperature. The slurry was stirred for 1 h at room temperature, filtered, and the Et$_3$NHCl salt and washed with acetone. The filtrate was concentrated and the residue was dissolved in 100 mL EtOH+5 mL acetone and kept in the refrigerator overnight for crystallization.

As no crystals were observed the solution was concentrated and the residue dissolved with 40 mL acetone and 0.7 g (12.1 mmol) glacial acetic acid and the solution stirred for 1 h at room temperature. The dark brown solution was poured into 360 mL water and stirred for 30 minutes. The light yellow precipitate that resulted was filtered and washed with water. The crude product was dried under house vacuum to give 12 g of crude product with 93.5% LC purity and 6.5% unreacted NAC-5 as impurity. The crude product was treated with aq. NaHCO$_3$, but no change in unreacted NAC-5 was observed. Treatment with 10% aq. K$_2$CO$_3$ treatment gave crude purity of 97.2% with 2.7% unreacted NAC-5. Finally unreacted NAC-5 was removed by stirring 30 min with 10% NH$_4$OH and extracting with CH$_2$Cl$_2$. The CH$_2$Cl$_2$ solution was dried over sodium sulfate, filtered, and rotary evaporated. The orange fluffy solid was further dried under high vacuum to give 10.5 g (92.9% yield) product as orange very fluffy solid with HPLC purity 98.5%. NMR and MS were consistent with the desired structure. Data: HPLC: Column: Restek Pinnacle C18, 150×4.6 mm; Mobile Phase: MeOH in $H_2O$+0.1% FA. Gradient: 5% to 100% MeOH in $H_2O$ (0.1% FA) over 20 minutes with a 10 minutes hold at 100% MeOH; Flow: 1.5 mL/min. Runtime: 30 min, Detected @ 254 nm (VWD); Retention time: 21.82 minutes Example PAC12

P308 PAC 100% Targeted Substitution

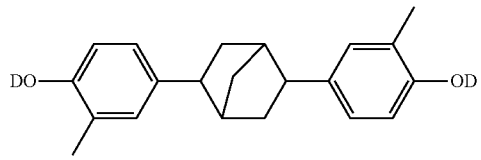

PP308 PAC

An appropriately sized and equipped reaction vessel was charged with 2-diazo-1-naphthol-5-sulfonyl chloride (7.3 g, 27.2 mmol) dissolved in 25 mL acetone and PP308 ($C_6H_3$-3-Me-OH)$_3$ (4.2 g, 13.6 mmol) dissolved in 25 mL acetone. After 15 minutes stirring a dark orange solution was observed. The mixture was cooled to 10° C. and the addition funnel was charged with triethyl amine (4.0 mL, 28.6 mmol). The triethyl amine was added drop wise and the reaction mixture warmed to room temperature. The slurry was stirred for 1 h at room temperature, the Et$_3$NHCl salt filtered and washed with acetone. The filtrate was stirred with 1.6 g (27.2 mmol) glacial acetic acid for 30 minutes at room temperature. The dark brown solution was poured into 800 mL water and a yellow precipitate was observed and stirred for 1 h. The light yellow precipitate was filtered and washed with water. The crude product was dried under house vacuum to give 27.8 g of wet crude product that was combined with a previous crude product and dissolved in 200 mL $CH_2Cl_2$ and washed with aq. NaHCO$_3$ and brine. The $CH_{12}Cl_2$ solution was dried over sodium sulfate, filtered, and rotary evaporated. The orange fluffy solid was further dried under high vacuum overnight to give 12.4 g (95.4% yield) product as an orange fluffy solid with HPLC purity 98.1%. NMR and MS were consistent with the desired structure.

Example PAC13

P459 PAC 100% Targeted Substitution

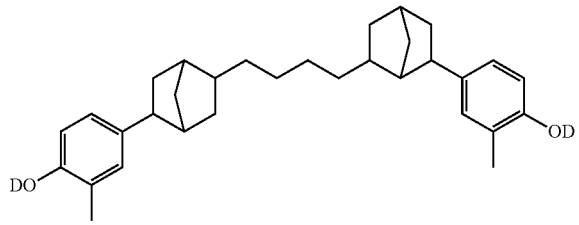

PP459 PAC

An appropriately sized and equipped reaction vessel was charged with 2-diazo-1-naphthol-5-sulfonyl chloride (5.4 g, 20.0 mmol) dissolved in 20 mL acetone and PP459 (4.6 g, 10.0 mmol) dissolved in 20 mL acetone. After 15 minutes stirring a dark orange solution was observed. The mixture was cooled to 10° C. and the addition funnel was charged with triethyl amine (2.9 mL, 21.0 mmol). The triethyl amine was added drop wise and the reaction mixture warmed to room temperature. The slurry was stirred for 1 h at room temperature, the Et$_3$NHCl salt filtered and washed with acetone. The filtrate was stirred with 1.2 g (20.0 mmol) glacial acetic acid for 30 minutes at room temperature. The dark brown solution was poured into 700 mL water and a yellow turbid solution was observed and stirred for 1 h. The light yellow turbid solution was extracted with (3×200 mL) $CH_2Cl_2$ and washed with aq. NaHCO$_3$ and brine. The $CH_2Cl_2$ solution was dried over sodium sulfate, filtered, and rotary evaporated. The orange fluffy solid was further dried under high vacuum overnight to give 7.9 g (85.0% yield) product as an orange fluffy solid with HPLC purity 97.6%. NMR and MS were consistent with the desired structure.

Example PAC14

P343 PAC 100% Targeted Substitution

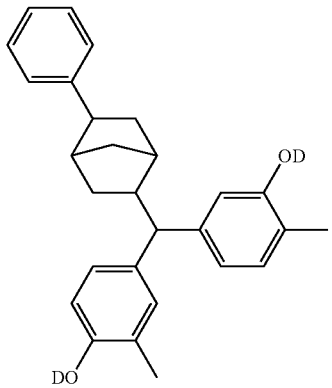

PP399 PAC

An appropriately sized and equipped reaction vessel was charged with 2-diazo-1-naphthol-5-sulfonyl chloride (5.04 g, 18.8 mmol) dissolved in 20 mL acetone and PP399 ($C_6H_2$-2,5-Me$_2$-OH)$_2$ (4.0 g, 9.4 mmol) dissolved in 20 mL acetone. After 15 minutes stirring a dark orange solution was observed. The mixture was cooled to 10° C. and the addition funnel was charged with triethyl amine (2.74 mL, 18.8 mmol). The triethyl amine was added drop wise and the reaction mixture warmed to room temperature. The slurry was stirred for 1 h at room temperature, the Et$_3$NHCl salt filtered and washed with acetone. The filtrate was stirred with 1.1 g (18.8 mmol) glacial acetic acid for 30 minutes at room temperature. The dark brown solution was poured into 600 mL water and a yellow precipitate was observed and stirred for 1 h. The light yellow precipitate was filtered and washed with water. The crude product was dried under house vacuum to give 28.8 g of wet crude product that was combined with a previous crude product and dissolved in 250 mL $CH_2Cl_2$ and washed with aq. NaHCO$_3$ and brine. The $CH_2Cl_2$ solution was dried over sodium sulfate, filtered, and rotary evaporated. The orange fluffy solid was further dried under high vacuum overnight to give 10.2 g (98.2% yield) product as an orange fluffy solid with HPLC purity 99.35%. NMR and MS were consistent with the desired structure.

Example PAC14

PP375 PAC 100% Targeted Substitution

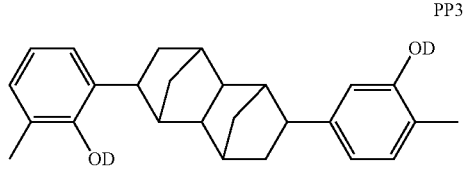

PP375 PAC

An appropriately sized and equipped reaction vessel was charged with 2-diazo-1-naphthol-5-sulfonyl chloride (0.86 g, 3.2 mmol) dissolved in 3.5 mL acetone and PP375 (0.6 g, 1.6 mmol) dissolved in 3.5 mL acetone. After 15 minutes stirring a dark orange solution was observed. The mixture was cooled to 10° C. and the addition funnel was charged with triethylamine (0.5 mL, 3.4 mmol). The triethylamine was added drop wise and the reaction mixture warmed to room temperature. The slurry was stirred for 1 h at room temperature, the $Et_3NHCl$ salt filtered and washed with acetone. The filtrate was stirred with 0.2 g (3.2 mmol) glacial acetic acid for 30 minutes at room temperature. The dark brown solution was poured into 100 mL water and a yellow precipitate was observed and stirred for 1 h. The light yellow precipitate was filtered and washed with water. The crude product was dried under house vacuum to give 28.8 g of wet crude product that was combined with a previous crude product and dissolved in 100 mL $CH_2Cl_2$ and washed with aq. $NaHCO_3$ and brine. The $CH_2Cl_2$ solution was dried over sodium sulfate, filtered, and rotary evaporated. The orange fluffy solid was further dried under high vacuum overnight to give 1.2 g (89.5% yield) product as an orange fluffy solid with LC purity 98.4%. NMR and MS were consistent with the desired structure.

Example PAC15

PP351 PAC 100% Targeted Substitution

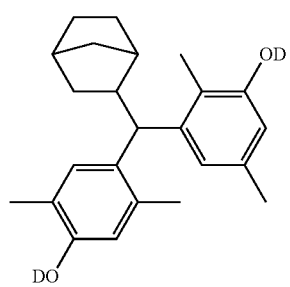

PP351 PAC

An appropriately sized and equipped reaction vessel was charged with 2-diazo-1-naphthol-5-sulfonyl chloride (7.7 g, 28.5 mmol) dissolved in 30 mL acetone and PP351 ($C_6H_2$-2,5-$Me_2$-OH)$_2$ (5 g, 14.2 mmol) dissolved in 30 mL acetone was added. After 15 minutes stirring a dark orange solution was observed. The mixture was cooled to 10° C. and the addition funnel was charged with triethylamine (4.18 mL, 29.9 mmol). The triethylamine was added drop wise and the reaction mixture warmed to room temperature. The slurry was stirred for 1 h at room temperature, filtered and the $Et_3NHCl$ salt washed with acetone. The filtrate was stirred with 1.7 g (28.5 mmol) glacial acetic acid for 30 minutes at room temperature. The dark brown solution was poured into 900 mL water and yellow precipitate was observed, and stirred for 1 h. The light yellow precipitate was filtered and washed with water. The crude product was dried under house vacuum to give 12 g of crude wet product that was dissolved in 200 mL $CH_{12}Cl_2$ and washed with aq. $NaHCO_3$ and brine. The $CH_2Cl_2$ solution was dried over sodium sulfate, filtered, and rotary evaporated. The orange fluffy solid was further dried under high vacuum overnight to give 11.5 g (99.1% yield) product as a very fluffy, orange solid with HPLC purity 99.9%. NMR and MS were consistent with the desired structure.

Positive-Tone Resin Compositions

The positive-tone photosensitive resin composition embodiments in accordance with the present invention encompass one of a PBO alkali-soluble resin (A) or a PNB alkali-soluble resin (A*); a photoactive compound (B) that encompasses an NBane-type ballast compound, such as described herein, where some or all of the aryl hydroxide groups have each been replaced by one of the following sulfonic acids or their respective acid chlorides: 1,2-naphthoquinone-2-diazido-5-sulfonic acid, 1,2-naphthoquinone-2-diazido-4-sulfonic acid or 2-diazo-4-hydrosulfonylcyclohex-3-enone, the structures of which are shown, respectively below, to form the esters thereof:

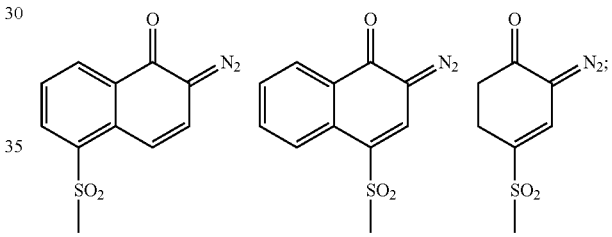

an appropriate casting solvent.

Advantageously, it has been found that the dimensional change of patterns formed from films made from such photosensitive resin composition embodiments provide for both high photosensitivity and high pattern resolution even where the thickness of film formed thereof is greater than or equal to 10 μm.

The content of the photosensitizer (B) is, but not particularly limited to, preferably 1 to 50 parts by weight, especially preferably 10 to 40 parts by weight, relative to 100 parts by weight of the alkali-soluble resin (A). By setting the content of such a photosensitizer within the range mentioned above, it is possible to obtain a positive-type photosensitive resin composition with a good sensitivity and resolution without the scum, as well as with a small dimensional change of patterns before and after curing.

Resin A

The alkali-soluble resin (A) used in some of the positive-tone, aqueous base developable, photosensitive resin composition embodiments in accordance with the present invention that are described herein encompasses a resin having a benzoxazole precursor structure in the main chain. From the viewpoint of ensuring excellent sensitivity and resolution when forming a coated layer pattern, and ensuring excellent heat resistance and mechanical strength of the cured layer, a resin having a benzoxazole precursor structure and an imide structure in the main chain and further having a hydroxyl group, a carboxyl group, an ether group, or an ester group in the main chain or a side chain; a resin having a benzoxazole precursor structure and an imide precursor structure in the main chain; and a resin having a benzoxazole precursor structure and an amide ester structure in the main chain are useful as the alkali-soluble resin (A). Such a resin (A) is shown in generic form by the following formula DD, where such resin encompasses a first repeating unit indicated as D1 and a second repeating unit indicated as D2:

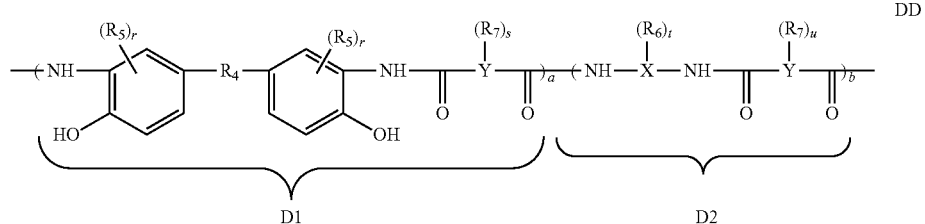

DD

Such first and second repeating units are generally dispersed randomly throughout resin (A) being bonded via an amide bond, as shown.

In formula DD, X and Y are organic groups. $R_4$ is a group selected from an alkylene group, a substituted alkylene group, —O—, —S—, —SO$_2$—, —CO—, —NHCO—, and —C(CF$_3$)$_2$—. $R_5$ is an alkyl group, an alkoxy group, an acyloxy group or a cycloalkyl group, and if there are two or more $R_5$ s, each $R_5$ can be either the same or different. $R_6$ represents an —O—$R_8$— group and if there are two or more $R_6$ s, each $R_6$ can be either the same or different. $R_7$ is a hydroxyl group, a carboxyl group, —O—$R_8$, or —COO—$R_8$— and if there are two or more $R_7$ s, the $R_7$ s can be either the same or different. $R_8$ represents an organic group having 1 to 15 carbon atoms. Each r is independently an integer of 0 to 3, each t independently an integer of 0 to 2, each s independently an integer of 0 to 4, and each u independently an integer of 0 to 4. The variables a and b shown for the first and second repeating units, respectively, indicate the molar ratio, by percentage, of such repeating units in alkali-soluble resin (A), the sum of a and b being 100%. Generally, a is 30 to 100%, and b is 0 to 70%. In formula DD, a and b indicate the mole percent, respectively, of the structural unit shown by formula D1 and the structural unit shown by formula D2 in the alkali-soluble resin (A), but do not indicate that these structural units are continuous. The alkali-soluble resin (A) shown by formula DD includes structures derived by ring-closing of part of the benzoxazole precursor structure, amide acid ester structure, or imide precursor structure shown in formula DD.

Exemplary alkylene and substituted alkylene groups, shown as $R_4$ in the repeating unit of formula D1, include, but are not limited to, —CH$_2$—, —CH(C$_3$)—, —C(CH$_3$)$_2$—, —CH(CH$_2$CH$_3$)—, —C(CH$_3$)(CH$_2$CH$_3$)—, —C(CH$_2$CH$_3$)(CH$_2$CH$_3$)—, —CH(CH$_2$CH$_2$H$_3$)—, —C(CH$_3$)(CH$_2$CH$_2$CH$_3$)—, —CH(CH(CH$_3$)$_2$)—, —C(CH$_3$)(CH(CH$_3$)$_2$)—, —CH(CH$_2$CH$_2$CH$_2$CH$_3$)—, —C(CH$_3$)(CH$_2$CH$_2$CH$_2$CH$_3$)—, —CH(CH$_2$CH(CH$_3$)$_2$)—, —C(CH$_3$)(CH$_2$CH(CH$_3$)$_2$)—, —CH(CH$_2$CH$_2$Cl$_2$CH$_3$)—, —C(CH$_3$)(CH$_2$CH$_2$CH$_2$CH$_2$CH$_3$)—, —CH(CH$_2$CH$_2$CH$_2$CH$_2$CH$_3$)—, —C(CH$_3$)(CH$_2$CH$_2$CH$_2$CH$_2$CH$_2$CH$_3$)—. It will be understood that such groups can produce an alkali-soluble resin (A) exhibiting sufficient solubility in both an alkaline aqueous solution, and in an appropriate solvent.

In resin (A), —O—$R_8$ as the substituent of X, and —O—$R_8$ and —COO—$R_8$ as the substituent of Y are groups in which a hydroxyl group or a carboxyl group is protected by R8, an organic protecting group having 1 to 15 carbon-atoms where the number of carbons selected for $R_8$ is generally useful for adjusting the solubility of the hydroxyl group or carboxyl group in an alkaline aqueous solution. Exemplary protecting groups can include, among others, a formyl group, a methyl group, an ethyl group, a propyl group, an isopropyl, a tert-butyl group, a tert-butoxycarbonyl group, a phenyl group, a benzyl group, a tetrahydrofuranyl group, a tetrahydropyranyl group.

Resin (A) can be obtained by, for example, reacting a bis(aminophenol) which is a polymerization raw material from which the structure originating from diamine in the structural unit shown by formula D1 is derived, optionally a diamine which is a polymerization raw material from which the structure originating from the diamine including X in the structural unit shown by formula D2 is derived, and a compound selected from the group consisting of tetracarboxylic dianhydride, trimellitic anhydride, dicarboxylic acid, dicarboxylic acid dichloride, dicarboxylic acid derivatives, hydroxy dicarboxylic acid, hydroxy dicarboxylic acid derivatives, and the like, which are polymerization raw materials from which a structure originating from an acid including Y in the structural unit shown by formula D1 and the structural unit shown by formula D2 are derived. In the case of the dicarboxylic acid, an active ester-type dicarboxylic acid derivative previously reacted with 1-hydroxy-1, -2,3-benzotriazole or the like can be used in order to increase the reaction yield.

Alternative structures and details of such PBO resins are known and can be found, for example, in previously mentioned U.S. Pat. No. 7,781,131 which is incorporated herein by reference.

Resin A*

The alkali-soluble resin (A*) used in some other of the positive-tone, aqueous base developable, photosensitive resin composition embodiments in accordance with the present invention that are described herein encompasses a resin having a polynorbornene-type structure in the main chain and is referred to herein as a PNB or PNB resin (A*). From the viewpoint of ensuring excellent sensitivity and resolution when forming a coated layer pattern, and ensuring excellent heat resistance and mechanical strength of the final layer, a resin having a polynorbornene-type structure in the polymer backbone, where such structure is formed by a vinyl addition process rather than a ROMP process, is useful as the alkali-soluble resin (A*). Such a resin (A*) is shown in generic form by the following formula EE, where such resin encompasses a first repeating unit indicated as E1 and a second repeating unit indicated as E2:

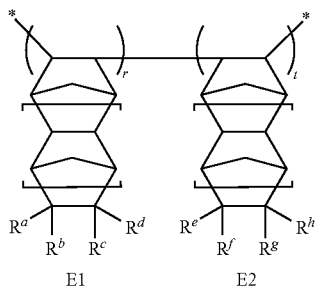

EE

Such first and second repeating units are generally dispersed randomly throughout resin (A*) being bonded via an amide bond, as shown. The variables 'a' and 'b' shown for the first and second repeating units, respectively, indicate the molar ratio, by percentage, of such repeating units in alkalisoluble resin (A*), the sum of a and b being 100%. It should be understood, however, that not all such resins (A*) have a first and a second repeating unit. Rather some resins (A*) are homopolymers and therefore have only one type of repeating unit, while other resins (A*) have more than two types of repeating units. Thus where, for example, there are three types of repeating units a variable 'c' would be used the denote the mole percent of that third type of repeat unit and then the sum of a, b and c would be 100%.

As mentioned above PNB resins in accordance with formula EE are formed via a vinyl addition polymerization reaction. Such reaction results in the 2,3-enchainment of norbornene-type monomers via a metal catalyzed addition reaction. Suitable metal catalysts are generally Pd or Ni containing and they and the polymerization reactions they cause to occur are described in U.S. Pat. No. 6,455,650 and U.S. Pat. No. 6,232,417, respectively, the pertinent parts of which are incorporated herein by reference.

Referring again to formula EE, any of $R^a$, $R^b$, $R^c$, $R^d$, $R^e$, $R^f$, $R^g$ and $R^h$ can be a hydrocarbyl group, where such group can be a $C_1$ to $C_{30}$ alkyl, aryl, aralkyl, alkaryl, alkenyl, alkynyl, cycloalkyl, cycloalkenyl, alkylidenyl or alkylsilyl group. Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl, butenyl and cyclohexenyl. Representative alkynyl groups include, but are not limited to, ethynyl, 1-propynyl, 2-propynyl, 1-butynyl and 2-butynyl. Representative cycloalkyl groups include, but are not limited to, cyclopentyl, cyclohexyl and cyclooctyl substituents. Representative aryl groups include, but are not limited to, phenyl, naphthyl and anthracenyl. Representative aralkyl groups include, but are not limited to, benzyl and phenethyl. Representative alkylidenyl groups include methylidenyl and ethylidenyl groups. In addition, it should be noted that the hydrocarbyl groups mentioned above can be substituted, that is to say one of the hydrogen atoms replaced, with $C_1$-$C_{10}$ alkyl, haloalkyl and perhaloalkyl groups, aryl groups and cycloalkyl groups.

Any of $R^a$ to $R^h$ can also be a halohydrocarbyl group, where such group includes any of the hydrocarbyls mentioned above where at least one, but less than all, of the hydrogen atoms of the hydrocarbyl are replaced by a halogen (fluorine, chlorine, bromine or iodine). Additionally, any of $R^a$ to $R^b$ can be a perhalocarbyl, where such group includes any of the hydrocarbyls mentioned above where all of the hydrogen atoms of the hydrocarbyl are replaced by a halogen. Useful perfluorinated substituents include perfluorophenyl, perfluoromethyl, perfluoroethyl, perfluoropropyl, perfluorobutyl and perfluorohexyl.

Further, it will be understood that any of $R^a$ to $R^h$ can also be a heterohydrocarbyl group, which refers to any of the previously described hydrocarbyls, halohydrocarbyls and perhalohydrocarbyls where at least one carbon of the carbon chain is replaced with N, O, S, Si or P. Non-limiting examples include heterocyclic aromatic groups such as pyrrolyl, furanyl, and the like, as well as non-aromatic groups such as ethers, thioethers and silyl ethers, alcohols, carboxylic acids and esters, ketones and aldehydes. Specific, useful monomers for the preparation of PNB resin (A*) are listed in the table below, where for each acronym a representative chemical name is provided:

| | |
|---|---|
| HFANB | 2-(bicyclo[2.2.1]hept-5-en-2-ylmethyl)-1,1,1,3,3,3-hexafluoropropan-2-ol |
| TFSNB | N-(bicyclo [2.2.1]hept-5-en-2-ylmethyl)-1,1,1-trifluoromethanesulfonamide |
| FPCNB | 2,2,3,3,3-pentafluoropropylester of 5-norbornene-2-carboxylic acid |
| NBMeOAc | 2-hydroxymethyl-5-norbornene acetate |
| NBPhOAc | 4-(bicyclo[2.2.1]hept-5-en-2-yl)phenyl acetate |
| t-BuEsNB | t-butylester of 5-norbornene-2-carboxylic acid |
| MCPNB | 5-(1-methylcyclopentyl)bicyclo[2.2.1]hept-2-ene |
| NB | norbornene |
| TFENB | bicyclo[2.2.1]hept-5-ene-2-carboxylic acid tetrahydro-2-oxo-3-furanyl ester |
| TESNB | (bicyclo[2.2.1]hept-5-en-2-ylmethyl)triethoxysilane |
| MGENB | 2-((bicyclo[2.2.1]hept-5-en-2-ylmethoxy)methyl)oxirane |
| Acid NB | bicyclo[2.2.1]hept-5-ene-2-carboxylic acid |
| DecNB | 5-decylbicyclo[2.2.1]hept-2-ene |
| PENB | 5-phenethylbicyclo[2.2.1]hept-2-ene |
| BuNB | 5-butylbicyclo[2.2.1]hept-2-ene |
| NBM(PhMeOH)$_2$ | 4,4'-(bicyclo[2.2.1]hept-5-en-2-ylmethylene)bis(2-methylphenol) |
| NBMMPA | 4-norbornenylmethyl-2-methoxyphenol acetate |
| NBMMPhOH | 4-(bicyclo[2.2.1]hept-4-en-2-ylmethyl)-2-methoxyphenol |
| NBMMHFP | 2-((bicyclo[2.2.1]hept-5-en-2-yloxy)methyl)-1,1,1,3,3,3-hexafluoropropan-2-ol |
| EPENB | ethyl 3-(bicyclo[2.2.1]hept-2-en-2-yl)propanoate |
| EPANB | 3-(bicyclo[2.2.1]hept-2-en-2-yl)propanoic acid |
| NBPhOH | 4-(bicyclo[2.2.1]hept-5-en-2-yl)phenol |
| NBE4ECBz | 2-(bicyclo[2.2.1]hept-5-en-2-yl)ethyl 4-((ethoxycarbonyl)oxy)benzoate |
| NBE2AcOBz | 2-(bicyclo[2.2.1]hept-5-en-2-yl)ethyl 2-acetoxybenzoate |
| NBE2OHBz | 2-(bicyclo[2.2.1]hept-5-en-2-yl)ethyl 2-hydroxybenzoate |
| NBMGlyHFP | 2-(2-(bicyclo[2.2.1]hept-5-en-2-yloxy)ethoxy)-1,1,1,3,3,3-hexafluoropropan-2-ol |

The positive-tone photosensitive resin composition embodiments in accordance with the present invention are first used to make a film when applied in an appropriate manner to an appropriate support (substrate). Such substrates include, but are not limited to, a silicon wafer, a ceramic substrate or an aluminum. When applied such a substrate, an appropriate amount of such composition embodiment is used to make a film with a desired final thickness, (e.g. from 0.1 to 30 μm). Examples of the method for applying the composition to a substrate include spin coating, spray coating, immersion coating, printing and roll coating.

After a positive-tone photosensitive resin composition embodiment is applied to a substrate to form a coating film, such film is dried to remove any residual casting solvent and form a dried film. While the time and temperature of such a prebake step is generally a function of, among other things, the thickness of the applied film, the casting solvent used and the method of coating, usually a temperature from 60 to 150° C. for from 20 to 120 seconds is appropriate. It should of course be understood that the specific temperatures and times provided above are exemplary and other times and/or temperatures can also be employed.

Once a dried film is obtained, such film is typically exposed to an appropriate amount of actinic radiation. Such exposure generally being done through a masking element such that some portions of the film are exposed to the radiation while other portions remain unexposed. While actinic radiation generally refers to radiation in the UV range of wavelengths, herein such term will be understood to also refer to X rays, electron beams, and wavelengths of such radiation in the visible range of wavelengths. The intensity of the radiation employed and its duration combine to define the term "exposure dose" and an appropriate dose, will be a function of, among others, the resin and PAC employed to make the film as well as the film thickness and the PAC concentration in the film.

While image development generally follow the exposure step, for some embodiments in accordance with the present invention, a post exposure bake (PEB) may be performed, where the conditions of PEB are often similar to the pre-exposure bake previously discussed. When image development is performed, an aqueous alkali developer. Exemplary developers include, but are not limited to aqueous solutions of alkali compounds such as inorganic alkali compounds, for example, sodium hydroxide, potassium hydroxide, sodium carbonate, sodium silicate, sodium metasilicate and ammonia water as well as some aqueous soluble organic amines and amine salts. As the development method, there may be used spraying, puddling, immersion, and application of supersonic waves. It will be understood that as the film forming composition embodiments in accordance with the present invention employ a DNQ substituted PAC, such material serves to depress the dissolution rate of the resin in those film regions that were unexposed as compared to the exposed regions. In this manner a positive image of the masking elements is formed.

Next, the relief pattern formed by development process is rinsed to remove any residual developer material and where a PBO resin (A) was employed, the resulting patterned film heated to "cure" the resin. That is to say, to form an oxazole ring, an imide ring, or both of the imide ring and oxazole ring, whereby a final pattern having excellent heat resistance can be obtained. Where a PNB resin (A*) was employed, generally a curing step is not needed as the PNB resin is generally completely polymerized at the time it is used to form the film forming composition. However, for some PNB resin (A*) embodiments, one or more of the repeating units of such resin can have pendent groups that provide for a cross-linking reaction to occur within such remaining regions.

Where the heating step is needed to cure a PBO resin (A), such heating is generally at temperatures at or below 350° C. and often below 300° C. Where the heating step is needed to induce the crosslinking of a PNB resin (A*), such heating is generally at temperatures at or below 300° C. and often below 250° C. Regarding a method for such heating to cure or crosslink the resin, an oven, hot plate, electric furnace, infrared rays or microwave are generally appropriate means for such heating.

The finally made films made from the resin composition embodiments of the present invention are useful as protective films or insulated films for microelectronic devices such as a semiconductor element or the like, and also for optoelectronic devices such as a TFT liquid crystal and organic EL displays, an interlayer insulating film of a multilayered circuit, a cover coat of a flexible copper-clad board, a solder resist film and a liquid crystal alignment film.

Moreover, the microelectronic and optoelectronic device embodiments of the present invention are characterized by encompassing the aforementioned films, where such films can be patterned as described above, or simply blanket exposed to the actinic radiation so that a continuous final film results.

Examples of the application to semiconductor devices include a passivation film obtained by forming a cured film of the aforementioned positive photosensitive resin composition on a semiconductor element; a protecting film such as a buffer coating film obtained by forming a cured film of the aforementioned positive photosensitive resin composition on the passivation film; an insulating film such as an interlayer insulating film obtained by forming a cured film of the aforementioned positive photosensitive resin composition on the circuit formed on the semiconductor element; an α-ray shielding film; a flattening film; a projection (a resin post); a partition; and the like.

Examples of the application of embodiments of the present invention to display devices include a protecting film obtained by forming a cured or final film of the aforementioned photosensitive resin composition on a display element; an insulating film or a flattening film for a TFT element or a color filter; a projection for an MVA-type liquid crystal display device and the like; a partition for an organic EL element cathodes; and the like. The method of use of the composition for semiconductor devices applies to the method of use for the display devices, that is, a method of forming a patterned layer of the photosensitive resin composition on a substrate on which a display element or a color filter is formed may be used. High transparency is required particularly for an insulating film or a flattening film of display devices. A resin layer excellent in transparency can also be obtained by introducing a post exposure process before curing the layer of the photosensitive resin composition. Introduction of such a post exposure process is further preferable in practice.

Resin (A) and Photo Evaluation Thereof

Example Resin A1

To an appropriately sized and equipped reaction vessel, 416.13 g (0.845 mol) of a dicarboxylic acid derivative (active ester), which was obtained by reacting 0.845 mol of diphenyl ether-4,4'-dicarboxylic acid and 1.690 mol of 1-hydroxy-1,2,3-benzotriazole, and 329.63 g (0.900 mol) of hexafluoro-2,2-bis(3-amino-4-hydroxyphenyl)propane and 23.03 g (0.100 mol) of bis(3-amino-4-hydroxyphenyl)methane was charged under a nitrogen blanket. Then 3050 g of N-methyl-2-pyrrolidone was added to dissolve the dicarboxylic derivative and the reaction mixture heated to 75° C. for 16 hours. Next, 50.89 g (0.310 mol) of 5-norbornene-2,3-dicarboxylic anhydride and 200 g of N-methyl-2-pyrrolidone were added and the mixture was stirred at temperature for an additional 3 hours to complete the reaction.

The reaction mixture was filtered and poured into a 3:1 (volume ratio) mixture of water and isopropanol. The resulting precipitate was collected by filtration was sufficiently washed with water and dried under vacuum to obtain a polybenzoxazole precursor resin (A-1) with a number average molecular weight ($M_n$) of 9,200.

Example Resin A-2

To an appropriately sized and equipped reaction vessel, 378.06 g (0.830 mol) of a dicarboxylic acid derivatives (active ester), which were obtained by reacting 0.498 mol of diphenyl ether-4,4'-dicarboxylic acid and 0.998 mol of 1-hydroxy-1,2,3-benzotriazole and 0.332 mol of isophthalic acid and 0.664 mol of 1-hydroxy-1,2,3-benzotriazole, and 146.50 g (0.400 mol) of hexafluoro-2,2-bis(3-amino-4-hydroxyphenyl)propane, 85.91 g (0.300 mol) of 4,4'-methylenebis(2-amino-3,6-dimethyl phenol) and 69.08 g (0.300 mol) of bis(3-amino-4-hydroxyphenyl)methane under a nitrogen blanket. 2050 g of N-methyl-2-pyrrolidone was added to dissolve the mixture and the mixture heated to 75° C. for 16 hours. Next, 55.81 g (0.340 mol) of 5-norbornene-2,3-dicarboxylic anhydride and 170 g of N-methyl-2-pyrrolidone were added and the mixture was stirred for an additional 3 hours to complete the reaction.

The reaction mixture was filtered and poured into a 3:1 (volume ratio) mixture of water and isopropanol. The resulting precipitate was collected by filtration was sufficiently washed with water and dried under vacuum to obtain a polybenzoxazole precursor resin (A-2) with a number average molecular weight ($M_n$) of 9,300.

Example Resin A-3

An appropriately sized and equipped reaction was charged under nitrogen with 3,3'-diaminodiphenylmethane 29.74 g (0.15 mol) and N-methyl-2-pyrrolidone 300 g, to form a solution thereof. After addition of 4,4'-oxydiphthalic anhydride 39.09 g (0.126 mol), the reaction was stirred at room temperature for one hour and then in an oil bath at 65° C. for 2 hours. Then, a dicarboxylic acid derivative (active ester) 351.62 g (0.714 mol) obtained by reacting hexafluoro-2,2-bis (3-amino-4-hydroxyphenyl)propane 311.32 g (0.85 mol) and diphenyl ether-4,4'-dicarboxylic acid (0.714 mol) with 1-hydroxy-1,2,3-benzotriazole (1.428 mol) was added together with N-methyl-2-pyrrolidone 2600 g, was added and the resulting mixture heated to 75° C. and stirred for 16 hours. Subsequently, after addition of 52.53 g (0.320 mol) of 5-norbornene-2,3-dicarboxylic anhydride dissolved in 150 g of N-methyl-2-pyrrolidone, the mixture was stirred for further 3 hours to complete the reaction. The reaction mixture was filtered, and poured into a 3:1 (volume ratio) mixture of water and isopropanol. The resulting precipitate was collected by filtration, washed well with water, and dried under vacuum to obtain a copolymer resin composed of the polyimide precursor and the polybenzoxazole precursor as an alkali-soluble resin (A-3) with a number average molecular weight of 8100.

Composition Example PBO A-1 PAC-1

10 g of the synthesized polybenzoxazole precursor resin (A-1) and 1.4 g of diazoquinone compound which has a structure of the formula (PAC-1) were dissolved in a solvent of 13 g of γ-butyrolactone. The solution was filtered through a Teflon® (filter with a pore size of 0.2 μm to obtain a photosensitive resin composition.

Photoimaging 1 Composition Example PBO A-1 PAC-1

The photosensitive resin composition was applied to a silicon wafer using a spin coater and prebaked on a hot plate at 120° C. for 200 seconds to obtain a coated film with a thickness of about 13.0 min. The coated film on the wafer was irradiated using i-line stepper (NSR-4425i, Nikon Co.) through a mask (a test chart No. 1 having a remnant pattern and an extract pattern, each having a width of 0.88 to 50 ins, manufactured by Toppan Printing Co., ltd.) while changing the exposure dose. Then, the coated wafer was developed twice by a paddle method using an aqueous solution of 2.38% tetramethylammonium hydroxide for 25 seconds each time to remove the exposed areas and washed with purified water for 10 seconds.

As a result, it was confirmed that the pattern was formed starting at the area irradiated at a dose of 410 ml/cm$^2$, indicating very high sensitivity (sensitivity was 410 mJ/cm$^2$). The resolution was 4 μm and the scum was not confirmed. The film thickness after development was 11.0 μms.

As a result of measuring the dimension of a 10 μm square pattern opening in the area exposed at a dose of 460 mJ/cm$^2$ on a wafer with patterns prepared above by a laser microscope OPTELICS (registered trade mark) H1200 (manufactured by Lasertec Corp.), there was obtained a result of 10.1 um. Then, heat treatment of the wafer with patterns was performed for 180 seconds using a hot plate set to 320° C. After such a heat treatment, the dimension of the same opening was measured to provide a good result of 9.8 um.

Photoimaging 2 Composition Example PBO A-1 Q-2

A photosensitive resin composition was prepared in the same manner as in Example 1, except for using the photosensitizer (Q-2) instead of the photosensitizer (Q-1), and evaluated in the same manner as in Example 1. The results were shown in Table 1. In addition, evaluation of the dimensional changes before and after curing was performed using a 10 μm square pattern opening in the area exposed at a dose of 490 mJ/cm$^2$.

Photoimaging 3 Composition Example PBO A-2 Q-3

A photosensitive resin composition was prepared in the same manner as in Example 1, except for using the alkali-soluble resin (A-2) instead of the alkali-soluble resin (A-1) and 1.5 g of the photosensitizer (Q-3) instead of 1.4 g of the photosensitizer (Q-1), and evaluated in the same manner as in Example 1. The results were shown in Table 1. In addition, evaluation of the dimensional changes before and after curing was performed using a 10 μm square pattern opening in the area exposed at a dose of 480 mJ/cm$^2$.

Photoimaging 4 Composition Example PBO A-3 Q-1

A photosensitive resin composition was prepared in the same manner as in Example 1, except for using the alkali-soluble resin (A-3) instead of the alkali-soluble resin (A-1) and changing the blending amount of the photosensitizer (Q-1) to 1.7 g, and evaluated in the same manner as in Example 1. The results were shown in Table 1. In addition, evaluation of the dimensional changes before and after curing was performed using a 10 μm square pattern opening in the area exposed at a dose of 570 mJ/cm$^2$.

Composition Comparative Example 1

A photosensitive resin composition was prepared in the same manner as in Example 1, except for using the photosensitizer (Q-4) instead of the photosensitizer (Q-1), and evaluated in the same manner as in Example 1. The results were shown in Table 1. In addition, evaluation of the dimensional changes before and after curing was performed using a 10 μm square pattern opening in the area exposed at a dose of 600 ml/cm$^2$.

Composition Comparative Example 2

A photosensitive resin composition was prepared in the same manner as in Example 3, except for using the photosensitizer (Q-4) instead of the photosensitizer (Q-3), and evaluated in the same manner as in Example 1. The results were shown in Table 1. In addition, evaluation of the dimensional changes before and after curing was performed using a 10 μm square pattern opening in the area exposed at a dose of 620 mJ/cm$^2$.

Composition Comparative Example 3

A photosensitive resin composition was prepared in the same manner as in Example 4, except for using the photosensitizer (Q-4) instead of the photosensitizer (Q-1), and evaluated in the same manner as in Example 1. The results were shown in Table 1. In addition, evaluation of the dimensional changes before and after curing was performed using a 10 μm square pattern opening in the area exposed at a dose of 690 mJ/cm$^2$, but it was confirmed by observation of the patterns after curing that such openings were filled and not opened.

TABLE 1

| Formulation Ex # | †PAC Ex. # Loading (pphr) | Resin Ex # | Lithography Data Sensitivity (mJ/cm$^2$) | Resolution (μm) | ††Dimensions Feature Size Change (μm) |
|---|---|---|---|---|---|
| Comp Ex 1 | PAC-4 14 | A-1 | 550 | 5 | 9.1 |
| Comp Ex 2 | PAC-4 15 | A-2 | 570 | 5 | 9.0 |
| Comp Ex 3 | PAC-4 17 | A-3 | 640 | 10 | filled in |
| 1 | PAC-1 14 | A-1 | 410 | 4 | 0.3 |
| 2 | PAC-2 14 | A-1 | 440 | 4 | 0.2 |
| 3 | PAC-3 15 | A-2 | 430 | 4 | 0.3 |
| 4 | PAC-1 17 | A-3 | 520 | 6 | 0.3 |

†all PACs are 88% Target DNQ Loading
††Change measured before and after the resin (A) cure cycle As seen in the data from Table 1, The Ex 1-4 resin compositions that encompassed NBane-type PACs in accordance with embodiments of the present invention, showed increased photo sensitivity, resolution and increased feature size stability in comparison to the each Comparative Example that employed the same resin but with a previously known commercial PAC.

Polynorbornene System

The photoactive formulation examples presented below demonstrate the effectiveness of NBane-type PAC embodiments in accordance with the present invention formulated with an exemplary PNB resin (A*). Examples are identified by the specific NBane-type PAC employed and each example includes both formulation methods and imaging data.

Photoactive formulation P475 PAC; Example PAC11

8.40 g of an addition polymerized polynorbornene polymer composed of endo,exo-2-(bicyclo[22.2.1]hept-5-en-2-ylmethyl)-1,1,1,3,3,3-hexafluoropropan-2-ol (HFANB) (75 mol %) and endo,exo-3-(bicyclo[2.2.1]hept-5-en-2-yl)propanoic acid (EPENB) (25 mol %) was dissolved in PGMEA (14.1 g) to yield a polymer solution at 37.8 wt. % solids. This polymer solution was filtered through a 0.5 μm Teflon® filter to remove gels and dust contamination and placed in an amber, low particle 125 mL bottle. Next, PP475 PAC (2.10 g) and PGMEA (5.42 g) was charged into the filtered polymer solution. The suspension of solid PP475 PAC in PGMEA polymer solution was mixed on a roller for 18 hours at ambient temperature until a homogeneous solution of PNB photoactive formulation 1 was achieved. The photoactive solution was filtered through a 5.0 μm Teflon filter to remove any remaining undissolved solid material.

Photoactive formulation 1 was applied to a 100 mm Si wafer by spin coating at a first speed of 500 rpm for 10 seconds and then a second speed of 2500 rpm for a further 30 seconds to yield a contiguous polymer film 9.96 μm thick. The wafer was transferred to a hot plate and baked for 5 minutes at 100° C. The polymer film was patterned by an image-wise exposure to 1000 mJ/cm2 of 365 nm UV radiation through a test pattern mask comprising a chrome metal test pattern on a glass substrate. The exposed sample was allowed to sit at ambient temperature for 10 minutes. The latent pattern was then developed by using a multistep puddle and spray rinse develop recipe 2.38% tetramethylammonium hydroxide (TMAH) developer (Shipley CD-26). A 25 mL aliquot of CD-26 was puddled on the wafer for twenty (20) seconds and then the wafer was spun at 200 rpm for 10 seconds and the wafer was rinsed with deionized water. The puddle and spray develop process was repeated a total of two times. A minimum pattern resolution of 7 μm lines with a pitch of 70 μm was obtained.

Formulation Examples 2 through 6, which incorporated PP308 PAC, PP459 PAC and P343 PAC as additives, were evaluated using the method described for Formulation 1. The evaluation data for each of Formulation Examples 1 through 6 is presented in Table 2, below.

Comparative Example 1 was generated using the TrisP-PA PAC from Example PAC4 presented above, but where the DNQ loading was 67%. This PAC was obtained from Toyo Gosei Inc. of Japan. For Comparative Example 2 PROM1060/PAC 889 (100% DNQ functionality) was employed. Both Comparative Examples were formulated using the same PNB resin (A*) employed for Examples 1 through 6 and were evaluated using the method described for Formulation 1.

TABLE 2

| Formulation | DNQ PAC | DNQ PAC Loading | Weight of polymer (g) | Weight of DNQ PAC (g) | Weight of PGMEA (g) | Lithography Data Sensitivity (mJ/cm$^2$) | Resolution (μm) | DR Data Exposed (1 J/cm$^2$) (nm/sec) |
|---|---|---|---|---|---|---|---|---|
| Comparative 1 | †TrisP-3M6C-2-201 | 25 phr | 8.39 | 2.10 | 19.4 | 404 | 7 | 330.9 |
| Comparative 2 | PROM1060/PAC889 | 25 phr | 8.40 | 2.10 | 19.6 | 976 | 5 | 332.1 |
| 1 | PP475 PAC | 25 phr | 8.40 | 2.10 | 19.5 | 976 | 7 | 282.6 |
| 2 | PP308 PAC | 20 phr | 8.75 | 1.75 | 19.6 | 976 | 10 | 961.0 |
| 3 | PP459 PAC | 25 phr | 11.0 | 2.80 | 26.2 | 604 | 20 | 205.4 |
| 4 | P343 PAC | 25 phr | 11.2 | 2.80 | 26.4 | 404 | 7 | 395.8 |
| 5 | P343 PAC | 20 phr | 9.13 | 1.37 | 19.5 | 194 | 10 | 515.3 |

† the DNQ loading for this PAC was targeted at 67%, all other were targeted at 100%

As it is seen in Table 2, the formulations made with P343 PAC were equal to or better than the comparative examples with regard to sensitivity.

By now it should be realized that PBO resin (A) formulations demonstrate significantly better imaging and dimensional stability where a NBane-type PAC embodiment in accordance with the present invention is used. With regard to PNB resin (A*) formulations, P343 PAC showed sensitivity performance equal to or better than Comparative Example 1 and much better performance with regard Comparative Example 2, much better sensitivity performance.

What is claimed is:

1. A compound of formula AA or BB:

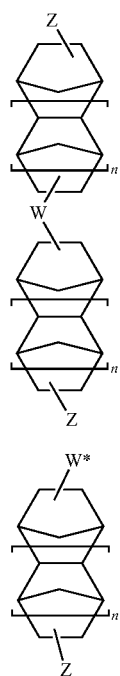

AA

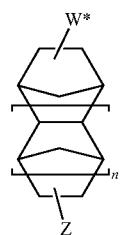

BB wherein n independently of each other is an integer from 0 to 3;

Z is selected independently from one or more of structures C or D:

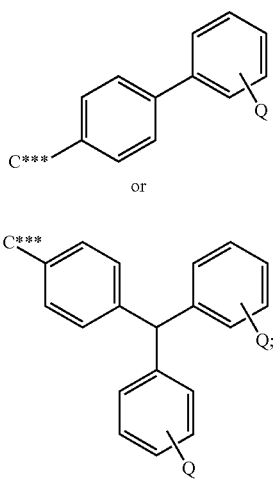

where C*** represents a carbon atom of a norbornane ring and Q represents from one to five substituents independently selected from —OH, a halogen, a $C_1$ to $C_6$ alkyl group, a $C_3$ to $C_{12}$ cycloalkyl group, an aryl and an alkaryl group, n is from 0 to 4, and with the provisos that at least one of such substituents is —OH;

W in formula AA is either a covalent bond or a divalent linking group selected from a $C_1$ to $C_{12}$ alkyl, ether or polyether, a $C_3$ to $C_{12}$ cycloalkyl, aryl or alkaryl group, or one or more norbornane-type moieties;

W* in formula BB is hydrogen, a monovalent group selected from a $C_1$ to $C_{12}$ alkyl, ether or polyether, a $C_3$ to $C_{12}$ cycloalkyl, aryl or alkaryl group, or one or more norbornane-type moieties.

2. The compound of claim 1, wherein W* is selected from:

—$(CH_2)_n$*$CH_3$, —$(CH_2)_n$Ph, —$(CH_2)_sO(CH_2CH_2O)_tH$, —$(CH_2)_sO(CH_2CH_2O)_sC(O)CH_3$, —$(CH_2)_s(O)CH_3$, —$(CH_2)_sO(CH_2CH_2O)_t$*$CH_3$, —$(CH_2)_sOCH_2CH_2OCH_2C(CF_3)_2OH$, —$(CH_2)_sC(CF_3)_2OH$, —$(CH_2)_sOCH_2C(CF_3)_2OH$, —$(CH_2)_sCO_2Et$, —$(CH_2)_sCO_2H$, —$(CH_2)_sC_6H_4OH$, —$(CH_2)_sC(O)C_6H_4OH$, —$(CH_2)_sC(O)NHC_6H_4OH$, or —$(CH_2)_sN(H)S(O)_2CF_3$; wherein n is an integer from 0 to 6;

n* is an integer from 0 to 11;

s is an integer from 1 to 6; and t is 0 or 3; and t* is 2 or 3.

3. The compound of claim 1, wherein W is selected from:

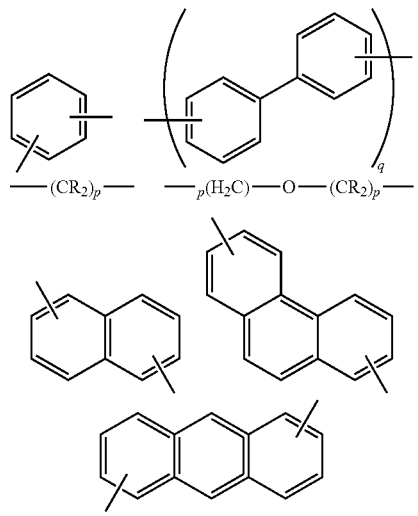

where p independently of each other is an integer from 1 to 10;

q is an integer from 1 to 3; and

R is hydrogen or a C1 to C4 alkyl.

4. The compound of claim 1, wherein W is selected from:

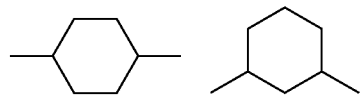

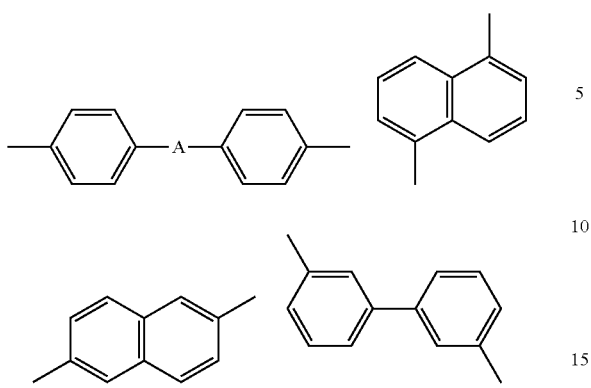
where A is selected from O, C(O), $CH_2$, $C(CH_3)_2$, $C(CF_3)_2$ or $SO_2$.
5. The compound of claim 1, which is of formula BB and is selected from the following:
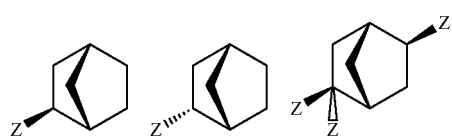
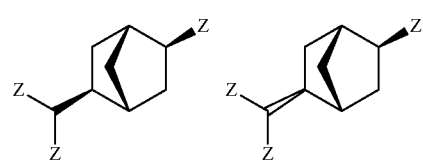
where Z is as defined in claim 1.
6. A compound selected from the following:
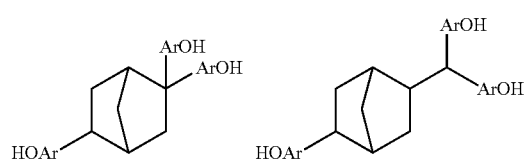
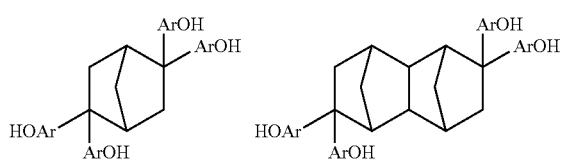
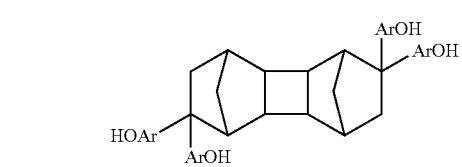
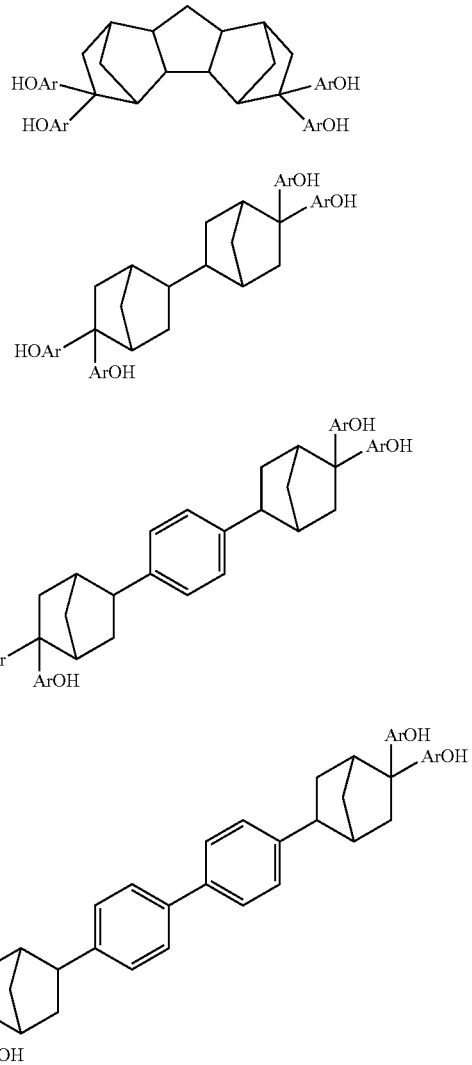

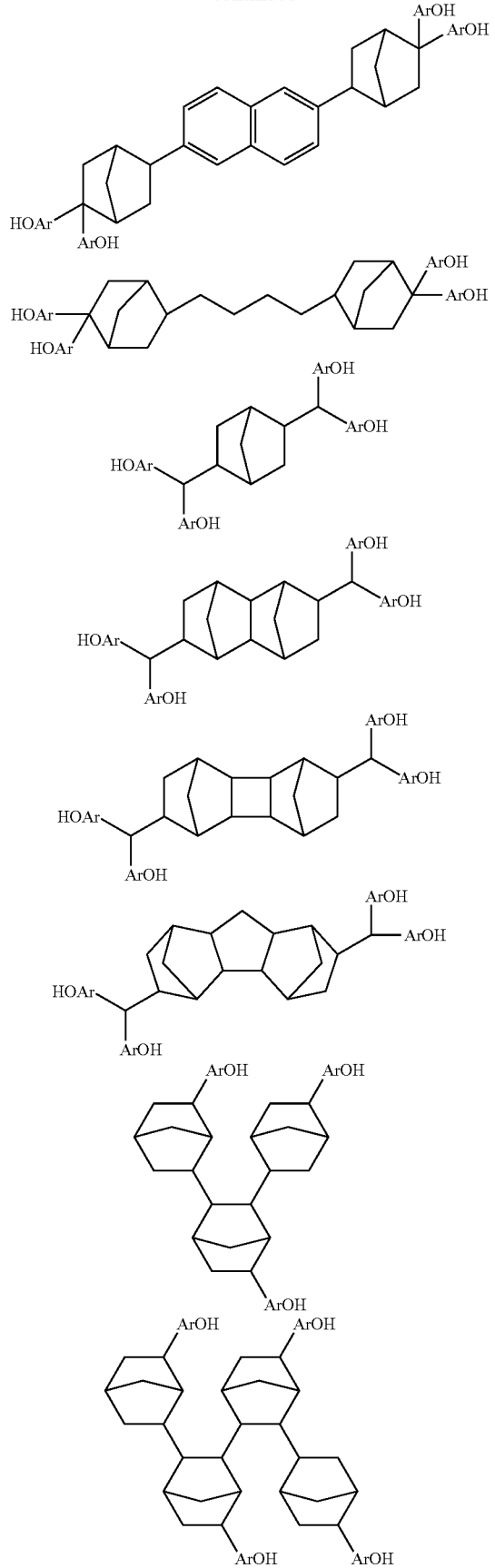
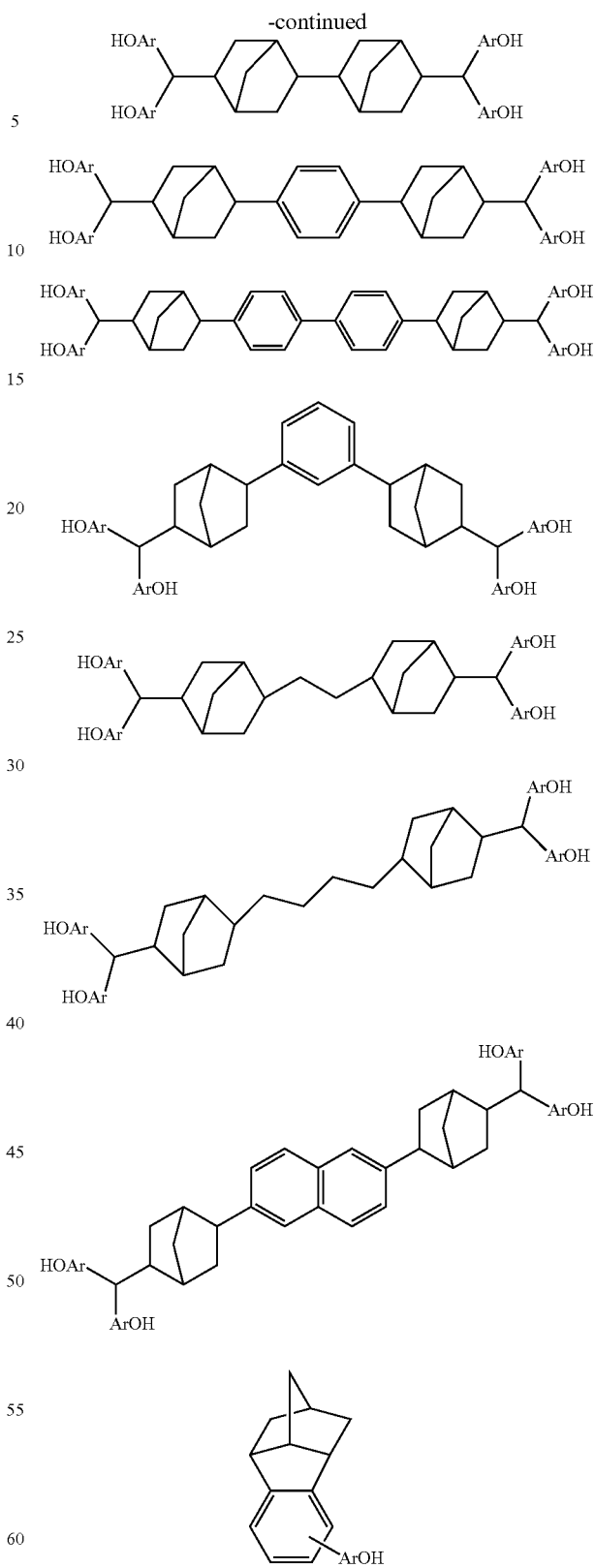
where ArOH represents a substituted or unsubstituted hydroxyaryl moiety.
7. The compound of claim 1, which is selected from the following:

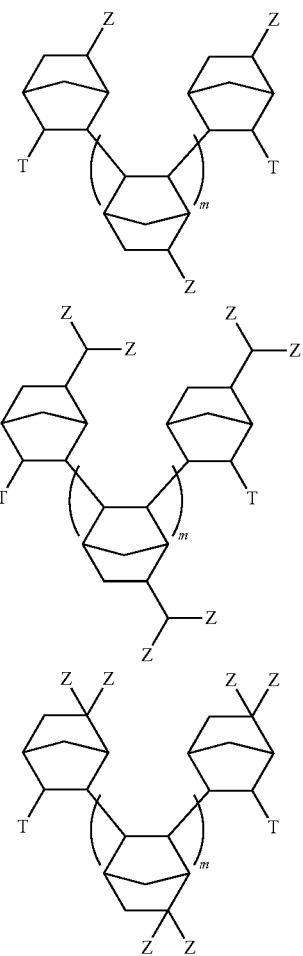

wherein Z is as defined in claim 1, m is an integer from 1 to 10 and T is hydrogen.

8. The compound of claim 1, wherein at least one of the hydrogen of the —OH is replaced by one of the benzoquinone (BQ) or diazonaphthoquinone DNQ moieties represented by Formulae F, G or H respectively:

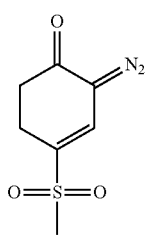

F

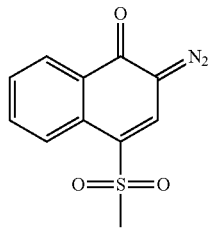

G

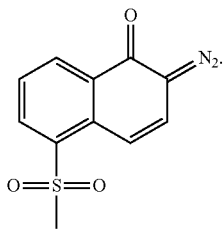

H

9. A Compound selected from the group consisting of:
4-(5-hexylbicyclo[2.2.1]heptan-2-yl)-2-methylphenol;
4-(5-hexylbicyclo[2.2.1]heptan-2-yl)-2-isopropylphenol;
2-cyclohexyl-4-(5-hexylbicyclo[2.2.1]heptan-2-yl)-5-methylphenol;
4-(5-decylbicyclo[2.2.1]heptan-2-yl)-2-methylphenol;
4-(5-decylbicyclo[2.2.1]heptan-2-yl)-2-isopropylphenol;
2-cyclohexyl-4-(5-decylbicyclo[2.2.1]heptan-2-yl)-5-methylphenol;
4-(5-2,5,8,11-tetraoxadodecylbicyclo[2.2.1]heptan-2-yl)-2-methylphenol;
4-(5-2,5,8,11-tetraoxadodecylbicyclo[2.2.1]heptan-2-yl)-2-isopropylphenol;
4-(5-2,5,8,11-tetraoxadodecylbicyclo[2.2.1]heptan-2-yl)-2-cyclohexyl-5-methyl-phenol;
2-methyl-4-(5-phenylbicyclo[2.2.1]heptan-2-yl)phenol;
2-isopropyl-4-(5-phenylbicyclo[2.2.1]heptan-2-yl)phenol;
2-cyclohexyl-4-(5-phenylbicyclo[2.2.1]heptan-2-yl)phenol;
ethyl 3-(5-(4-hydroxy-3-methylphenyl)bicyclo[2.2.1]heptan-2-yl)propanoate;
ethyl 3-(5-(4-hydroxy-3-isopropylphenyl)bicyclo[2.2.1]heptan-2-yl)propanoate;
ethyl 3-(5-(3-cyclohexyl-4-hydroxyphenyl)bicyclo[2.2.1]heptan-2-yl)propanoate;
4-(bicyclo[2.2.1]heptan-2-yl)-2-isopropylphenol;
4-(5-((2-methoxyethoxy)methyl)bicyclo[2.2.1]heptan-2-yl)-2-methylphenol;
2-isopropyl-4-(5-((2-methoxyethoxy)methyl)bicyclo[2.2.1]heptan-2-yl)phenol;
2-cyclohexyl-4-(5-((2-methoxyethoxy)methyl)bicyclo[2.2.1]heptan-2-yl)-5-methyl-phenol;
4-(5-((2-(2-methoxyethoxy)ethoxy)methyl)bicyclo[2.2.1]heptan-2-yl)-2-methylphenol;
2-isopropyl-4-(5-((2-(2-methoxyethoxy)methyl)-bicyclo[2.2.1]heptan-2-yl)-phenol;
2-cyclohexyl-4-(5-((2-(2-methoxyethoxy)ethoxy)methyl)-bicyclo[2.2.1]heptan-2-yl)-5-methylphenol;
2-methyl-4-(5-(3,3,3-trifluoro-2-hydroxy-2-(trifluoromethyl)propyl)-bicyclo[2.2.1]-heptan-2-yl)phenol;
2-isopropyl-4-(5-(3,3,3-trifluoro-2-hydroxy-2-(trifluoromethyl)propyl)-bicyclo[2.2.1]-heptan-2-yl)phenol;
2-cyclohexyl-4-(5-(3,3,3-trifluoro-2-hydroxy-2-(trifluoromethyl)propyl)-bicyclo[2.2.1]-heptan-2-yl)phenol;
4-(5-benzylbicyclo[2.2.1]heptan-2-yl)-2-methylphenol;
4-(5-benzylbicyclo[2.2.1]heptan-2-yl)-2-isopropylphenol;
4-(5-(2-methylbicyclo[2.2.1]heptane)bicyclo[2.2.1]heptan-2-yl)-2-cyclohexylphenol; 4-(bicyclo[2.2.1]heptan-2-yl)-2-cyclohexylphenol;
4-(5-benzylbicyclo[2.2.1]heptan-2-yl)-2-methylphenol;
4-(5-(2-methylbicyclo[2.2.1]heptane)bicyclo[2.2.1]heptan-2-yl)-2-isopropylphenol;

4-(5-(2-methylbicyclo[2.2.1]heptane)bicyclo[2.2.1]heptan-2-yl)-2-cyclohexylphenol;
4-(decahydro-1,4:5,8-dimethanonaphthalen-2-yl)-2-methylphenol;
4-(decahydro-1,4:5,8-dimethanonaphthalen-2-yl)-2-isopropylphenol;
4-(decahydro-1,4:5,8-dimethanonaphthalen-2-yl))-2-cyclohexylphenol;
4-(5-(4-hydroxybenzyl)bicyclo[2.2.1]heptan-2-yl)-2-methylphenol;
4-(5-(4-hydroxybenzyl)bicyclo[2.2.1]heptan-2-yl)-2,5-dimethylphenol;
2-cyclohexyl-4-(5-(methoxymethyl)bicyclo[2.2.1]heptan-2-yl)-5-methylphenol;
4-(5-(methoxymethyl)bicyclo[2.2.1]heptan-2-yl)-2-methylphenol;
2-methyl-4-(5-((oxiran-2-ylmethoxy)methyl)bicyclo[2.2.1]heptan-2-yl)phenol;
2-cyclohexyl-5-methyl-4-(5-((oxiran-2-ylmethoxy)methyl)bicyclo[2.2.1]-heptan-2-yl)phenol;
2-methyl-4-(5-(6-(oxiran-2-yl)hexyl)bicyclo[2.2.1]heptan-2-yl)phenol;
2-cyclohexyl-5-methyl-4-(5-(6-(oxiran-2-yl)hexyl)bicyclo[2.2.1]heptan-2-yl)phenol;
2-cyclohexyl-4-(5-(methoxymethyl)bicyclo[2.2.1]heptan-2-yl)-5-methylphenol;
4-(5-(hydroxymethyl)bicyclo[2.2.1]heptan-2-yl)-2-methylphenol;
5-(5-cyclohexyl-4-hydroxy-2-methylphenyl)bicyclo[2.2.1]heptan-2-yl)methyl acetate;
(5-(4-hydroxy-3-methylphenyl)bicyclo[2.2.1]heptan-2-yl)methyl acetate;
4,4'-((5-(4-hydroxy-3-methylphenyl)bicyclo[2.2.1]heptan-2-yl)methylene)bis(2-methylphenol);
4,4'-((5-(4-hydroxy-3-isopropylphenyl)bicyclo[2.2.1]heptan-2-yl)methylene)bis(2-isopropylphenol);
4,4'-((5-(3-cyclohexyl-4-hydroxyphenyl)bicyclo[2.2.1]heptan-2-yl)methylene)bis-(2-methylphenol);
4,4'-((5-(4-hydroxyphenyl)bicyclo[2.2.1]heptan-2-yl)methylene)bis(2-methylphenol);
4,4',4"-(bicyclo[2.2.1]heptane-2,2,5-triyl)tris(2-methylphenol);
4,4',4"-(bicyclo[2.2.1]heptane-2,2,5-triyl)tris(2-isopropylphenol); 4,4'-(5-(3-cyclohexyl-4-hydroxyphenyl)bicyclo[2.2.1]heptane-2,2-diyl)bis-(2-methylphenol);
4,4'-(5-(4-hydroxyphenyl) bicyclo[2.2.1]heptane-2,2-diyl)bis(2-methylphenol);
5'-(5-(4-hydroxybenzyl)bicyclo[2.2.1]heptan-2-yl)-3,3"-dimethyl-[1,1':3',1"terphenyl]-4,4"-diol;
5'-(5-(4-hydroxyphenyl)bicyclo[2.2.1]heptan-2-yl)-3,3"-dimethyl-[1,1':3',1"terphenyl]-4,4"-diol;
4,4',4'",4'"-(5,5')-1,4-phenylene)bis(bicyclo[2.2.1]heptane-5,2-diyl))bis-(methanetriyl)tetrakis(2-methylphenol);
4,4',4'",4'"-(5,5'-(1,4-phenylene)bis(bicyclo[2.2.1]heptane-5,2-diyl))bis-(methanetriyl)tetrakis(2-cyclohexyl-5-methylphenol);
4,4',4'",4'"-(5,5'-(1,4-phenylene)bis(bicyclo[2.2.1]heptane-5,2-diyl))bis-(methanetriyl)tetrakis(2-isopropylphenol);
4,4',4'",4'"-(5,5'-(1,4-phenylene)bis(bicyclo[2.2.1]heptane-5,2-diyl)bis-(methanetriyl)tetrakis(2,5-dimethylphenol);
4,4',4'",4'"-(5,5'-(1,4-phenylene)bis(bicyclo[2.2.1]heptane-5, 2, 2-triyl))-tetrakis(2-methylphenol);
4,4'-(5-(4-(5-(5-cyclohexyl-4-hydroxy-2-methylphenyl)-5-(3-cyclohexyl-4-hydroxyphenyl)bicyclo[2.2.1]heptan-2-yl)phenyl)bicyclo[2.2.1]heptane-2,2-diyl)bis(2-cyclohexyl-5-methylphenol);
4,4',4",4'"-(5,5'-(1,4-phenylene)bis(bicyclo[2.2.1]heptane-5,2,2-triyl)tetrakis-(2,5-dimethylphenol); and
5'-(5-(bis(4-hydroxy-2,5-dimethylphenyl)methyl)bicyclo[2.2.1]heptan-2-yl)-3,3"-dimethyl-[1,1':3',1"-terphenyl]-4,4"-diol.

10. A Compound selected from the group consisting of:
4,4'-(((5S)-5-phenylbicyclo[2.2.1]heptan-2-yl)methylene)bis(2-methylphenol);
4,4'-((5S)-5-phenylbicyclo[2.2.1]heptane-2,2-diyl)bis(2-methylphenol);
4,4'-((5-phenylbicyclo[2.2.1]heptan-2-yl)methylene)bis(2-isopropyl-5-methylphenol);
4-(2-(4-hydroxy-3-isopropyl-5-methylphenyl)-5-phenylbicyclo[2.2.1]heptan-2-yl)-2-isopropyl-5-methylphenol;
4,4'-((5-phenylbicyclo[2.2.1]heptan-2-yl)methylene)bis(2-cyclohexyl-5-methylphenol);
2-cyclohexyl-4-(2-(3-cyclohexyl-4-hydroxy-5-methylphenyl)-5-phenylbicyclo[2.2.1]-heptan-2-yl)-5-methylphenol;
4,4'-(bicyclo[2.2.1]heptane-2,5-diyl)bis(2-methylphenol);
4,4'-(bicyclo[2.2.1]heptane-2,5-diyl)bis(2-isopropylphenol);
4,4'-(bicyclo[2.2.1]heptane-2,5-diyl)bis(2-cyclohexyl-5-methylphenol);
4,4'-(tetracyclo[6.2.1.13,6.02,7]dodecan-2,7-diyl)bis(2-cyclohexyl-5-methylphenol);
4,4'-(5,5'-(2,2'-oxybis(ethane-2,1-diyl))bis(bicyclo[2.2.1]heptane-5,2-diyl))-bis(2-cyclohexylphenol);
4,4'-(5,5'-(2,2'-oxybis(ethane-2,1-diyl))bis(bicyclo[2.2.1]heptane-5,2-diyl))-bis(2-isopropylphenol);
4,4'-(5,5'-(2,2'-oxybis(ethane-2,1-diyl))bis(bicyclo[2.2.1]heptane-5,2-diyl))-bis(2-methylphenol);
4,4'-(5,5'-(butane-1,4-diyl)bis(bicyclo[2.2.1]heptane-5,2-diyl))bis(2-methylphenol);
4,4'-(5,5'-(butane-1,4-diyl)bis(bicyclo[2.2.1]heptane-5,2-diyl))bis(2-isopropylphenol);
2-cyclohexyl-4-(5-(4-(5-(3-cyclohexyl-4-methylphenyl)bicyclo[2.2.1]heptan-2-yl)butyl)bicyclo[2.2.1]heptan-2-yl)phenol;
4,4'-(tetracyclo[6.2.1.13,6.02,7]dodecan-2-ylmethylene)bis(2-methylphenol);
4,4'-(tetracyclo[6.2.1.13,6.02,7]dodecan-2-ylmethylene)bis(2-isopropylphenol);
4,4'-(tetracyclo[6.2.1.13,6.02,7]dodecan-2-ylmethylene)bis(2-cyclohexyl-5-methylphenol);
4,4'-(5,5'-(1,4-phenylene)bis(bicyclo[2.2.1]heptane-5,2-diyl))bis(2-methylphenol);
4,4'-(5,5'-(1,4-phenylene)bis(bicyclo[2.2.1]heptane-5,2-diyl))bis(2-isopropylphenol);
4,4'-(5,5'-(1,4-phenylene)bis(bicyclo[2.2.1]heptane-5,2-diyl))bis(2-cyclohexylphenol);
4,4'-(5,5'-(biphenyl-4,4'-diyl)bis(bicyclo[2.2.1]heptane-5,2-diyl))bis(2-methylphenol);
4,4'-(5,5'-(biphenyl-4,4'-diyl)bis(bicyclo[2.2.1]heptane-5,2-diyl))bis(2-isopropylphenol);
4,4'-(5,5'-(biphenyl-4,4'-diyl)bis(bicyclo[2.2.1]heptane-5,2-diyl))bis-(2-cyclohexylphenol);
4,4'-(pentacyclo[8.2.1.14,7.02,9.08,3]tetradecan-2,8-yl)bis(2-methylphenol);
4,4'-(pentacyclo[8.2.1.14,7.02,9.08,3]tetradecan-2,8-yl)bis(2-isopropylphenol);

4,4'-(pentacyclo[8.2.1.1⁴,⁷.0².⁹.0⁸,³]tetradecan-2,8-yl)bis(2-cyclohexyl-5-methylphenol);

4,4'-(dodecahydro-1,4:5,8-dimethanobiphenylene-2,6-diyl)bis(2-methylphenol);

4,4'-(dodecahydro-1,4:5,8-dimethanobiphenylene-2,6-diyl)bis(2-isopropylphenol); and 4,4'-(dodecahydro-1,4:5,8-dimethanobiphenylene-2,6-diyl)bis(2-cyclohexyl-5-methylphenol).

11. The Compound of claim 9, which is selected from the group consisting of:

4,4'-((5-(4-hydroxy-3-methylphenyl)bicyclo[2.2.1]heptan-2-yl)methylene)bis(2-methylphenol);

4,4'-((5-(4-hydroxy-3-isopropylphenyl)bicyclo[2.2.1]heptan-2-yl)methylene)bis(2-isopropylphenol);

4,4'-((5-(3-cyclohexyl-4-hydroxyphenyl)bicyclo[2.2.1]heptan-2-yl)methylene)bis-(2-methylphenol);

4,4'-((5-(4-hydroxyphenyl)bicyclo[2.2.1]heptan-2-yl)methylene)bis(2-methylphenol);

4,4',4''-(bicyclo[2.2.1]heptane-2,2,5-triyl)tris(2-methylphenol);

4,4',4''-(bicyclo[2.2.1]heptane-2,2,5-triyl)tris(2-isopropylphenol);

cyclohexyl-4-hydroxyphenyl)bicyclo[2.2.1]heptane-2,2-diyl)bis-(2-methylphenol);

4,4'-(5-(4-hydroxyphenyl) bicyclo[2.2.1]heptane-2,2-diyl)bis(2-methylphenol);

5'-(5-(4-hydroxybenzyl)bicyclo[2.2.1]heptan-2-yl)-3,3''-dimethyl-[1,1':3',1''terphenyl]-4,4''-diol; and 5'-(5-(4-hydroxyphenyl)bicyclo[2.2.1]heptan-2-yl)-3,3''-dimethyl-[1,1':3',1''-terphenyl]-4,4''-diol.

12. The Compound of claim 9, which is selected from the group consisting of:

4,4',4'',4'''-(5,5'-(1,4-phenylene)bis(bicyclo[2.2.1]heptane-5,2-diyl))bis-(methanetriyl)tetrakis(2-methylphenol);

4,4',4'',4'''-(5,5'-(1,4-phenylene)bis(bicyclo[2.2.1]heptane-5,2-diyl))bis-(methanetriyl)tetrakis(2-cyclohexyl-5-methylphenol);

4,4',4'',4'''-(5,5'-(1,4-phenylene)bis(bicyclo[2.2.1]heptane-5,2-diyl))bis-(methanetriyl)tetrakis(2-isopropylphenol);

4,4',4'',4'''-(5,5'-(1,4-phenylene)bis(bicyclo[2.2.1]heptane-5,2,2-diyl))bis-(methanetriyl)tetrakis(2,5-dimethylphenol);

4,4',4'',4'''-(5,5'-(1,4-phenylene)bis(bicyclo[2.2.1]heptane-5,2,2-triyl))-tetrakis(2-methylphenol);

4,4'-(5-(4-(5-(5-cyclohexyl-4-hydroxy-2-methylphenyl)-5-(3-cyclohexyl-4-hydroxyphenyl)bicyclo[2.2.1]heptan-2-yl)phenyl)bicyclo[2.2.1]heptane-2,2-diyl)bis(2-cyclohexyl-5-methylphenol);

4,4',4'',4'''-(5,5'-(1,4-phenylene)bis(bicyclo[2.2.1]heptane-5,2,2-triyl))tetrakis-(2,5-dimethylphenol); and 5'-(5-(bis(4-hydroxy-2,5-dimethylphenyl)methyl)bicyclo[2.2.1]heptan-2-yl)-3,3''-dimethyl-[1,1':3',1''-terphenyl]-4,4''-diol.

13. A norbornane-type photoactive compound of formula AA or BB:

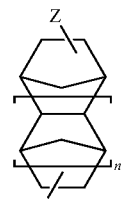

AA

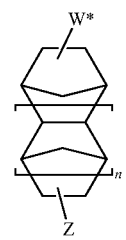

BB wherein n independently of each other is an integer from 0 to 3;

Z represents one to four substituted or unsubstituted ArOD substituents, where Ar is an aryl group and where at least one of D is one of benzoquinone (BQ) or diazonaphthoquinone DNQ moieties represented by Formulae F, G or H respectively:

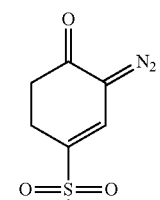

F

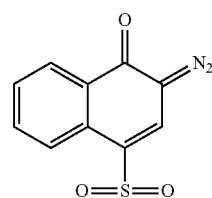

G

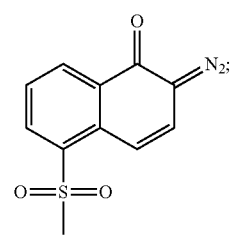

H and the remaining D is hydrogen;

W in formula AA is either a covalent bond or a divalent linking group selected from a $C_1$ to $C_{12}$ alkyl, ether or polyether, a $C_3$ to $C_{12}$ cycloalkyl, aryl or alkaryl group, or one or more norbornane-type moieties;

W* in formula BB is hydrogen, a monovalent group selected from a $C_1$ to $C_{12}$ alkyl, ether or polyether, a $C_3$ to $C_{12}$ cycloalkyl, aryl or alkaryl group, or one or more norbornane-type moieties.

14. The photoactive active compound according to claim 13, wherein W* is selected from:

—$(CH_2)_{n^*}CH_3$, —$(CH_2)_n Ph$, —$(CH_2)_s O(CH_2CH_2O)_t H$, —$(CH_2)_s O(CH_2CH_2O)_t C(O)CH_3$, —$(CH_2)_s (O)CH_3$, —$(CH_2)_s O(CH_2CH_2O)_{t^*} CH_3$, —$(CH_2)_s OCH_2CH_2 OCH_2C(CF_3)_2OH$, —$(CH_2)_s C(CF_3)_2OH$, —$(CH_2)_s OCH_2C(CF_3)_2OH$, —$(CH_2)_s CO_2Et$, —$(CH_2)_s CO_2H$, —$(CH_2)_s C_6H_4OH$, —$(CH_2)_s C(O)C_6H_4OH$, —$(CH_2)_s C(O)NHC_6H_4OH$, and —$(CH_2)_s N(H)S(O)_2CF_3$; wherein
n is an integer from 0 to 6;
n* is an integer from 0 to 11;
s is an integer from 1 to 6; and
t is 0 or 3; and
t* is 2 or 3.

15. The photoactive active compound according to claim 13, wherein Z is selected independently from one or more of structures A, B, C, D or E:

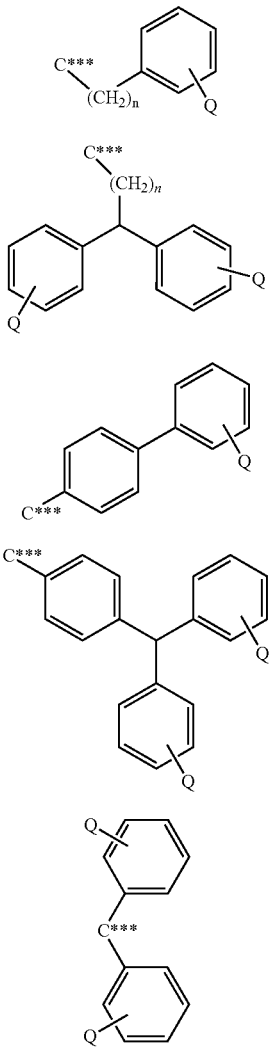

where C*** represents a carbon atom of a norbornane ring and Q represents from one to five substituents independently selected from —OH, a halogen, a $C_1$ to $C_6$ alkyl group, a $C_3$ to $C_{12}$ cycloalkyl group, an aryl and an alkaryl group, n is from 0 to 4, and with the provisos that at least one of such substituents is —OH.

16. The photoactive active compound according to claim 13, wherein W is selected from:

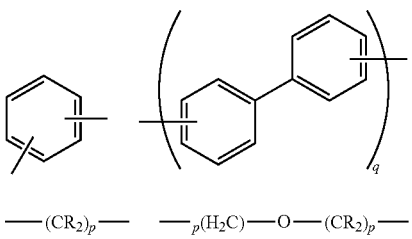

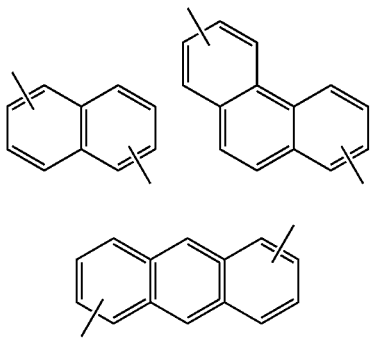

where p independently of each other is an integer from 1 to 10;
q is an integer from 1 to 3; and
R is hydrogen or a $C_1$ to $C_4$ alkyl.

17. A positive-tone photosensitive resin composition comprising one of an alkali soluble (A) having a benzoxazole precursor structure in the main chain or an alkali-soluble polynorbornene resin (A*) having a polynorbornene-type structure in the main chain;

a norbornane-type photoactive compound according to claim 13; and a casting solvent.

18. The positive-tone photosensitive resin composition of claim 17, wherein W of the norbornane-type photoactive compound is selected from:

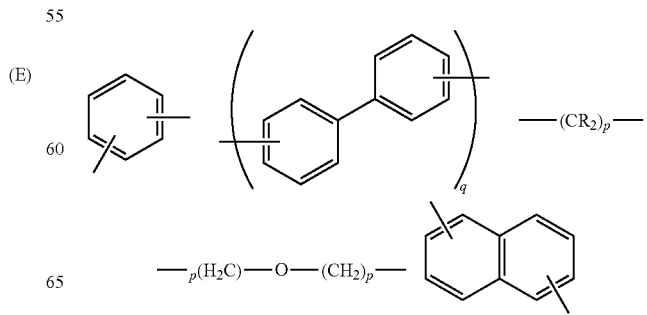

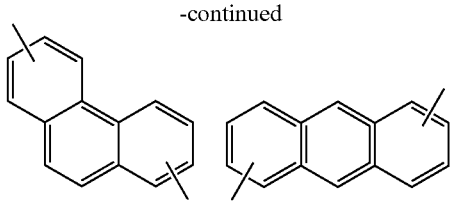
where p independently of each other is an integer from 1 to 10;
q is an integer from 1 to 3; and
R is hydrogen or a $C_1$ to $C_4$ alkyl.
19. The positive-tone photosensitive resin composition of claim 17 where the alkali-soluble resin is having a benzoxazole precursor structure in the main chain.
* * * * *